(12) United States Patent
Thornton et al.

(10) Patent No.: US 8,470,028 B2
(45) Date of Patent: Jun. 25, 2013

(54) METHODS, SYSTEMS AND DEVICES FOR CARDIAC VALVE REPAIR

(75) Inventors: Troy L. Thornton, San Francisco, CA (US); Eric A. Goldfarb, Belmont, CA (US); Kent D. Dell, Redwood City, CA (US); Jaime E. Sarabia, Mableton, GA (US); Steven A. Tyler, Portola Valley, CA (US); Kristin Ellis, San Jose, CA (US); Jayanth Chakravarthy, Santa Clara, CA (US)

(73) Assignee: Evalve, Inc., Menlo Park, CA (US)

( * ) Notice: Subject to any disclaimer, the term of this patent is extended or adjusted under 35 U.S.C. 154(b) by 483 days.

(21) Appl. No.: 12/689,958

(22) Filed: Jan. 19, 2010

(65) Prior Publication Data
US 2011/0066233 A1 Mar. 17, 2011

Related U.S. Application Data

(60) Provisional application No. 61/242,506, filed on Sep. 15, 2009.

(51) Int. Cl.
*A61F 2/24* (2006.01)
(52) U.S. Cl.
USPC .............................. 623/2.36; 623/2.11
(58) Field of Classification Search
USPC .................................. 623/2.11–2.37
See application file for complete search history.

(56) References Cited

U.S. PATENT DOCUMENTS

| | | |
|---|---|---|
| 2,097,018 A | 10/1937 | Chamberlain |
| 2,108,206 A | 2/1938 | Meeker |
| 3,378,010 A | 4/1968 | Codling et al. |
| 3,671,979 A | 6/1972 | Moulopoulos |
| 3,874,338 A | 4/1975 | King et al. |
| 4,056,854 A | 11/1977 | Boretos et al. |
| 4,064,881 A | 12/1977 | Meredith |
| 4,112,951 A | 9/1978 | Hulka et al. |
| 4,297,749 A | 11/1981 | Davis et al. |
| 4,484,579 A | 11/1984 | Meno et al. |
| 4,498,476 A | 2/1985 | Cerwin et al. |
| 4,510,934 A | 4/1985 | Batra |
| 4,809,695 A | 3/1989 | Gwanthmey et al. |
| 4,917,089 A | 4/1990 | Sideris |

(Continued)

FOREIGN PATENT DOCUMENTS

| | | |
|---|---|---|
| EP | 179562 | 7/1989 |
| EP | 558031 | 9/1993 |

(Continued)

OTHER PUBLICATIONS

Abe et al., "De Vega's annuloplasty for acquired tricuspid disease: Early and late results in 110 patients" Ann. Thorac. Surg. (1989) 4.8:670-676.

(Continued)

*Primary Examiner* — Suzette J Gherbi
(74) *Attorney, Agent, or Firm* — Sughrue Mion, PLLC; Jonathan D. Feuchtwang

(57) ABSTRACT

Disclosed are devices and methods for treating regurgitation through a valve in the heart. The devices can include an expandable, fluid-tight bladder configured to be deployed between valve leaflets of the heart valve. The bladder can include an upper portion that extends into the atrium of the heart; a lower portion that extends into the ventricle of the heart; and a middle portion positionable within the line of valve leaflet coaptation that provides a sealing surface for one or more of the leaflets.

5 Claims, 39 Drawing Sheets

U.S. PATENT DOCUMENTS

| | | |
|---|---|---|
| 4,944,295 A | 7/1990 | Gwathmey et al. |
| 4,994,077 A | 2/1991 | Dobben |
| 5,015,249 A | 5/1991 | Nakao et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,190,554 A | 3/1993 | Coddington et al. |
| 5,195,968 A | 3/1993 | Lundquist et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,250,071 A | 10/1993 | Palermo |
| 5,254,130 A | 10/1993 | Ponce et al. |
| 5,261,916 A | 11/1993 | Engelson |
| 5,275,578 A | 1/1994 | Adams |
| 5,312,415 A | 5/1994 | Palermo |
| 5,314,424 A | 5/1994 | Nicholas |
| 5,318,525 A | 6/1994 | West et al. |
| 5,325,845 A | 7/1994 | Adair |
| 5,332,402 A | 7/1994 | Teitelbaum |
| 5,350,397 A | 9/1994 | Palermo et al. |
| 5,359,994 A | 11/1994 | Krauter et al. |
| 5,368,564 A | 11/1994 | Savage |
| 5,368,601 A | 11/1994 | Sauer et al. |
| 5,383,886 A | 1/1995 | Kensey et al. |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,858 A | 6/1995 | Bolanos et al. |
| 5,423,882 A | 6/1995 | Jackman et al. |
| 5,431,666 A | 7/1995 | Sauer et al. |
| 5,437,681 A | 8/1995 | Meade et al. |
| 5,450,860 A | 9/1995 | O'Connor |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,487,746 A | 1/1996 | Yu et al. |
| 5,507,725 A | 4/1996 | Savage et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,571,085 A | 11/1996 | Accisano |
| 5,571,137 A | 11/1996 | Marlow et al. |
| 5,571,215 A | 11/1996 | Sterman et al. |
| 5,582,611 A | 12/1996 | Tsuruta et al. |
| 5,593,424 A | 1/1997 | Northrup, III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,626,588 A | 5/1997 | Sauer et al. |
| 5,634,932 A | 6/1997 | Schmidt |
| 5,636,634 A | 6/1997 | Kordis et al. |
| 5,640,955 A | 6/1997 | Ockuly et al. |
| 5,649,937 A | 7/1997 | Bito et al. |
| 5,669,917 A | 9/1997 | Sauer et al. |
| 5,690,671 A | 11/1997 | McGurk et al. |
| 5,706,824 A | 1/1998 | Whittier |
| 5,713,910 A | 2/1998 | Gordon et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,722,421 A | 3/1998 | Francese et al. |
| 5,741,280 A | 4/1998 | Fleenor |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,855,614 A | 1/1999 | Stevens et al. |
| 5,860,990 A | 1/1999 | Nobles et al. |
| 5,868,733 A | 2/1999 | Ockuly et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,947,363 A | 9/1999 | Bolduc et al. |
| 5,954,732 A | 9/1999 | Hart et al. |
| 5,972,030 A | 10/1999 | Garrison et al. |
| 5,980,455 A | 11/1999 | Daniel et al. |
| 5,989,284 A | 11/1999 | Laufer |
| 6,019,722 A | 2/2000 | Spence et al. |
| 6,033,378 A | 3/2000 | Lundquist et al. |
| 6,036,699 A | 3/2000 | Andreas et al. |
| 6,045,497 A | 4/2000 | Schweich et al. |
| 6,060,628 A | 5/2000 | Aoyama et al. |
| 6,060,629 A | 5/2000 | Pham et al. |
| 6,066,146 A | 5/2000 | Carroll et al. |
| 6,077,214 A | 6/2000 | Mortier et al. |
| 6,086,600 A | 7/2000 | Kortenbach |
| 6,117,144 A | 9/2000 | Nobles et al. |
| 6,123,699 A | 9/2000 | Webster, Jr. |
| 6,132,447 A | 10/2000 | Dorsey |
| 6,136,010 A | 10/2000 | Modesitt et al. |
| 6,143,024 A | 11/2000 | Campbell et al. |
| 6,162,233 A | 12/2000 | Williamson, IV et al. |
| 6,165,183 A | 12/2000 | Kuehn et al. |
| 6,187,003 B1 | 2/2001 | Buysse et al. |
| 6,190,408 B1 | 2/2001 | Melvin |
| 6,203,553 B1 | 3/2001 | Robertson et al. |
| 6,206,893 B1 | 3/2001 | Klein et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,269,819 B1 | 8/2001 | Oz et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,355,030 B1 | 3/2002 | Aldrich et al. |
| 6,368,326 B1 | 4/2002 | Dakin et al. |
| 6,402,781 B1 | 6/2002 | Langberg et al. |
| 6,406,420 B1 | 6/2002 | McCarthy et al. |
| 6,461,366 B1 | 10/2002 | Seguin |
| 6,464,707 B1 | 10/2002 | Bjerken |
| 6,482,224 B1 | 11/2002 | Michler et al. |
| 6,537,314 B2 | 3/2003 | Langberg et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |

| | | |
|---|---|---|
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,826 B2 | 3/2004 | Liddicoat et al. |
| 6,709,382 B1 | 3/2004 | Horner |
| 6,709,456 B2 | 3/2004 | Langberg et al. |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,875,224 B2 | 4/2005 | Grimes |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,011,669 B2 | 3/2006 | Kimblad |
| 7,048,754 B2 | 5/2006 | Martin et al. |
| 7,112,207 B2 | 9/2006 | Allen et al. |
| 7,226,467 B2 | 6/2007 | Lucatero et al. |
| 7,563,267 B2 * | 7/2009 | Goldfarb et al. ............... 606/151 |
| 7,704,269 B2 | 4/2010 | St. Goar et al. |
| 2001/0037084 A1 | 11/2001 | Nardeo |
| 2002/0013571 A1 | 1/2002 | Goldfarb et al. |
| 2002/0035361 A1 | 3/2002 | Houser et al. |
| 2002/0087148 A1 | 7/2002 | Brock et al. |
| 2002/0087169 A1 | 7/2002 | Brock et al. |
| 2002/0156526 A1 | 10/2002 | Hlavka et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183835 A1 | 12/2002 | Taylor et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0105519 A1 | 6/2003 | Fasol et al. |
| 2003/0120341 A1 | 6/2003 | Shennib et al. |
| 2003/0130730 A1 | 7/2003 | Cohn et al. |
| 2003/0167071 A1 | 9/2003 | Martin et al. |
| 2003/0187467 A1 | 10/2003 | Schreck |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thornton et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goar et al. |
| 2005/0021057 A1 | 1/2005 | St. Goar et al. |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2006/0004247 A1 | 1/2006 | Kute et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0195012 A1 | 8/2006 | Mortier et al. |
| 2006/0229708 A1 | 10/2006 | Powell et al. |
| 2006/0241745 A1 * | 10/2006 | Solem ............................ 623/2.18 |
| 2006/0252984 A1 | 11/2006 | Rahdert et al. |
| 2007/0038293 A1 | 2/2007 | St.Goar et al. |
| 2007/0198082 A1 | 8/2007 | Kapadia et al. |
| 2008/0039935 A1 | 2/2008 | Buch et al. |
| 2008/0125860 A1 * | 5/2008 | Webler et al. ................ 623/2.36 |
| 2008/0125861 A1 * | 5/2008 | Webler et al. ................ 623/2.36 |
| 2008/0319541 A1 | 12/2008 | Filsoufi |
| 2009/0043382 A1 | 2/2009 | Maurer et al. |
| 2009/0149949 A1 | 6/2009 | Quinn |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2010/0100108 A1 * | 4/2010 | Goldfarb et al. ............... 606/151 |
| 2010/0185276 A1 * | 7/2010 | Vidlund et al. ............... 623/2.11 |
| 2010/0318184 A1 * | 12/2010 | Spence ........................... 623/2.36 |
| 2011/0077733 A1 * | 3/2011 | Solem ............................ 623/2.12 |
| 2011/0224784 A1 * | 9/2011 | Quinn ............................ 623/2.11 |

| | 2012/0078358 | A1* | 3/2012 | Vidlund et al. ............... 623/2.36 |

FOREIGN PATENT DOCUMENTS

| EP | 684012 | 2/1995 |
|---|---|---|
| EP | 0727239 | 8/1996 |
| EP | 1674040 | 6/2006 |
| FR | 2768324 | 3/1999 |
| GB | 1598111 | 9/1981 |
| GB | 2151142 | 7/1985 |
| JP | 11089937 | 6/1999 |
| WO | 81/00668 | 3/1981 |
| WO | 91/01689 | 2/1991 |
| WO | 92/12690 | 8/1992 |
| WO | 91/18881 | 9/1994 |
| WO | 94/18881 | 9/1994 |
| WO | 94/18893 | 9/1994 |
| WO | 97/39688 | 10/1997 |
| WO | 98/07375 | 2/1998 |
| WO | 98/24372 | 6/1998 |
| WO | 98/30153 | 7/1998 |
| WO | 98/35638 | 8/1998 |
| WO | 99/00059 | 1/1999 |
| WO | 99/01377 | 1/1999 |
| WO | 99/07354 | 2/1999 |
| WO | 00/03759 | 1/2000 |
| WO | 00/59382 | 10/2000 |
| WO | 00/60995 | 10/2000 |
| WO | 01/26557 | 4/2001 |
| WO | 01/26586 | 4/2001 |
| WO | 01/28432 | 4/2001 |
| WO | 01/54618 | 8/2001 |
| WO | 02/03892 | 1/2002 |
| WO | 03/001893 | 1/2003 |
| WO | 03/03930 | 1/2003 |
| WO | 03/020179 | 3/2003 |
| WO | 03/028558 | 4/2003 |
| WO | 03/037171 | 5/2003 |
| WO | 03/047467 | 6/2003 |
| WO | 03/049619 | 6/2003 |
| WO | 03/073913 | 9/2003 |
| WO | 03/105667 | 12/2003 |
| WO | 2004/004607 | 1/2004 |
| WO | 2004/012583 | 2/2004 |
| WO | 2004/012789 | 2/2004 |
| WO | 2004/019811 | 3/2004 |
| WO | 2004/030570 | 4/2004 |
| WO | 2004/082538 | 4/2004 |
| WO | 2004/037317 | 5/2004 |
| WO | 2004/045370 | 6/2004 |
| WO | 2004/045378 | 6/2004 |
| WO | 2004/045463 | 6/2004 |
| WO | 2004/047679 | 6/2004 |
| WO | 2004/062725 | 7/2004 |
| WO | 2004/082523 | 9/2004 |
| WO | 2004/093730 | 11/2004 |
| WO | 2004/112585 | 12/2004 |
| WO | 2004/112651 | 12/2004 |
| WO | 2005/002424 | 1/2005 |
| WO | 2005/018507 | 3/2005 |
| WO | 2005/027797 | 3/2005 |
| WO | 2005/032421 | 4/2005 |
| WO | 2005/062931 | 7/2005 |
| WO | 2005/112792 | 12/2005 |
| WO | 2006/086434 | 8/2006 |
| WO | 2006/105008 | 10/2006 |
| WO | 2006/105009 | 10/2006 |
| WO | 2006/115875 | 11/2006 |
| WO | 2006/115876 | 11/2006 |
| WO | 2006/116558 | 11/2006 |
| WO | 2006/127509 | 11/2006 |
| WO | 2008/141322 | 11/2008 |
| WO | 2009/064998 | 5/2009 |
| WO | 2009/072114 | 6/2009 |

OTHER PUBLICATIONS

Abe et al., "Updated: De Vega's annuloplasty for acquired tricuspid disease: Early and late results in 110 patients" Ann. Thorac. Surg. (1996) 62:1876-1877.

Agricola et al., "Mitrel valve reserve in double orifice technique: an exercise echocardiographic study," Journal of Heart Valve Disease 11(5): 637-643 (2002).

Alfieri et al., "An effective technique to correct anterior mitral leaflet prolapse," J. Card. Surg. 14(6): 468-470 (1999).

Alfieri et al, "Novel suture device for beating heart mitral leaflet approximation," Annals of Thoracic Surgery 74: 1488-1493 (2002).

Alfieri et al., "The double orifice technique in mitral valve repair: a simple solution for complex problems," Journal of Thoracic Cardiovascular Surgery 122: 674-681 (2001).

Alfieri, O., "Surgical Treatment of Atrial Fibrillation: Summary of Current Experience," The edge-to-edge repair of the mitral valve, [Abstract] 6th Annual New Era Cardiac Care: Innovation & Technology, Heart Surgery Forum, pp. 103 (2003).

Alvarez et al, "Repairing the Degenerative Mitral Valve: Ten- to Fifteen-Year Follow-up," J. Thorac. Cardiovasc. Surg. 112:238-247 (1996).

Arisi et al., "Mitral valve repair with Alfieri technique in mitral regurgitation of diverse etiology: early echocardiographic results," Circulation Supplement II, 104: 3240 (2001).

Bach and Bolling et al., "Early improvement in congestive heart failure after correction of secondary mitral regurgitation in end-stage cardiomyopathy," Am. Heart J. 129:1165-1170 (1995).

Bach and Bolling et al., "Improvement following correction of secondary mitral regurgitation in end-stage cardiomyopathy with mitral annuloplasty," Am. J. Cardiol. 78:966-969 (1996).

Bailey, "Mitral Regurgitation," in Surgery of the Heart Chapter 20 (1995) pp. 686-737.

Bernal et al., "The 'Valve Racket': a new and different concept of atrioventricular valve repair," European Journal of Cardio-thoracic Surgery 29:1026-29 (2006).

Bhudia, S., "Edge-to-edge mitral repair: a versatile mitral repair technique," The Cleveland Clinic Foundation, Cleveland, Ohio, www.ctsnet.org/doc/7007 (accessed on Dec. 14, 2004).

Bolling et al., "Surgery for acquired heart disease" (1995) 109:676-683.

Borghetti et al., "Preliminary observations on haemodynamics during physiological stress conditions following 'double-orifice' mitral valve repair," European Journal of Cardiothoracic Surgery 20: 262-269 (2001).

Castedo, "Edge-to-edge tricuspid repair for redeveloped valve incompetence after DeVega's annuloplasty," Ann Thora Surg. 75: 605-606 (2003).

Dec and Fuster et al., "Idiopathic dilated cardiomyopathy," N. Engl. J. Med. 331:1564-1575 (1994).

Derwent citing French language patent, FR2768324 published Mar. 19, 1999, for: "Surgical instrument for joining soft tissues through percutaneous access" WPI Acc No. 1999-231954/199920.

Derwent citing German language patent, EP 684012 published Nov. 12, 1995, for: "Thread for constructing surgical seam- has flexible section with two ends, with lower fastening part on thread first end having hollow cylinder with continuous hole through which surgical needle threads".

Derwent citing Japanese language patent, JP 11089937 published Jun. 4, 1999, for: "Catheter for mitral regurgitation test- includes jet nozzles provided on rear side of large diametered spindle shaped portion attached to end of narrow diametered tube".

Dottori et al., "Echocardiographic imaging of the Alfieri type mitral valve repair," Ital. Heart J. 2(4): 319-320 (2001).

Downing et al., "Beating heart mitral valve surgery: preliminary model and methodology," Journal of Thoracic and Cardiovascular surgery 123(6): 1141-1146 (2002).

Falk et al., "Computer-enhanced mitral valve surgery: toward a total endoscopic procedure," Seminars in thoracic and cardiovascular surgery 11(3): 224-249 (1999).

Filsoufi et al., "Restoring Optimal Surface of Coaptation With a Mini Leaflet Prosthesis: A New Surgical Concept for the Correction of Mitral Valve Prolapse," Intl Soc. For Minimally Invasive Cardiothoracic Surgery 1(4):186-87 (2006).

Fucci et al., "Improved results with mitral valve repair using new surgical techniques" Eur. J. Cardiothorac. Surg. (1995) 9:621-627.

Fundaro et al., "Chordal Plication and free edge remodeling for mitral anterior leaflet prolapse repair: 8 year follow-up," Annals of Thoracic Surgery 72: 1515-1519 (2001).

G. Noera et al "Tricuspid Valve Incompetence Caused by Nonpenetrating Thoracic Trauma", Annals of Thoracic Surgery 51(2) (1991) p. 320-22.

Garcia-Rinaldi et al., "Left ventricular volume reduction and reconstruction is ischemic cardiomyopathy," Journal of Cardiac Surgery 14: 199-210 (1999).

Gateliene, "Early and postoperative results results of metal and tricuspid valve insufficiency surgical treatment using edge-to-edge central coaptation procedure," Medicina 38 (Suppl 2): 172-175 (2002) [Article in Lithuanian, English summary on p. 174 of the article].

Gatti et al., "The edge to edge technique as a trick as a trick to rescue an imperfect mitral valve repair," Eur. J. Cardiothorac Surg 22(5): 817-20 (2002).

Gillinov et al., "Is minimally invasive heart valve surgery a paradigm for future?" Current Cardiology Reports 1: 318-322 (1999).

Gundry et al., "Facile Minimally Invasive Cardiac Surgery via Ministernotomy," Ann. Thorac. Surg. 65: 1100-1104 (1998).

Ikeda et al., "Batista's operation with coronary artery bypass grafting and mitral valve plasty for ischemic dilated cardiomyopathy," The Japanese Journal of Thoracic and Cardiovascular Surgery 48: 746-749 (2000).

Izzat et al., "Early experience with partial left ventriculectomy in the Asia-Pacific Region," Annuals of Thoracic Surgery 67: 1703-1707 (1999).

Kallner et al., "Transaortic approach for the Alfieri Stitch," Ann Thorac Surg 71: 378-380 (2001).

Kameda et al., Annuloplasty for severe mitral regurgitation due to dilated cardiomyopathy Am. Thorac. Surg. (1996) 61:1829-1832.

Kavarana et al., "Transaortic repair of mitral regurgitation," Presented at the third annual New Era Cardiac Care conference, San Diego, CA, Jan. 13-16 (2000), 1.:1://www.hsforum.com/vol3/issue1/2000-2389print.html (accessed on Dec. 14, 2004).

Kaza et al., "Ventricular reconstruction results in improved left ventricular function and amelioration of mitral insufficiency," Annals of Surgery 235(6): 828-832 (2002).

Khan et al. "Blade atrial septostomy: Experience with the first 50 procedures" Cathet. Cardiovasc. Diagn. (1991) 23: 257-262.

Kherani, "The edge-to-edge mitral valve repair: the Columbia Presbyterian experience," Ann. Thorac. Surg. 78: 73-76 (2004).

Konertz et al., "Results after partial left venticulectomy in a European heart failure population," Journal of Cardiac Surgery 14(2): 129-135 (1999).

Kron et al., "Surgical relocation of the posterior papillary muscle in chronic ischemic metal regurgitation," Annals. of Thoracic Surgery 74: 600-601 (2002).

Kruger et al., "Edge to edge technique in complex mitral valve repair," Thorac Cardiovasc Surg. 48 (Supplement I): p. 106 (abstract p73) (2000).

Langer et al., "Posterier mitral leaflet extensions: An adjunctive repair option for ischemic mitral regurgitation?," J Thorac Cardiovasc Surg 131:868-77 (2006).

Lorusso et al., "'Double-Orifice' technique to repair extensive mitral valve excision following acute endocarditis," J. Card Surg 13: 24-26 (1998).

Lorusso et al., "The double-orifice technique for mitral valve reconstruction: predictors of postoperative outcome," Eur J. Cardiothorac Surg 20(3): 583-589 (2001).

Maisano et al., "The double orifice repair for Barlow Disease: a simple solution for a complex repair," Circulation (Supplement 1) 100(18): 1-94 (1989).

Maisano at al., "The double orifice technique as a standardized approach to treat mitral regurgitation due to severe myxomatous disease: surgical technique," European Journal of Cardiothoracic Surgery 17: 201-205 (2000).

Maisano at al., "The edge-to-edge technique: A simplified method to correct mitral insufficiency" Eur. J. Cardiothorac. Surg. (1998) 13:240-246.

Maisano et al., "The hemodynamic effects of double-orifice valve repair for mitral regurgitation: a 3D computational model: a 3D computational model," European Journal of Cardio-thoracic Surgery 15: 419-425 (1999).

Maisano et al., "Valve repair for traumatic tricuspid regurgitation," Eur. J. Cardio-thorac Surg 10: 867-873 (1996).

Mantovani et al., "Edge-to-edge repair of congenital familiar tricuspid regurgitation: case report," J. Heart Valve Dis., 9(5): 641-643 (2000).

McCarthy and Cosgrove et al., "Tricuspid Valve Reapir with the Cosgrove- Edwards Annuloplasty System," Ann. Thorac. Surg. 64:267-268 (1997).

McCarthy et al., "Partial left ventriculectomy and mitral valve repair for end-stage congestive heart failure," European Journal of Cardiothoracic Surgery 13: 337-343 (1998).

Moainie et al., "Correction of traumatic tricuspid regurgitation using the double orifice technique, " Annals of Thoracic Surgery 73: 963-965 (2002).

Morales et al., "Development of an off bypass mitral valve repair," The Heart Surgery Fourm #1999-4693, 2(2): 115-120 (1999).

Nakanishi et al., "Early outcome with the Alfieri mitral valve repair," J. Cardiol. 37(5): 263-266 (2001) [Abstract in English; Article in Japanese].

Nielsen et al., "The edge-to-edge mitral repair: tension of the approximating suture and leaflet deformation during acute ischemic mitral regurgitation in the ovine heart," Circulation 104(Suppl 1): 1-29-1-35 (2001).

Noera et al "Tricuspid Valve Incompetence Caused by Nonpenetrating Thoracic Trauma", Annals of Thoracic Surgery 51(2) (1991) p. 320-22.

Osawa et al., "Partial left ventriculectomy in a 3 year old boy with dilated cardiomyopathy," Japanese Journal of Thoracic and Cardiovascular Surgery 48(9): 590-593 (2000).

Park et al., "Clinical use of a blade atrial septostomy" Circulation (1978) 58:600-608.

Privitera et al., "Alfieri Mitral Valve Repair: Clinical Outcome and Pathology," Circulation 106: 173 (2002).

Redaelli et al., "A computational study of the hemodynamics after 'edge-to-edge' mitral valve repair," Journal of Biomechanical Engineering 123: 565-570 (2001).

Reul, R.M. and L. H. Cohn II, "Mitral valve reconstruction for mitral insufficiency," Progress in Cardiovascular Diseases, 39(6):567-599, (1997).

Ricchi et al., Linear segmental annuloplasty for mitral valve repair Ann. Thorac. Surg. (1997) 63:1805-1806.

Tager et al., "Long-term follow-up of rheumatic patients undergoing left-sided valve replacement with tricuspid annuloplasty—validity of preoperative echocardiographic criteria in the decision to perform tricuspid annuloplasty," Am. J. Cardiol. 81:1013-1016 (1998).

Tamura et al., "Edge to edge repair for mital regurgitation on a patient with chronic hemodialysis: report of a case," Kyobu Geka 54(9): 788-790 (2001) [Article in Japanese, English Summary].

Timek, "Edge-to-edge mitral repair: gradients and three-dimensional annular dynamics in vivo during inotropic stimulation," European Journal of Cardio-thoracic Surgery 19: 431-437 (2001).

Timek, "Edge-to-edge mitral valve repair without ring annuloplasty for acute ischemic mitral regurgitation," Circulation 108 (Supplement II): II-122-11-127 (2003).

Totaro, "Mitral valve repair for isolated prolapse of the anterior leaflet: an 11-year followup," European Journal of Cardio-thoracic Surgery 15: 119-126 (1999).

Uchida et al., "Percutaneous cardiomyotomy and valvulotomy with angioscopic guidance," Am. Heart J. 121:1221-1224 (1991).

Umana at al., "'Bow-tie' mitral valve repair successfully addresses subvalvular dysfunction in ischemic mitral regurgitation," Surgical Forum, 48: 279-280 (1997).

Umana et al., "Bow-tie' mitral valve repair: An Adjuvant technique for ischemic regurgitation" Ann. Thorac. Surg. (1998) 66:1640-1646.

Votta et al., "3-D computational analysis of the stress distribution on the leaflets after edge-to-edge repair of mitral regurgitation," Journal of Heart Valve Disease 11: 810-822 (2002).

* cited by examiner

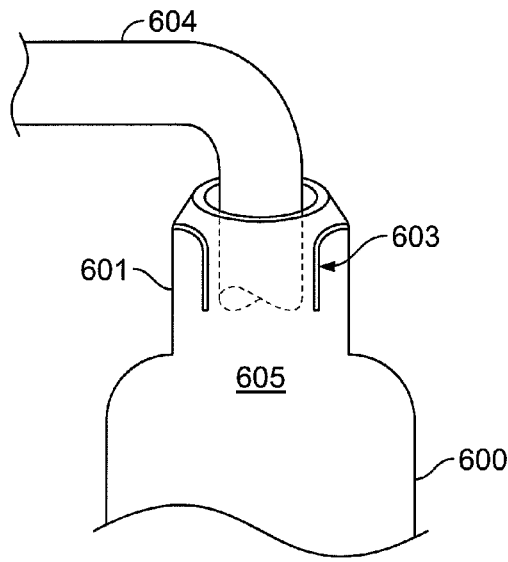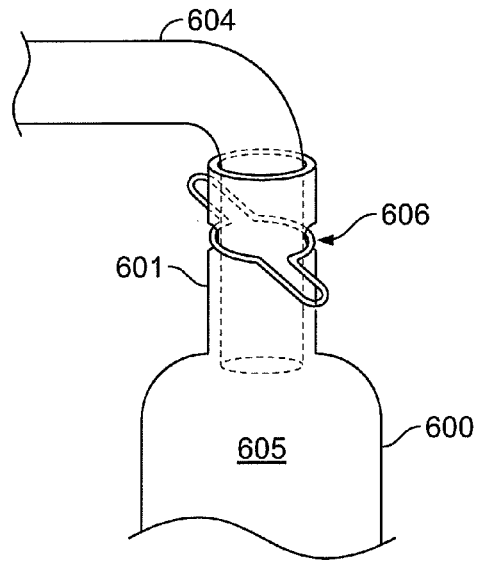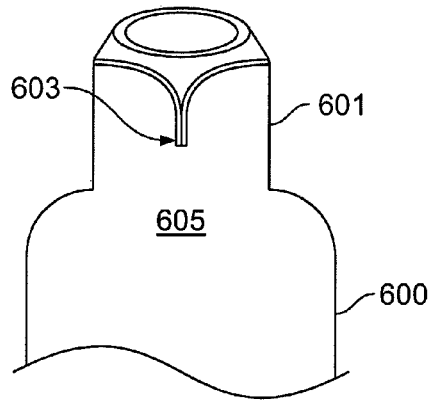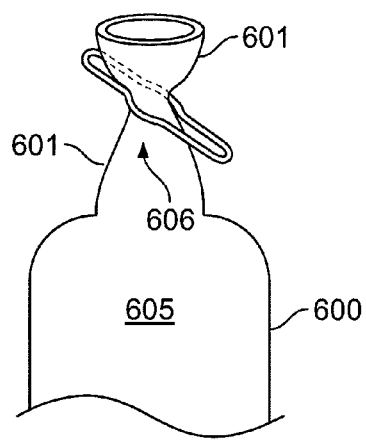
FIG. 10A
FIG. 10C
FIG. 10B
FIG. 10D

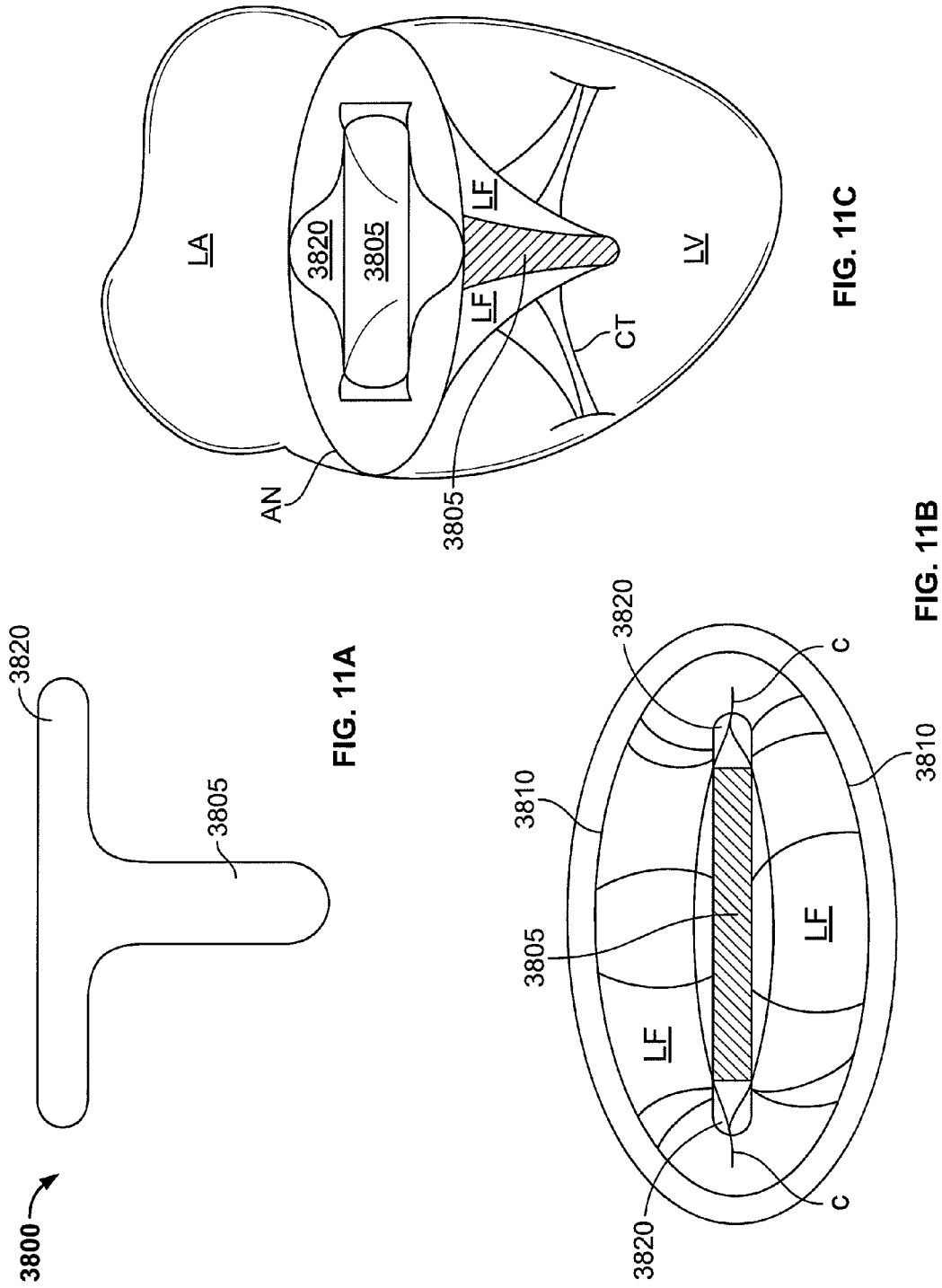

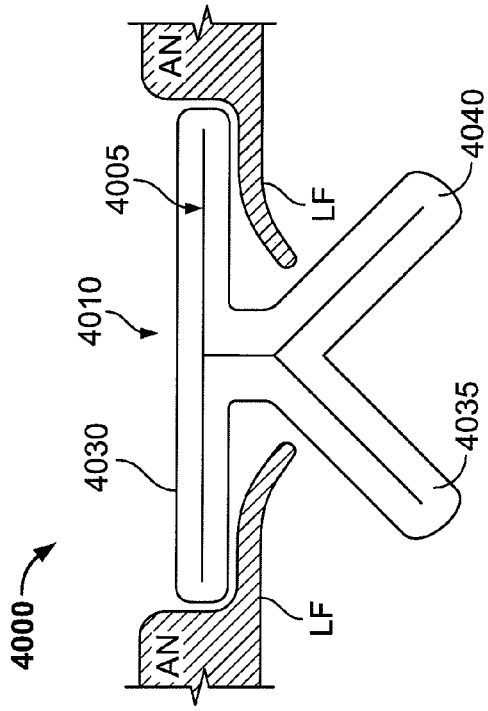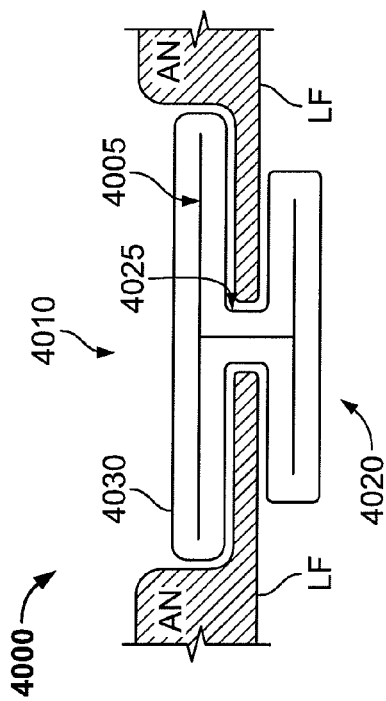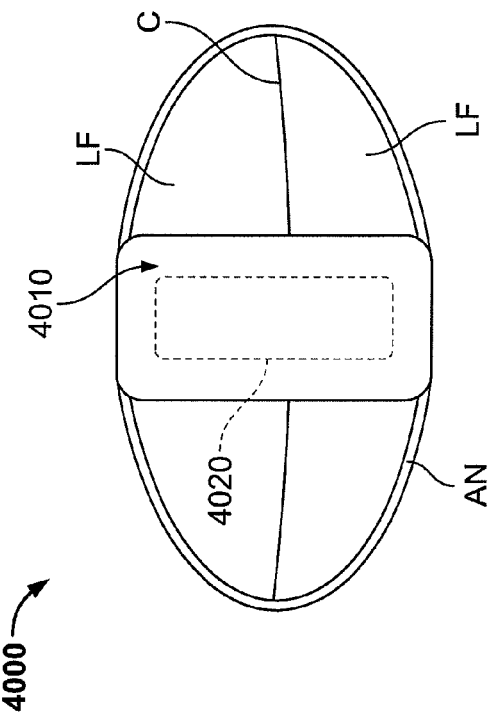
FIG. 12A
FIG. 12B
FIG. 12C

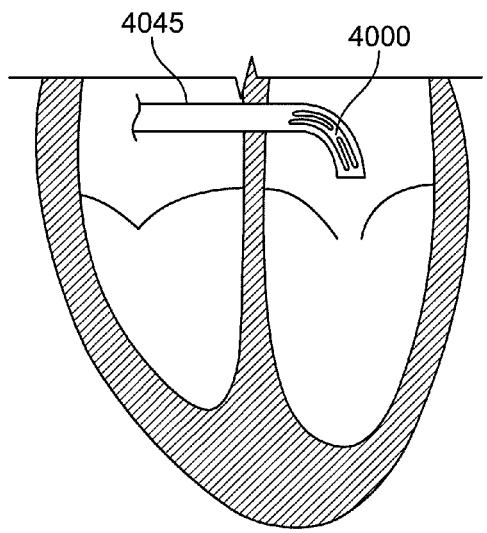
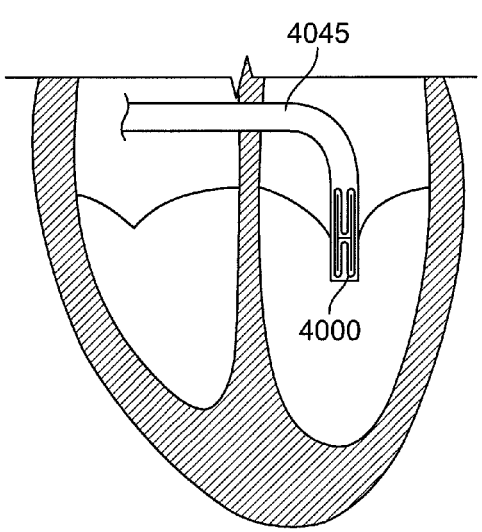
FIG. 12D  FIG. 12E
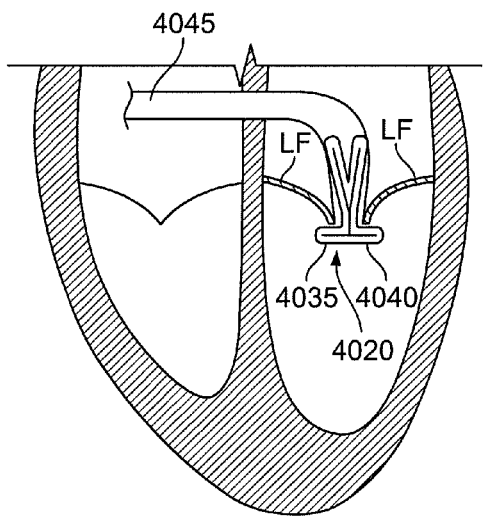
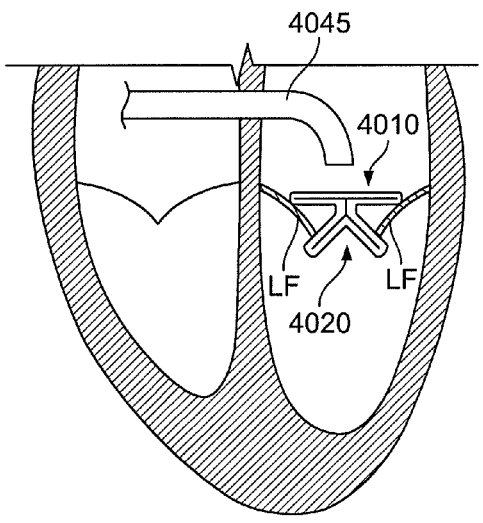
FIG. 12F  FIG. 12G

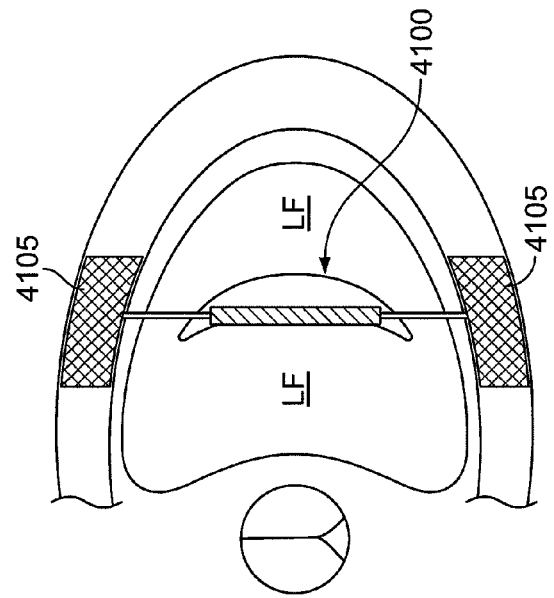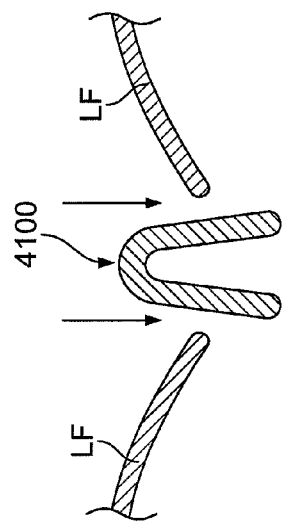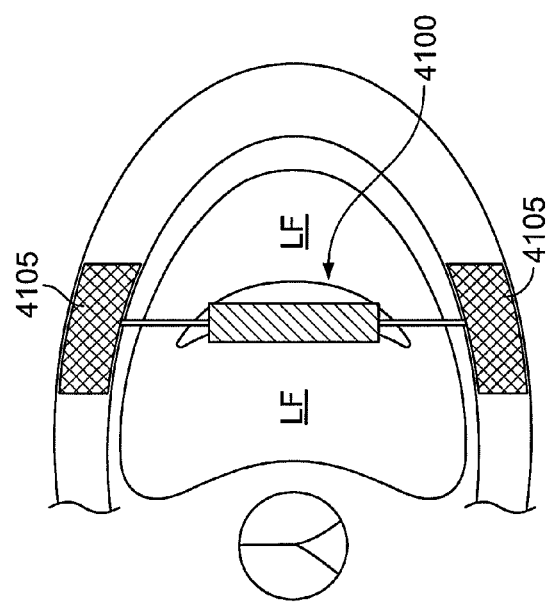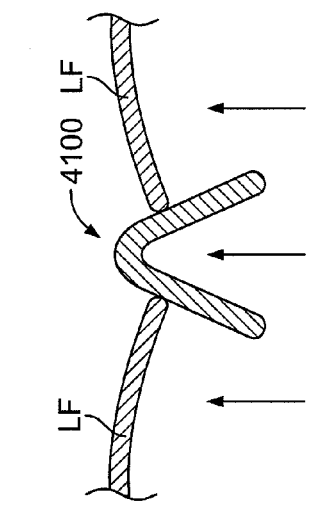

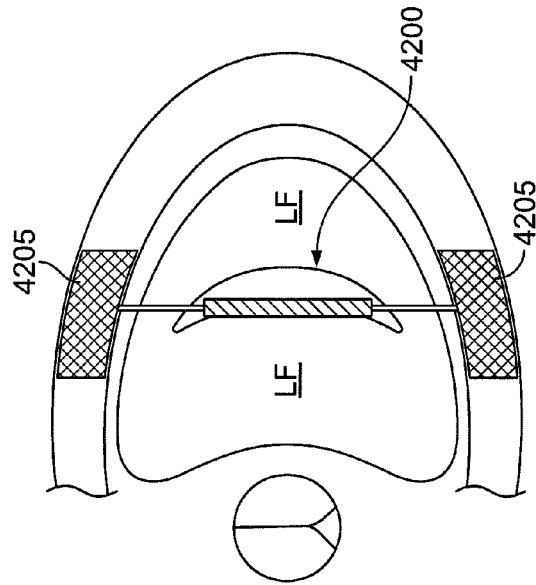
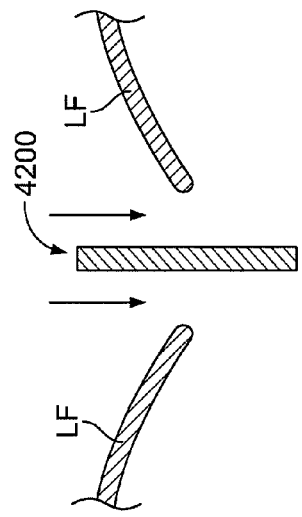
FIG. 14B
FIG. 14D
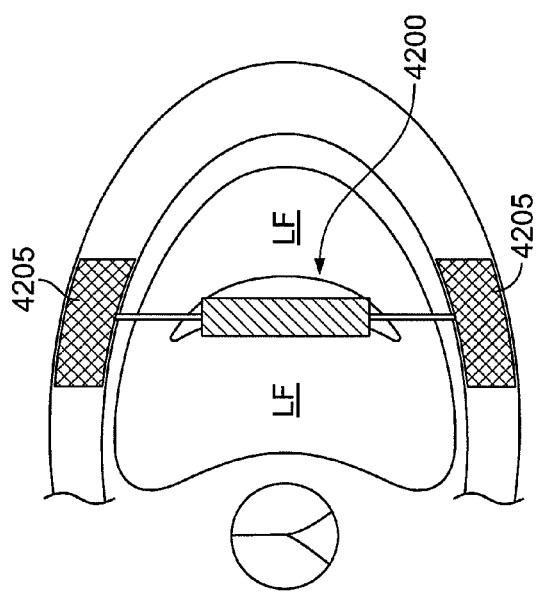
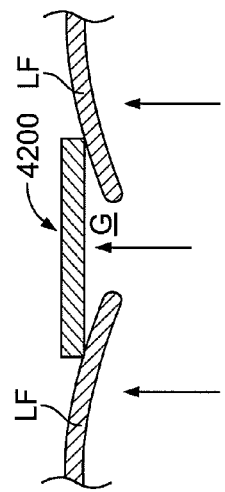
FIG. 14A
FIG. 14C

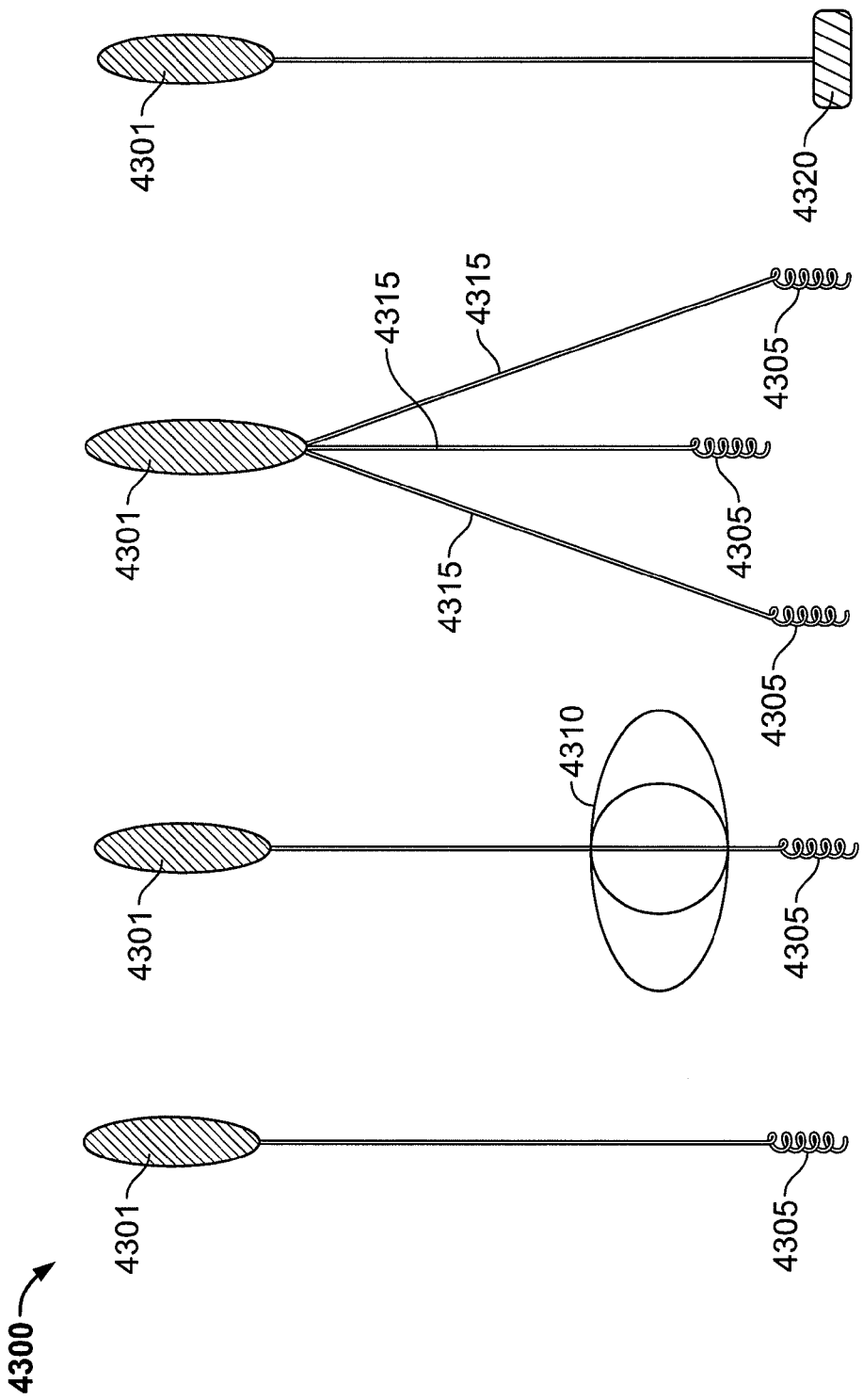

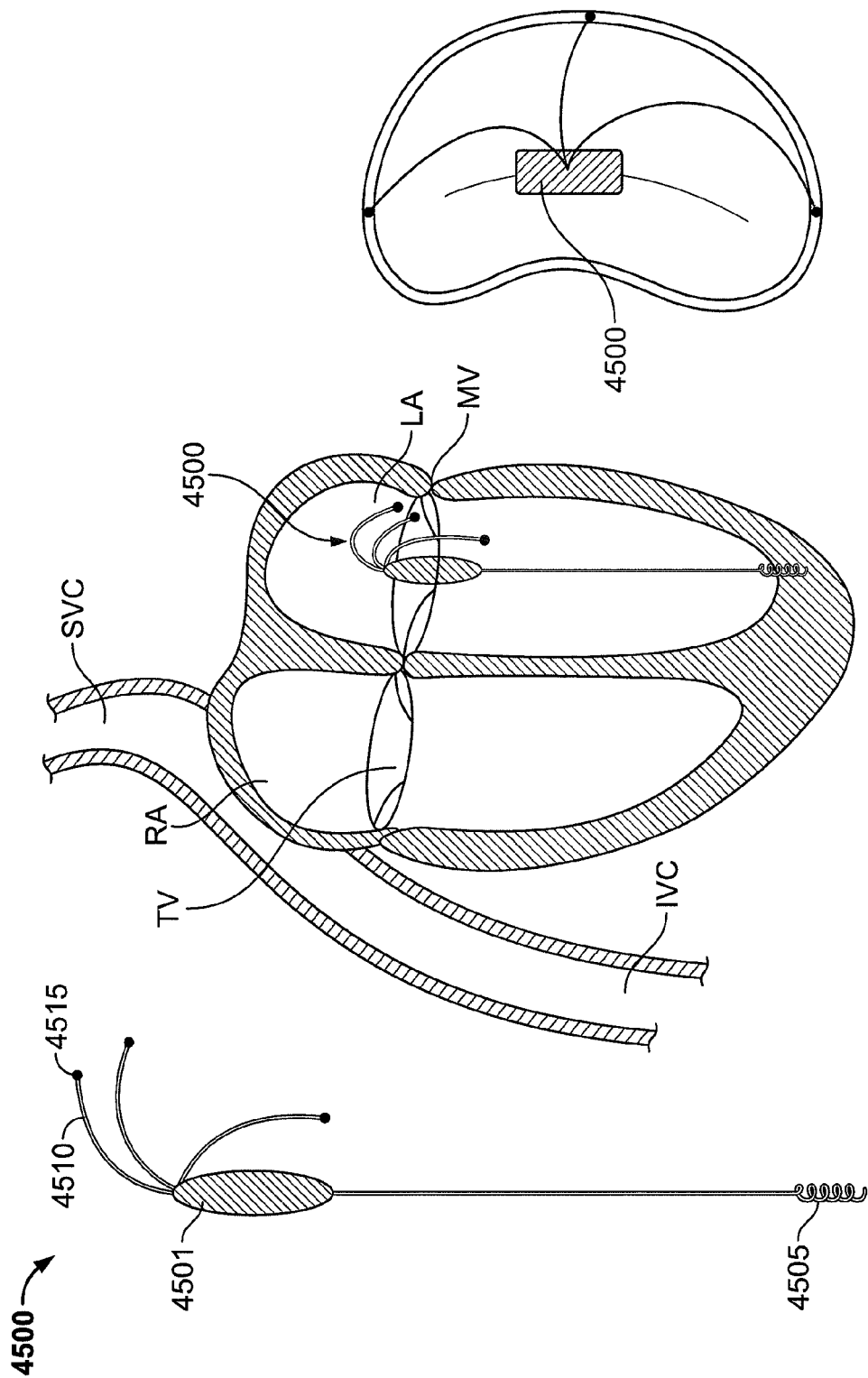

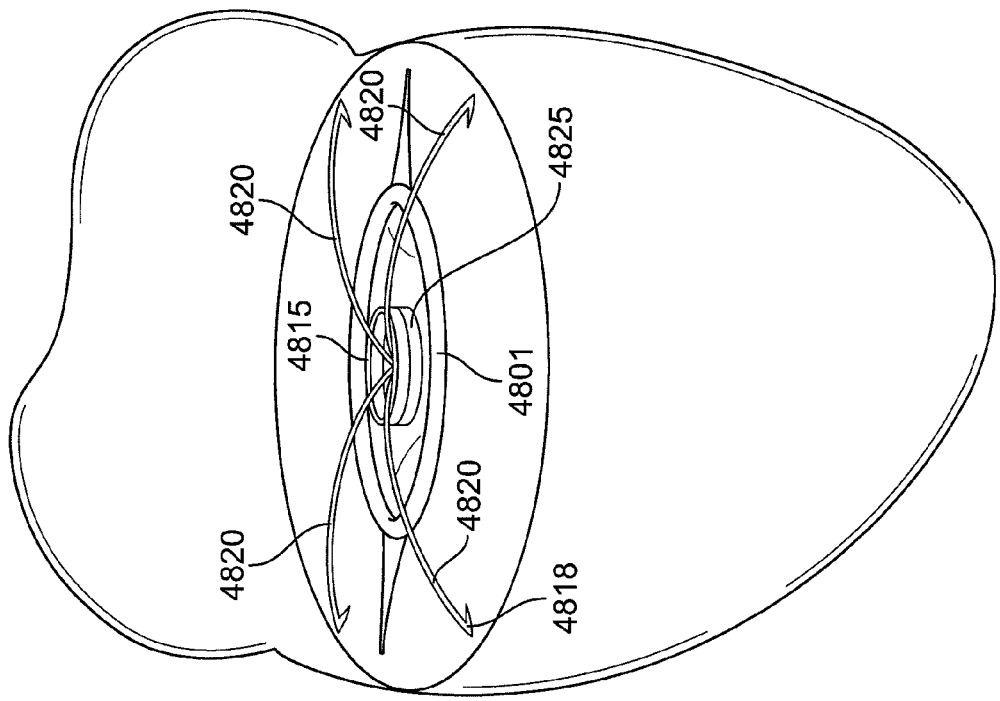
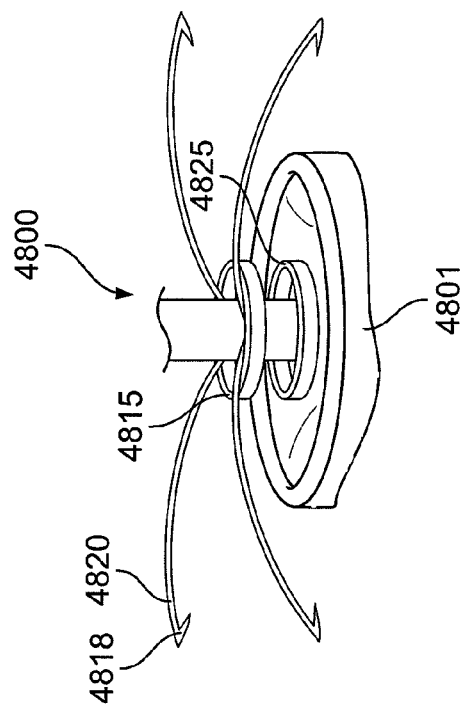
FIG. 19C
FIG. 19B

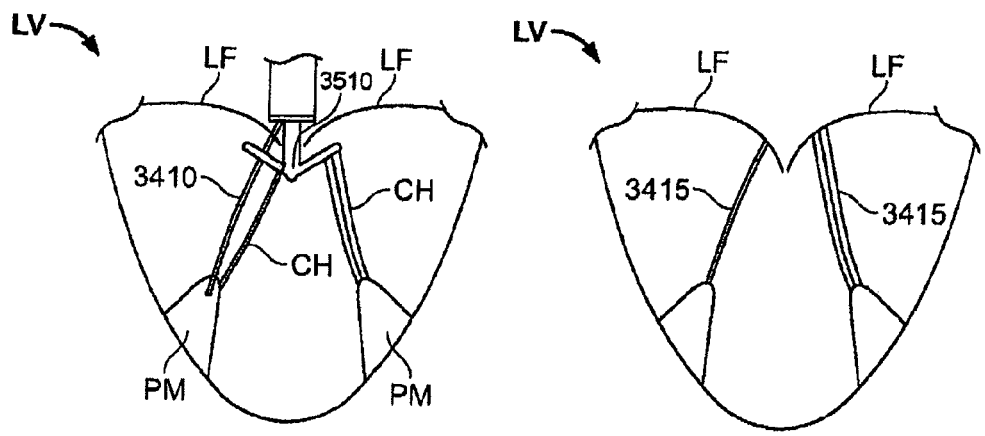
FIG. 46
FIG. 47
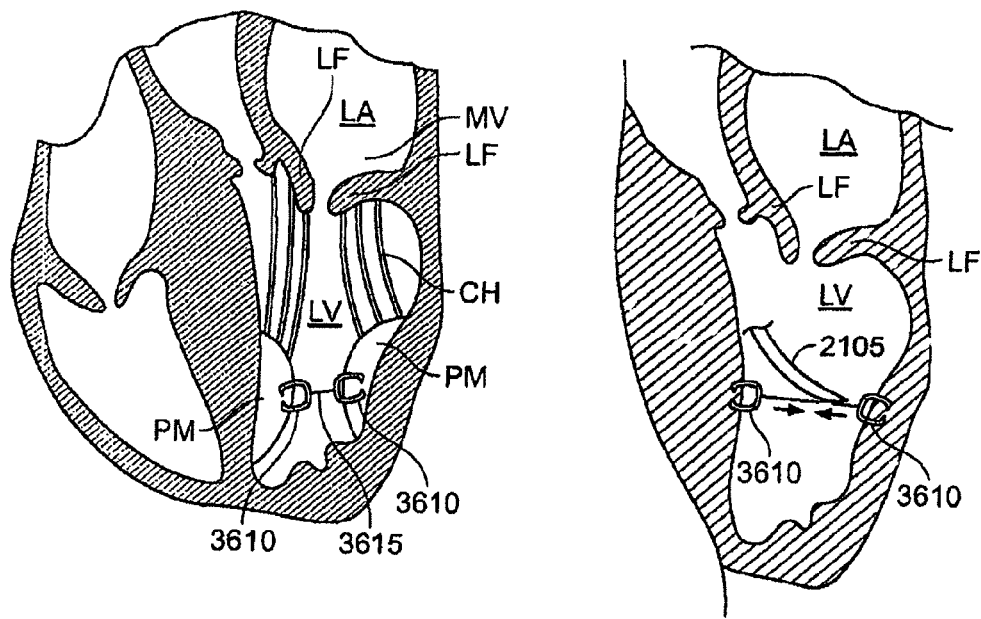
FIG. 48
FIG. 49

METHODS, SYSTEMS AND DEVICES FOR CARDIAC VALVE REPAIR

RELATED TO PRIORITY DOCUMENTS

This application claims the benefit of priority under 35 U.S.C. §119(e) of U.S. Provisional Application Ser. No. 61/242,506, filed Sep. 15, 2009. Priority of the aforementioned filing date is hereby claimed, and the subject matter of the above-noted application is hereby incorporated by reference in its entirety by reference thereto.

This application is also related to co-pending U.S. application Ser. No. 12/690,027, filed on the same day herewith, entitled "Methods, Systems and Devices for Cardiac Valve Repair," which is a continuation-in-part of U.S. application Ser. No. 11/349,742, filed Feb. 7, 2006, which claims priority of U.S. Provisional Patent Application Ser. No. 60/650,918, filed Feb. 7, 2005 and U.S. Provisional Patent Application Ser. No. 60/692,802, filed Jun. 21, 2005 and which also claims the benefit of priority under 35 U.S.C. §119(e) of U.S. Provisional Application Ser. No. 61/242,506, filed Sep. 15, 2009.

BACKGROUND

The present invention relates generally to medical methods, devices, and systems. In particular, the present invention relates to methods, devices, and systems for the endovascular or minimally invasive surgical repair of the atrioventricular valves of the heart, particularly the mitral valve.

Mitral valve regurgitation is characterized by retrograde flow during systole from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve. The valve leaflets, the valve chordae which connect the leaflets to the papillary muscles, or the papillary muscles themselves may be damaged or otherwise dysfunctional. Commonly, the valve annulus may be damaged, dilated, or weakened limiting the ability of the mitral valve to close adequately against the high pressures of the left ventricle. In some cases the mitral valve leaflets detach from the chordae tendinae, the structure that tethers them to the ventricular wall so that they are positioned to coapt or close against the other valve leaflet during systole. In this case, the leaflet "flails" or billows into the left atrium during systole instead of coapting or sealing against the neighboring leaflet allowing blood from the ventricle to surge into the left atrium during systole. In addition, mitral valve disease can include functional mitral valve disease which is usually characterized by the failure of the mitral valve leaflets to coapt due to an enlarged ventricle, or other impediment to the leaflets rising up far enough toward each other to close the gap or seal against each other during systole.

The most common treatments for mitral valve regurgitation rely on valve replacement or strengthening of the valve annulus by implanting a mechanical support ring or other structure. The latter is generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated morbidity.

SUMMARY

For the foregoing reasons, it would be desirable to provide alternative and additional methods, devices, and systems for performing the repair of mitral and other cardiac valves, including the tricuspid valve, which is the other atrioventricular valve. In some embodiments of the present invention, methods and devices may be deployed directly into the heart chambers via a trans-thoracic approach, utilizing a small incision in the chest wall, or the placement of a cannula or a port. In other embodiments, such methods, devices, and systems may not require open chest access and be capable of being performed endovascularly, i.e., using devices which are advanced to the heart from a point in the patient's vasculature remote from the heart. In other embodiments, the methods, devices, and systems should not require that the heart be bypassed, although the methods, devices, and systems should be useful with patients who are bypassed and/or whose heart may be temporarily stopped by drugs or other techniques. At least some of these objectives will be met by the inventions described hereinbelow.

In one aspect, there is disclosed a device for treating regurgitation through a valve in a heart, the heart having an atrium fluidically coupled to a ventricle by the valve, the valve including at least two leaflets which coapt along a line of coaptation, the device including an expandable, fluid-tight bladder configured to be deployed between valve leaflets of the heart valve. The bladder includes an upper portion that extends into the atrium of the heart; a middle portion positionable within the line of valve leaflet coaptation. The middle portion provides a sealing surface for one or more of the leaflets. The bladder also includes a lower portion that extends into the ventricle of the heart. The upper portion and lower portions expand and contract passively upon changes in heart chamber pressure differential. The bladder also includes a proximal anchoring mechanism having at least one pair of angled clamping wires coupled to and extending proximally from a proximal end region of the bladder; and a sliding sleeve having an inner diameter that is smaller than an outer diameter of the bladder in an expanded configuration. The pair of angled clamping wires extend through the inner diameter of the sliding sleeve.

The device can also include an upper portion of the bladder that blocks a valve leaflet from flailing into the atrium. The bladder can be fluid-filled. The bladder can further include one or more anchors securing the bladder to a location in the heart that is distal to an annulus of the valve. The one or more anchors can also secure the bladder to an annulus of the valve. The one or more anchors can secure the middle portion in a stationary position to the annulus of the valve. Expansion of the bladder can move the sliding sleeve in a proximal direction and the inner diameter of the sliding sleeve urges the pair of angled clamping wires towards one another. The pair of angled clamping wires can removably capture at least a portion of the atrial wall between them. The expandable bladder can further include a valve for selectively filling and depleting filling material into and out of the bladder such that the device can be repositioned, redeployed and removed.

In another aspect, there is disclosed a device for treating regurgitation through a gap in a valve in a heart that includes a frame sized to fit within a heart chamber; a pair of arms moveably coupled to the frame, the arms being moveable between a fluid flow-blocking position during systole into a fluid flow-allowing position during diastole; an anchoring mechanism having a tether and an expandable portion positioned in the coronary sinus, wherein the tether interconnects the frame to the expandable portion; and a compliant membrane covering the frame and at least a portion of the pair of arms.

The pair of arms can be coupled to the frame by a hinge. The frame can further include a stationary portion coupled to a proximal portion of the pair of arms. The stationary portion can be positioned above the level of the annulus. The stationary portion can have a long axis oriented orthogonal to the line of coaptation. The tether can connect to a region of the stationary portion near an outer edge of the gap. The long axis of the stationary portion can have a length sufficient to contact an anterior and posterior annulus. The device can be repositioned, redeployed and removed from the heart.

In another aspect, there is disclosed a device for treating regurgitation that includes a frame sized to fit within a heart chamber; a pair of arms moveably coupled to the frame, the arms being moveable between a fluid flow-blocking position during systole into a fluid flow-allowing position during diastole; an anchoring mechanism having a tether and an anchor positioned in a wall of the ventricle, wherein the tether interconnects the frame to the anchor; and a compliant membrane covering the frame and at least a portion of the pair of arms.

The pair of arms can be coupled to the frame by a hinge. The frame can further include a stationary portion coupled to a proximal portion of the pair of arms. The stationary portion can be positioned above the level of the annulus and have a long axis oriented orthogonal to the line of coaptation. The tether can connect to the frame at a lower surface of the stationary portion. The long axis of the stationary portion can have a length sufficient to contact an anterior and posterior annulus. The device can be repositioned in the heart, redeployed in the heart and removed from the heart.

In another aspect, disclosed in a method for treating regurgitation through a valve in a heart. The method includes introducing percutaneously a medical device system having a steerable guide catheter configured for delivery through the patient's vasculature to the vicinity of the gap; a retractable sheath moveably disposed over a blocker comprising an expandable, fluid-tight bladder, wherein the blocker is configured to be compressed by the sheath into a delivery configuration into a patient's heart to a vicinity of a gap within the line of coaptation of the valve. The method also includes using the guide catheter to position a middle portion of the blocker within the gap along the line of coaptation, an upper portion of the blocker extending into the atrium of the heart; and a lower portion of the blocker extending into the ventricle of the heart. The method also includes retracting the sheath to release the blocker from compressive forces maintaining the blocker in the delivery configuration. The method also includes expanding the blocker such that the middle portion of the blocker provides a sealing surface for one or more of the valve leaflets. The upper portion and lower portions expand and contract passively upon changes in heart chamber pressure differential. The method also includes detaching the blocker from the catheter; and retracting the catheter and the sheath from the heart.

The upper portion can block a valve leaflet from flailing into the atrium. The method can further include deploying one or more anchors configured to secure the blocker to one or more locations in the heart that are proximal to, distal to or at the level of the valve annulus. The one or more locations can be positioned distal to an annulus of the valve or on the exterior of the heart near the apex. The one or more anchors can include a screw-type anchor coupled to the blocker. Deploying the one or more anchors can include rotating the catheter to advance the screw-type anchor into the one or more locations. The one or more locations can be positioned on an annulus of the valve. The one or more anchors can secure the middle portion in a stationary position to the annulus of the valve. The one or more locations can be positioned proximal to an annulus of the valve. The one or more anchors can include at least one pair of angled clamping wires coupled to and extending proximally from the upper portion of the blocker; and a sliding sleeve having an inner diameter that is smaller than an outer diameter of the upper portion of the blocker when the blocker is in an expanded configuration. The pair of angled clamping wires can extend through the inner diameter of the sliding sleeve. The method can also include expanding the expandable region of the blocker and moving the sliding sleeve in a proximal direction, the inner diameter of the sliding sleeve urging the pair of angled clamping wires towards one another. The pair of angled clamping wires can removably capture at least a portion of the atrial wall between them. The one or more locations can be positioned on the septum between the left and right atria. Retracting the sheath to release the expandable region of the blocker can expand the expandable region. Expanding the blocker can include filling the blocker with a fluid. Filling the blocker with a fluid can include extending the catheter through a flow restriction mechanism in a neck region of the blocker to selectively fill the blocker with filling material delivered through the catheter. The flow restriction mechanism can include a one-way valve such that detaching the blocker from the catheter includes withdrawing the catheter from the one-way valve. The flow restriction mechanism can include a snap ring surrounding the neck region of the blocker. Detaching the blocker from the catheter can include withdrawing the catheter from the neck region and releasing the snap ring to compress the neck region of the blocker.

Other features and advantages should be apparent from the following description of various embodiments, which illustrate, by way of example, the principles of the disclosure.

BRIEF DESCRIPTION OF THE DRAWINGS

FIGS. 10A-10D show a method of filling a fluid-tight blocker device.

FIGS. 11A-11C show various schematic views of another embodiment of a blocker.

FIG. 12A shows a schematic cross-sectional view another embodiment of a blocker during systole.

FIG. 12B shows a schematic cross-sectional view of the blocker from FIG. 12A during diastole.

FIG. 12C shows a schematic top plan view of the blocker from FIG. 12A.

FIGS. 12D-12G show an exemplary delivery of the blocker from FIG. 12A.

FIG. 13A shows a schematic top view of the heart during systole with another embodiment of a blocker in position.

FIG. 13B shows a schematic top view of the heart during diastole with the blocker from FIG. 13A in position.

FIG. 13C shows a schematic cross-sectional view of the heart during systole with the blocker from FIG. 13A in position.

FIG. 13D shows a schematic cross-sectional view of the heart during diastole with the blocker from FIG. 13A in position.

FIG. 14A shows a schematic top view of the heart during systole with another embodiment of a blocker in position.

FIG. 14B shows a schematic top view of the heart during diastole with the blocker from FIG. 14A in position.

FIG. 14C shows a schematic cross-sectional view of the heart during systole with the blocker from FIG. 14A in position.

FIG. 14D shows a schematic cross-sectional view of the heart during diastole with the blocker from FIG. 14A in position.

FIGS. 15A-15D show schematic side views of a blocker having various embodiments of a distal anchoring mechanism.

FIG. 15E shows a schematic side view of the blocker of FIG. 15A including a proximal anchoring mechanism.

FIG. 15F shows a schematic cross-sectional view of a heart with the blocker device of FIG. 15E positioned within the mitral valve. The chordae tendinae and papillary muscles are not shown for clarity.

FIG. 15G shows a schematic top plan view of the mitral valve of FIG. 15E.

FIGS. 19A-19C show schematic cross-sectional views of a blocker device having another embodiment of an anchoring system.

FIG. 46 shows the left ventricle with a needle being advanced from the left atrium into the left ventricle via the leaflet grasping device.

FIG. 47 shows the left ventricle with sutures holding the papillary muscles in a desired position.

FIG. 48 shows a cross-sectional view of the heart with one or more clips clipped to each of the papillary muscles.

FIG. 49 shows a cross-sectional view of the heart with tethered clips attached to opposed walls of the left ventricle.

DETAILED DESCRIPTION

Figure 1B:
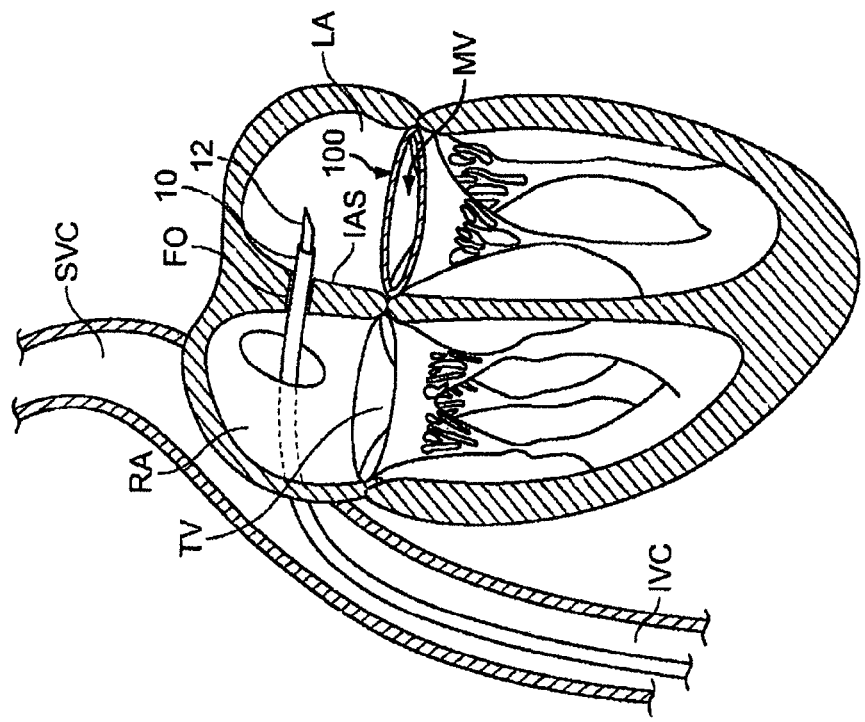
FIG. 1B shows a cross-sectional view of the heart wherein a flexible stent is positioned at or near the mitral valve.

The present invention provides methods, systems, and devices for the endovascular repair of cardiac valves, particularly the atrioventricular valves which inhibit back flow of blood from a heart ventricle during contraction (systole), most particularly the mitral valve between the left atrium and the left ventricle. By "endovascular," it is meant that the procedure(s) of the present invention are performed with interventional tools, guides and supporting catheters and other equipment introduced to the heart chambers from the patient's arterial or venous vasculature remote from the heart. The interventional tools and other equipment may be introduced percutaneously, i.e., through an access sheath, or may be introduced via a surgical cut down, and then advanced from the remote access site through the vasculature until they reach the heart. Thus, the procedures of the present invention will generally not require penetrations made directly through the exterior heart muscle, i.e., myocardium, although there may be some instances where penetrations will be made interior to the heart, e.g., through the interatrial septum to provide for a desired access route.

While the procedures of the present invention will usually be percutaneous and intravascular, many of the tools will find use in minimally invasive and open surgical procedures as well that includes a surgical incision or port access through the heart wall. In particular, the tools for capturing the valve leaflets prior to attachment can find use in virtually any type of procedure for modifying cardiac valve function.

The atrioventricular valves are located at the junctions of the atria and their respective ventricles. The atrioventricular valve between the right atrium and the right ventricle has three valve leaflets (cusps) and is referred to as the tricuspid or right atrioventricular valve. The atrioventricular valve between the left atrium and the left ventricle is a bicuspid valve having only two leaflets (cusps) and is generally referred to as the mitral valve. In both cases, the valve leaflets are connected to the base of the atrial chamber in a region referred to as the valve annulus, and the valve leaflets extend generally downwardly from the annulus into the associated ventricle. In this way, the valve leaflets open during diastole when the heart atria fill with blood, allowing the blood to pass into the ventricle.

During systole, however, the valve leaflets are pushed together and closed to prevent back flow of blood into the atria. The lower ends of the valve leaflets are connected through tendon-like tissue structures called the chordae, which in turn are connected at their lower ends to the papillary muscles. Interventions according to the present invention may be directed at any one of the leaflets, chordae, annulus, or papillary muscles, or combinations thereof. It will be the general purpose of such interventions to modify the manner in which the valve leaflets coapt or close during systole so that back flow or regurgitation is minimized or prevented.

Figure 1A:
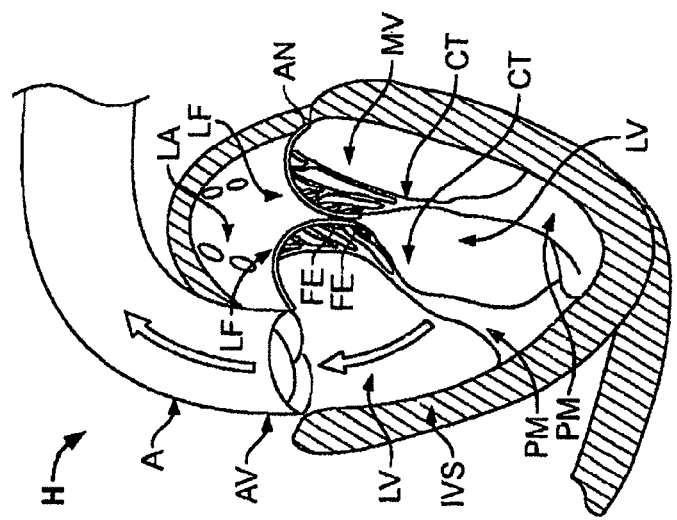
FIG. 1A is a schematic illustration of the left ventricle of a heart showing blood flow during systole with arrows.

The left ventricle LV of a normal heart H in systole is illustrated in FIG. 1A. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1A. The opposite ends of the leaflets LF are attached to the surrounding heart structure along an annular region referred to as the annulus AN. The free edges FE of the leaflets LF are secured to the lower portions of the left ventricle LV through chordae tendineae CT (referred to hereinafter as the chordae) which include plurality of branching tendons secured over the lower surfaces of each of the valve leaflets LF. The chordae CT in turn, are attached to the papillary muscles PM which extend upwardly from the lower portions of the left ventricle and interventricular septum IVS.

While the procedures of the present invention will be most useful with the atrioventricular valves, at least some of the tools described hereinafter may be useful in the repair of other cardiac valves, such as peripheral valves or valves on the venous side of the cardiac circulation, or the aortic valve.

The methods of the present invention can comprise accessing a patient's vasculature at a location remote from the heart, advancing an interventional tool through the vasculature to a ventricle and/or atrium, and engaging the tool against a tissue structure which forms or supports the atrioventricular valve. By engaging the tool against the tissue structure, the tissue structure is modified in a manner that reduces valve leakage or regurgitation during ventricular systole. The tissue structure may be any of one or more of the group consisting of the valve leaflets, chordae, the valve annulus, and the papillary muscles, atrial wall, ventricular wall or adjacent structures. Optionally, the interventional tool will be oriented relative to the atrioventricular valve and/or tissue structure prior to engaging the tool against the tissue structure. The interventional tool may be self-orienting (e.g., pre-shaped) or may include active mechanisms to steer, adjust, or otherwise position the tool.

Alternatively, orientation of the interventional tool may be accomplished in whole or in part using a separate guide catheter, where the guide catheter may be pre-shaped and/or include active steering or other positioning means such as those devices set forth in United States Patent Application Publication Numbers 2004-0044350, 2004-0092962 and U.S. Pat. No. 7,226,467, all of which are expressly incorporated by reference herein. In all cases, it will usually be desirable to confirm the position prior to engaging the valve leaflets or other tissue structures. Such orienting step may comprise positioning the tool relative to a line of coaptation in the atrioventricular valve, e.g., engaging positioning elements in the valve commissures and confirming the desired location using a variety of imaging means such as magnetic resonant imaging (MRI), intracardiac echocardiography (ICE), transesophageal echo (TEE), fluoroscopy, endoscopy, intravascular ultrasound (IVUS) and the like.

In some embodiments, heart disease in general, and valve repair in particular, are treated by targeting the pacing of the heartbeat. In one embodiment, heart disease is treated by introducing one or more pacing leads into a heart chamber. The pacing leads are placed in contact with a heart muscle and are in electrical communication with a power source. The power source provides paced electrical stimuli to the heart muscle. The electrical stimuli are provided during or immediately after systole to extend systolic contraction of the heart, thereby extending the range of systole during each heartbeat. This extension of systole extends the amount of time in which the heart muscle tightens when it would otherwise be relaxing, when there is most mitral regurgitation in diseased mitral valves.

Other embodiments are directed to annuloplasty to treat heart disease in general and valve repair in particular. In one embodiment, shown generally in FIG. 1B, a stent is used to treat the mitral valve. FIG. 1B shows a cross-sectional view of the heart wherein a flexible stent 100 is positioned at or near the mitral valve MV. The stent 100 is annular and is sized and shaped to be positioned on the annulus of the mitral valve. The stent 100 can transition between a collapsed state of reduced size and an expanded state of enlarged size relative to the collapsed state.

The flexible stent 100 can be percutaneously introduced into an individual's heart while being biased toward the collapsed state. The stent is advanced partially through the annulus of the mitral valve so that it is coaxially positioned within the annulus, as shown in FIG. 1B. The stent 100 is then secured to the annulus such that the stent exerts an inward force on the annulus thereby causing the annulus to resist dilation during diastole of the heart.

In yet another embodiment, a device is disclosed for treating the mitral valve. The device can be a stent, such as the stent 100, that is sized to fit coaxially within an annulus of a mitral valve. The stent includes a hollow frame. The frame can be annular such that it has a cross-sectional diameter that is sized such that an outer surface of the frame is in continuous coaxial contact with the annulus. The frame also includes one or more anchors protruding from it for securing the stent to the annulus. The anchors can be prongs, barbs, protrusions, or any structure adapted to secure the stent to the annulus. The stent is flexible between an expanded configuration and a contracted configuration and is biased toward the contracted configuration so that it exerts an inward force on the annulus.

In one embodiment, the stent 100 is delivered using a delivery catheter 10 that is advanced from the inferior vena cava IVC into the right atrium RA. Once the catheter 10 reaches the anterior side of the interatrial septum IAS, a needle 12 may be advanced so that it penetrates through the septum at the fossa ovalis FO or the foramen ovale into the left atrium LA. At this point, a delivery device can be exchanged for the needle and the delivery device used to deliver the stent 100. The catheter 10 can also approach the heart in other manners.

Figure 2A:
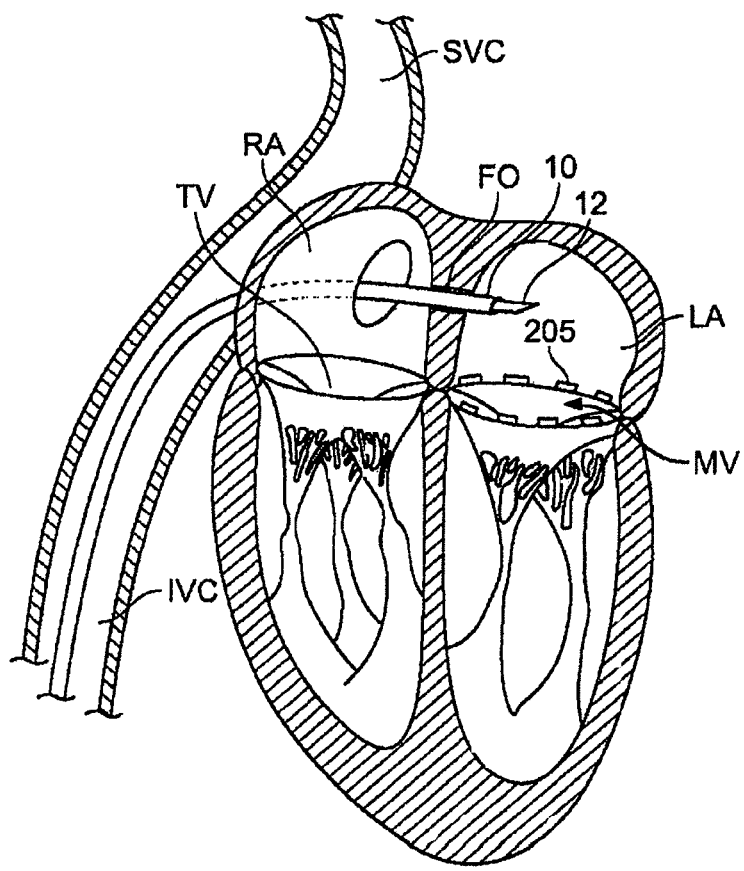
FIG. 2A shows a cross-sectional view of the heart showing one or more magnets positioned around the annulus of the mitral valve.
Figure 2B:
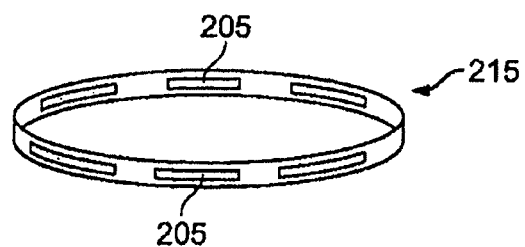
FIG. 2B shows an annular band with magnets that can be positioned on the mitral valve annulus.

FIG. 2A shows a cross-sectional view of the heart showing one or more magnets 205 positioned around the annulus of the mitral valve MV. A corresponding method of treating heart disease involves the use of magnets. The method includes percutaneously introducing at least a first magnet 205 into an individual's heart and securing it to the mitral valve MV annulus. At least a second magnet 205 is percutaneously introduced into the heart and advanced so that it is within a magnetic field of the first magnet. The second magnet is secured to the heart. The polarity of one of the two magnets is then cyclically changed in synchronization with the heart beat so that the magnets attract and repel each other in synchronization with the heart beat. The first magnet therefore moves in relation to the second magnet and exerts an inward closing force on the mitral valve during systole. The magnets 205 can be positioned on an annular band 215 (shown in FIG. 2B) that is sized and shaped to be implanted on the annulus of the mitral valve. The band 215 can be, for example, a stent.

In one embodiment, the magnets 205 or the annular band 215 are delivered using a delivery catheter 10 that is advanced from the inferior vena cava IVC into the right atrium RA, as described above with reference to FIG. 1. Any of the devices described herein can be percutaneously delivered into the heart by coupling the device to a delivery device, such as a steerable delivery catheter.

In yet another embodiment involving magnets, two or more magnets are percutaneously introduced into an individual's coronary sinus such that they attract or repel each other to reshape the coronary sinus and an underlying mitral valve annulus.

Figure 3:
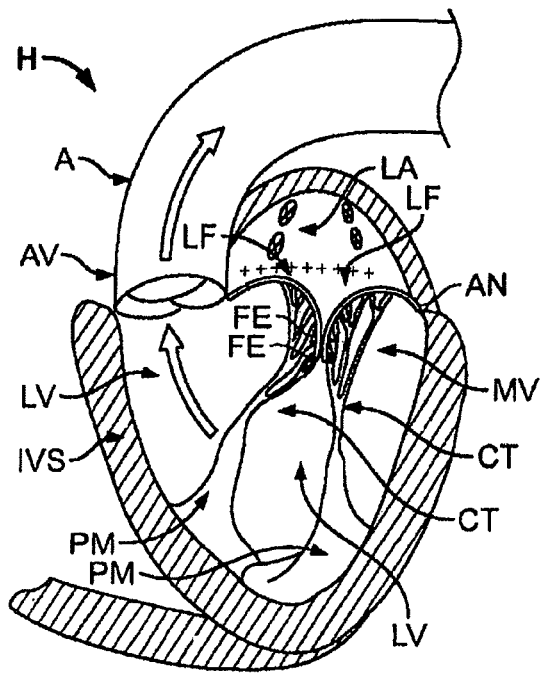
FIG. 3 shows a cross-sectional view of the heart identifying locations for placement of valves.

Other embodiments involve various prosthetics for treating heart disease in general and defective or diseased mitral valves in particular. In one embodiment, a method of treatment includes placing one or more one-way valves in one or more pulmonary veins of an individual either near the ostium of the vein or at some point along the length of the PV. Valves that may be used, for example may be stentless valves such as designs similar to the TORONTO SPV® (Stentless Porcine Valve) valve, mechanical or tissue heart valves or percutaneous heart valves as are known in the art provided they are sized appropriately to fit within the lumen of the pulmonary vein, as shown in FIG. 3. In FIG. 3, the locations in the left atrium LA where valves can be positioned in pulmonary vein orifices are represented by an "X". In addition, certain venous valve devices and techniques may be employed such as those described in U.S. Pat. Nos. 6,299,637 and 6,585,761, and United States Patent Applications 20040215339 and 20050273160, the entire contents of which are incorporated herein by reference. A valve prosthesis for placement in the ostia of the pulmonary vein from the left atrium may be in the range of 6-20 mm in diameter. Placement of individual valves in the pulmonary vein ostia (where the pulmonary veins open or take off from the left atrium) may be achieved by obtaining trans septal access to the left atrium with a steerable catheter, positioning a guidewire through the catheter and into the targeted pulmonary vein, and deploying a valve delivery catheter over the guidewire and deploying the valve out of the delivery catheter. The valve may be formed of a deformable material, such as stainless steel, or of a self-expanding material such as NiTi, and include tissue leaflets or leaflets formed of a synthetic material, such as is known in the art. A line of +++++ symbols in FIG. 3 represents a mid-atrial location above the mitral valve where a single valve can be positioned as disclosed later in this specification.

The following references, all of which are expressly incorporated by reference herein, describe devices (such as steerable catheters) and methods for delivering interventional devices to a target location within a body: United States Patent Application Publication Numbers 2004-0044350, 2004-0092962 and U.S. Pat. No. 7,226,467.

Figure 4:
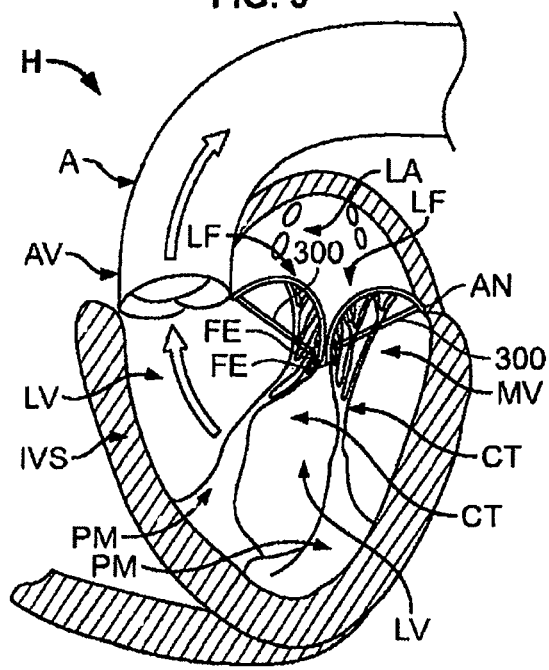
FIG. 4 show a cross-sectional view of the heart with a pair of flaps mounted at or near the mitral valve.
Figure 5A:
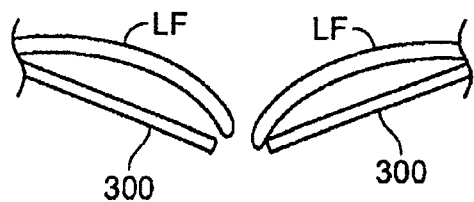
FIG. 5A shows a schematic side view of the mitral valve leaflets with a flap positioned immediately below each leaflet.
Figure 5B:
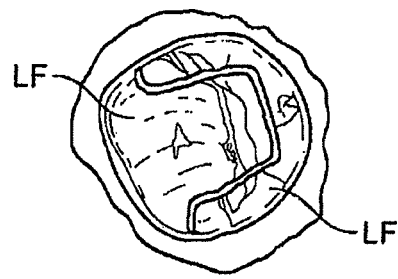
FIG. 5B shows a downward view of the mitral valve with a pair of exemplary flaps superimposed over the leaflets.
Figure 5C:
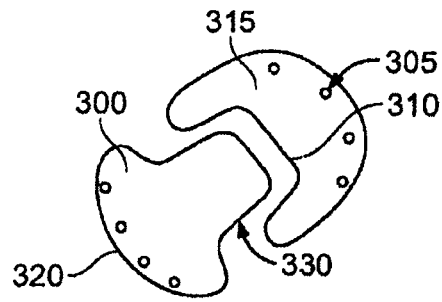
FIG. 5C shows a pair of mitral valve leaflet flaps having complementary shapes.

FIG. 4 show a cross-sectional view of the heart with a pair of flaps mounted at or near the mitral valve. FIG. 5A shows a schematic side view of the mitral valve leaflets LF with a flap 300 positioned immediately below each leaflet. The flap 300 can be contoured so as to conform at least approximately to the shape of a leaflet, or the flap 300 can be straight as shown in FIG. 4. FIG. 5B shows a downward view of the mitral valve with a pair of exemplary flaps superimposed over the leaflets LF. As shown in FIG. 5C, the flaps can have complementary shapes with a first flap having a protrusion that mates with a corresponding recess in a second flap.

In corresponding method of treatment, shown in FIGS. 4 and 5C, a first flap 300 with an attachment end 305 and a free end 310 is provided. The attachment end 305 of the first flap 300 is secured to the inside wall of the ventricle below the mitral valve. A second flap 315 with an attachment end 320 and a free end 330 is provided and is also secured to the inside wall of the ventricle below the mitral valve. The first and second flaps 300, 315 are oriented so that they face each other and the free ends 310, 330 are biased toward each other and approximate against each other during systole. This system provides a redundant valving system to assist the function of the native mitral valve.

Figure 6A:
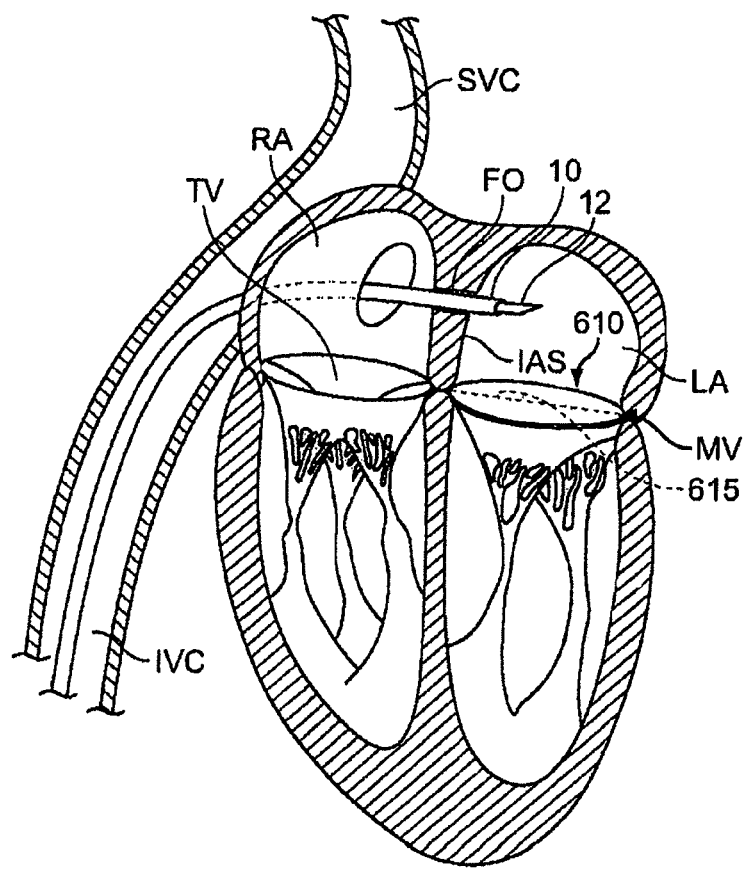
FIG. 6A shows a cross-sectional view of the heart with a membrane ring positioned at the mitral valve annulus.
Figure 6B:
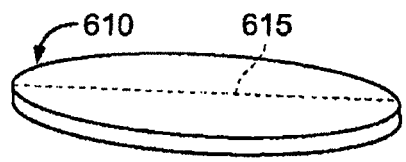
FIG. 6B shows a schematic view of the membrane ring, which includes an annular ring on which is mounted a membrane.

In other embodiments, devices and methods that involve prosthetic discs are disclosed. For example, FIG. 6A shows a cross-sectional view of the heart with a membrane ring 610 positioned at the mitral valve annulus. FIG. 6B shows a schematic view of the membrane ring 610, which includes an annular ring on which is mounted a membrane. The membrane includes a series of perforations 615 extending through the membrane surface. One or more anchor devices, such as prongs, can be located on the ring for securing the ring to the mitral valve.

In one embodiment, a device for treating heart disease in general and defective or diseased mitral valves in particular includes a disc having a ring, a membrane stretched across an opening of the ring, and one or more anchors for securing the disc to an annulus of a mitral valve. The disc is sized to cover the annulus of the mitral valve, and the membrane includes one or more perforations that permit one way fluid flow through the disc. Methods of treatment using the device are also provided.

Devices and methods are disclosed that involve a device known as a blocker or a bladder which improves the functioning of a heart valve by providing a surface against which valve leaflets may coapt. The blocker device may be used to improve the functioning of any heart valve (tricuspid, aortic, mitral) though for the purpose of brevity most examples will be in relation to the mitral valve. A blocker device can be used to treat mitral valve disease such as mitral regurgitation (MR). Blocker devices can also be used for treating other valve diseases such as tricuspid valve regurgitation and aortic insufficiency.

Figure 7B:
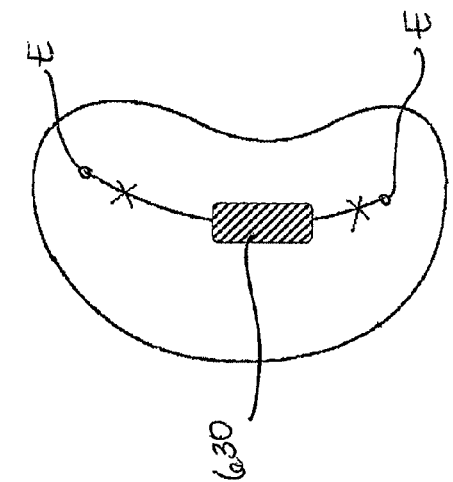
FIG. 7B shows a schematic top plan view of the mitral valve with the leaflets in an abnormal closure state such that a gap is present between the leaflets.

As previously described functional mitral valve disease is usually characterized by the failure of the anterior mitral valve leaflet to coapt with (or "meet") the posterior mitral leaflet during systole. This can occur due to an enlarged ventricle or other impediment to the leaflets rising up far enough toward each other to close the gap or seal against each other during systole. FIG. 7A shows a schematic side view and FIG. 7B shows a top plan view of a mitral valve with the leaflets LF in an abnormal closure state such that a gap G is present between the leaflets. Leaflets that fail to coapt can result in valve regurgitation (as represented by the arrow RF).

Upon positioning within, on, or around the valve, a blocker device can provide a surface against which at least a portion of the valve leaflet or leaflets can coapt. The blocker assists the valve preventing regurgitation by increasing the coaptation area of the valve leaflets LF and/or decreasing the coaptation depth of the leaflets LF. Increasing coaptation of the valve can be accomplished by placing a blocker in the diseased valve orifice and providing a surface against which the leaflets LF can coapt therein closing the valve during systole. The blocker can be conformable such that the leaflets press against and seal with the blocker during systole. The blocker assists in closing the valve without altering the shape of the annulus AN and/or repositioning the papillary muscles PM. The blocker can conform to the leaflet shape providing better sealing to minimize and block mitral valve regurgitation.

Figure 7D:
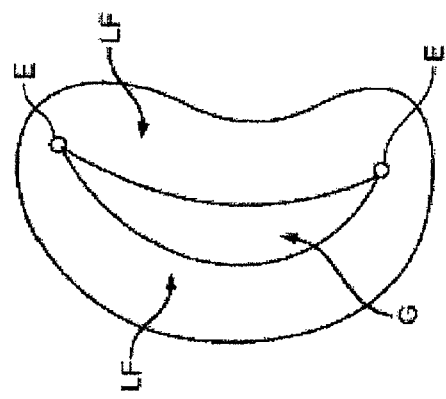
FIG. 7D shows a schematic top plan view of the mitral valve leaflets with a blocker positioned between the leaflets.
Figure 7A:
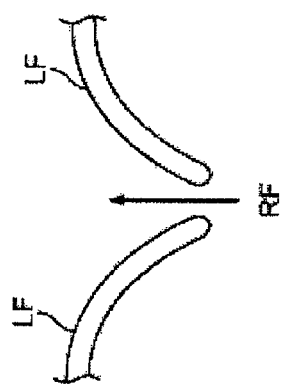
FIG. 7A shows a schematic side view of the mitral valve leaflets failing to coapt.
Figure 7C:
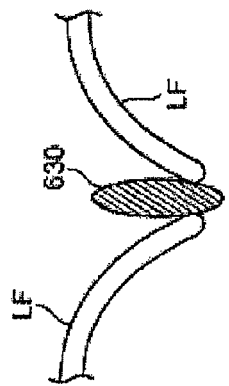
FIG. 7C shows a schematic side view of the mitral valve leaflets with a blocker positioned between the leaflets.

FIGS. 7C and 7D show an embodiment of a blocker 630 positioned such that the blocker 630 is coaxially aligned between the leaflets LF along the line of coaptation of the leaflets LF. The blocker 630 can provide a surface against which at least a portion of the leaflets LF can seal and thus serve as a coaptation device for the leaflets. An atrial portion of the blocker 630 can extend into the left atrium, and a ventricular portion of the blocker 630 can extend into the left ventricle.

The configuration of the blockers described herein can vary. For example, the blocker can be solid, semi-solid or have a mesh-like configuration. The blocker can also have a variety of shapes such that it is optimized based on the geometry of the valve, the alignment of the leaflets and the size/shape of the valve orifice. For example, the blocker can have a spherical, ellipsoid, wing-like, t-shape, x-shape, y-shape, annular, sheet, rectangular, umbrella-shape or other geometry. It should be understood that any of the blocker embodiments described herein may be used with any of the different anchoring mechanisms described herein. For the sake of brevity, Applicants will omit an explicit description of each combination of blocker embodiment and anchoring mechanism. Additionally, Applicants describe herein different methods for accessing heart valves and for implanting the blocker device within the heart. The different blocker devices are amenable to several different methods of access and implantation. Applicants will provide representative descriptions of how to access the heart vale and implant the blocker. However, for the sake of brevity, Applicants will omit an explicit description of each method of access/implantation with respect to each blocker embodiment.

Advantageously, the blocker can be expandable or can include an expandable region. The expandable region can be self-expanding or actively expanded such as by fluid filling. As will be described in more detail below, a blocker can include a "balloon"-type, compliant expandable region such as a sealed, fluid-filled bladder. A blocker can include an expandable frame or mesh covered by a compliant material ("covered stent" type blocker). A blocker can include an expandable region composed of a compressed, sponge-like material. A blocker can include an expandable region that takes on a blocking geometry, for example, a T-shape or other shape with an enlarged "head" at the atrial side of the valve. A blocker can include an expandable region that is dynamic and moves with the changes in pressure and flow of the diastolic/systolic cycle. A blocker can include an expandable region that sits like a diaphragm across the valve to block regurgitation. Features of the various blockers described herein can be used in combination with any of the embodiments described herein.

Materials suitable for construction of the blocker can vary, for example, synthetic polymers, biological polymers, metals, ceramics, and biological materials. Suitable synthetic polymers can include fluoroethylenes, silicones, urethanes, polyamides, polyimides, polysulfone, polyether ketones, polymethyl methacrylates, and the like. Suitable metals can be composed from a variety of biocompatible elements or alloys. Examples include shape-memory metal (e.g. Nitinol), titanium, Ti-6AL-4V, stainless steel alloys, chromium alloys, and cobalt alloys. The materials can also be subjected to surface modification techniques to make them selectively bioreactive or non-reactive, including texturing, surface coatings, electrical modification, coating or impregnation of biologically derived coatings and a variety of growth-healing modifications.

Blocker embodiments described herein can be delivered using interventional tools, guides and supporting catheters and other equipment introduced to the heart chambers from the patient's arterial or venous vasculature remote from the heart. The blockers described herein can be compressed to a low profile for minimally-invasive or percutaneous delivery. They can be advanced from the remote access site through the vasculature until they reach the heart. For example, the blockers can be advanced from a venous site such as the femoral vein, jugular vein, or another portion of the patient's vasculature. It is also appreciated that blockers can be inserted directly into the body through a chest incision. A guidewire can be steered from a remote site through the patient's vasculature into the inferior vena cava (IVC) through the right atrium so that the guidewire pierces the interatrial septum. The guidewire can then extend across the left atrium and then downward through the mitral valve MV to the left ventricle. After the guidewire is appropriately positioned, a catheter can be passed over the guidewire and used for delivery of a blocker device.

Blocker embodiments described herein can also be delivered using a catheter advanced through retrograde access through, for example an artery, across the aortic arch and the aortic valve and to the mitral valve by way of the ventricle. Alternative delivery methods of blocker embodiments described herein can include inserting the blocker through a small access port such as a mini-thoracotomy in the chest wall and into the left ventricle apex. From there, the blocker can be advanced through the left ventricle into the left atrium. It should be appreciated that the device can also be delivered via the left atrial wall as well. Positioning of the tool and/or blockers described herein can be confirmed using a variety of imaging means such as magnetic resonant imaging (MRI), intracardiac echocardiography (ICE), transesophageal echo (TEE), fluoroscopy, endoscopy, intravascular ultrasound (IVUS) and the like.

Following insertion, the blocker can be anchored and/or expanded into position. A sheath can be used to compress the blocker during insertion such that upon retraction the sheath allows for expansion of the blocker. Expansion mechanisms of the expandable portion of the blocker can vary. In an embodiment, expansion of the blocker can occur through a passive, self-expansion mechanism. In another embodiment, the blocker can be actively expanded such as by infusing a filling fluid through the catheter lumen into a sealed expandable portion. Upon expansion of the blocker, mitral regurgitation and ventricular filling can be assessed to determine whether expansion of the blocker is sufficient. The blocker can be reversibly coupled to the catheter or sheath such that the blocker can be retracted back into the catheter or advancing the sheath if repositioning is necessary. If the result is not satisfactory, the blocker can be retracted, repositioned, redeployed or removed.

If the blocker includes one or more anchors, materials suitable for the constructions of the anchors can vary as well. Materials can include biocompatible and/or coated, impregnated, or otherwise treated with a material or other materials to impart biocompatibility, shape-memory metal (e.g. Nitinol and Nitinol alloys), stainless steel and stainless steel alloys, titanium and titanium alloys, cobalt-chrome alloys, wire-mesh, and the like. The anchor can also be constructed of materials such as thread made of, for example, nylon, braided nylon, PTFE, ePTFE, medical-grade sutures and the like or combinations of the above.

FIG. 7D illustrates an embodiment of a blocker 630 that is attached or anchored to the mitral valve at opposite edges E of the gap G (shown in FIG. 7B). The blocker devices described herein can be attached or anchored to various locations adjacent to or on the valve being treated. It should also be appreciated that the blocker device can be positioned without anchors. The blocker devices described herein can include proximal anchor mechanisms that secure to tissues at or superior to the level of the valve, for example the atrium, coronary sinus, interatrial septum or upper surface of the annulus or valve leaflets. The proximal anchors can act to suspend the blacker between the valve leaflets. The blocker devices described herein can include distal anchor mechanisms that secure to tissues at or inferior to the level of the valve, for example, the ventricle wall, interventricular septum, or the lower surface of the annulus or valve leaflets. In another embodiment, a distal portion of the blocker can be secured to the chordae tendinae and/or the papillary muscle. In another embodiment, the blocker is secured by a combination of anchoring mechanisms, for example both proximally and distally to the level of the valve. It should be appreciated that a combination of anchor types can be used and that the anchors can secure the blocker to different portions of the heart including the external wall of the heart.

The timing of the deployment of the anchoring mechanisms, if used, can vary. For example, the anchoring mechanisms can be deployed prior to or after the blocker is in place between the leaflets. For example, in one embodiment the blocker includes a distal coiled screw anchor that is screwed into the myocardium of the left ventricle, for example, by rotating the catheter prior to placement of the blocker between the leaflets. In another embodiment, the blocker includes a chordal attachment anchor that is delivered prior to deployment of the blocker from the catheter tube. In these examples, once the anchors are in place the blocker is positioned between the leaflets and expanded or allowed to expand. It should be appreciated, however, that expansion can occur prior to anchoring the blocker or that no anchoring mechanism be used at all. It should also be appreciated that the anchoring mechanisms can be adjusted after deployment such that they release the heart tissue, for example, if the results of the blocker are not satisfactory. In an embodiment, the catheter can be used to rotate the blocker and unscrew the coiled anchors from their tissue attachment. Thereafter the device can be re-positioned, re-deployed or removed. If the result is satisfactory, the catheter can be detached from the blocker and withdrawn.

Figure 8:
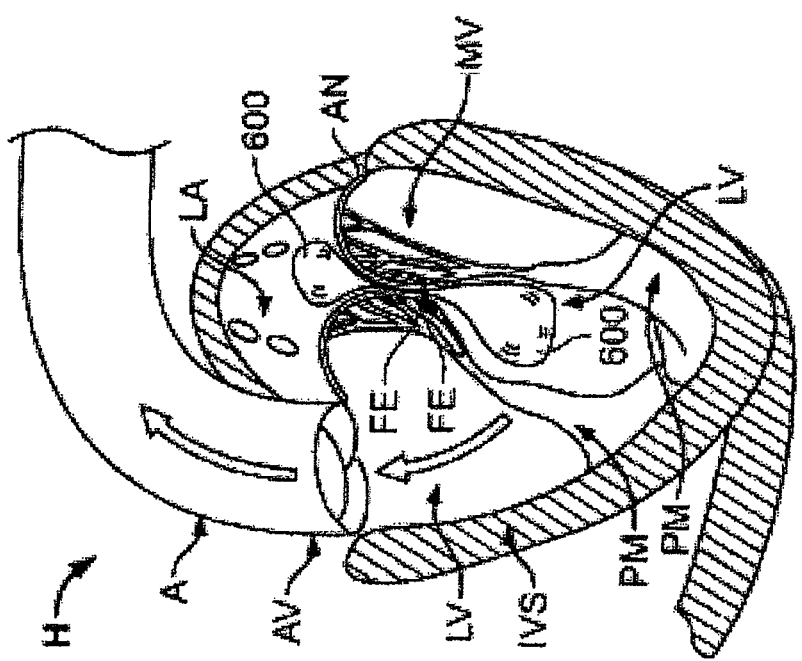
FIG. 8 shows a cross-sectional view of a heart with a blocker device positioned partially within the left ventricle and partially within the left atrium.

FIG. 8 shows an embodiment of a blocker that is an expandable blocker 600. The blocker 600 can be a fluid-tight expandable element or bladder that can be filled with a fluid, including a liquid or a gas. The blocker 600 can be positioned partially within the left ventricle and partially within the left atrium. The bladder 600 can be placed across the mitral valve MV between the left atrium LA and the left ventricle LV. Upon compression of the left ventricle LV during systole, the volume of the blocker 600 can expand on the left atrial LA side of the heart, providing a baffle or sealing volume to which the leaflets of the mitral valve coapt. The blocker 600 also can block the flail and billowing of a leaflet into the left atrium. The blocker 600 can also have enlarged portions on both the atrial and ventricular sides with a generally narrower transition zone therebetween. The enlarged portions can maintain the blocker in position and prevent the blocker from migrating into the atrium or the ventricle. The blocker 600 can also be formed on a cage or other infrastructure to position it within the line of coaptation of the mitral valve.

Figure 9B:
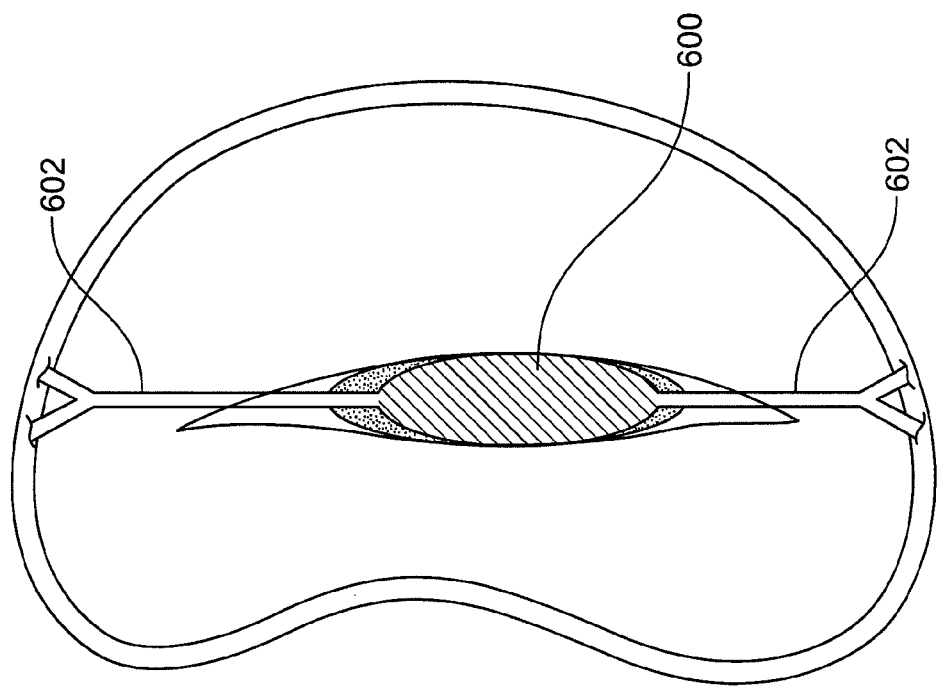
FIGS. 9A-9B show schematic top plan views of the mitral valve leaflets with a blocker anchored between the leaflets during diastole and systole.
Figure 9A:
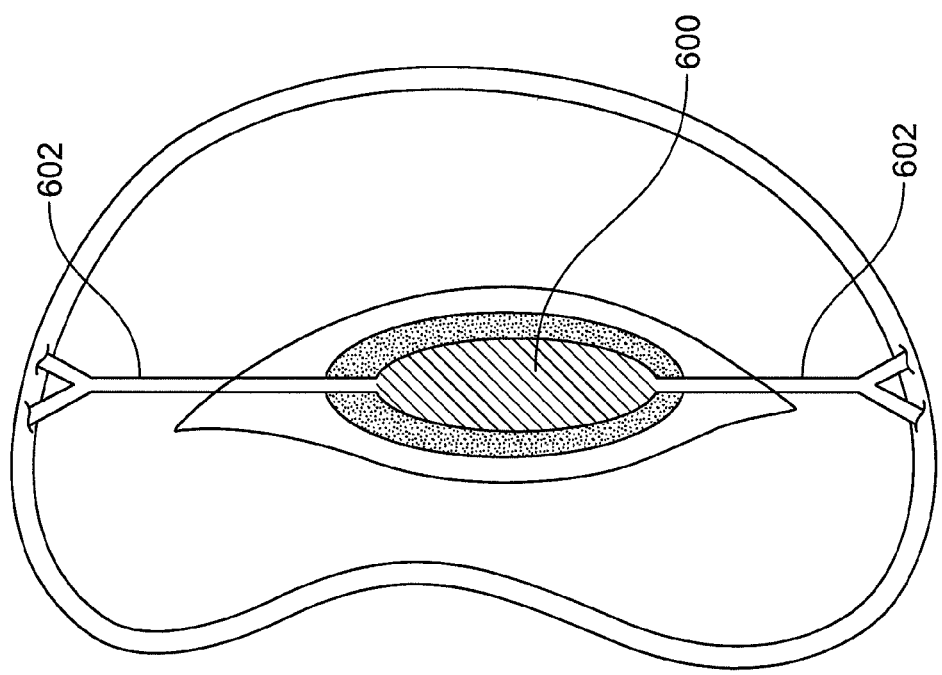
Figures 13E, 13F:
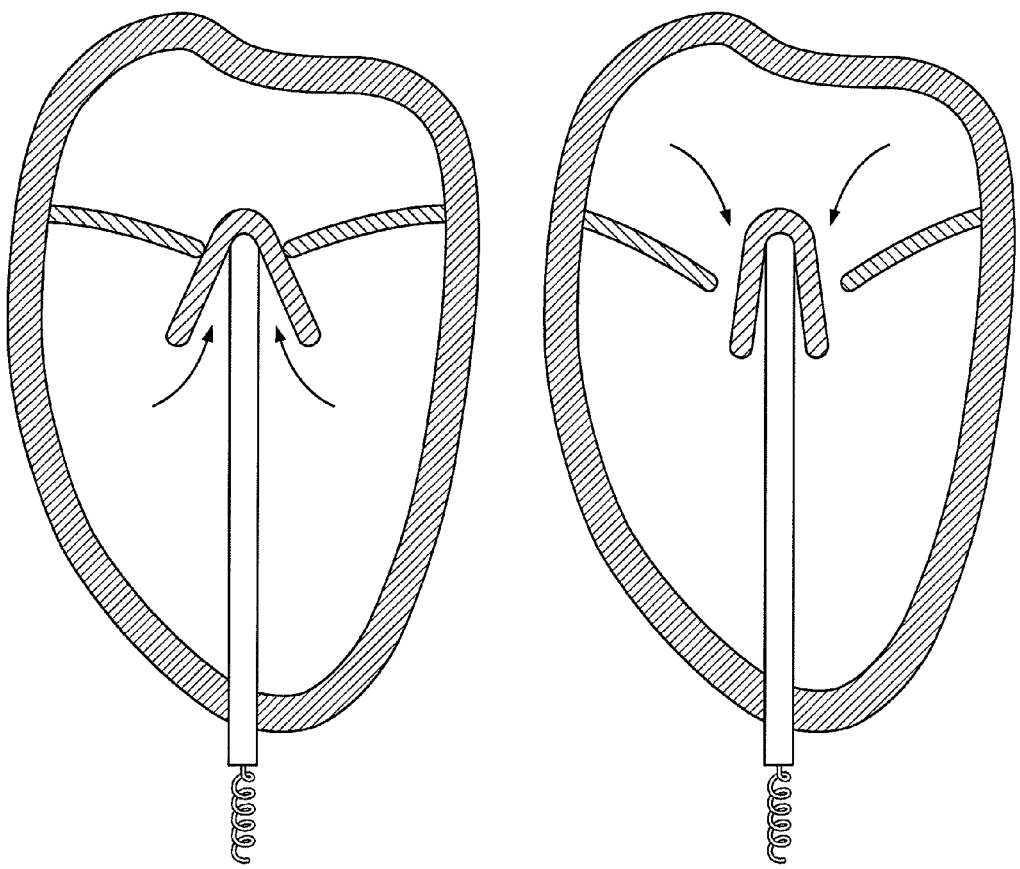
FIG. 13E shows a schematic cross-sectional view of a heart during systole with the blocker device of FIG. 13A including a distal anchoring mechanism.
FIG. 13F shows a schematic cross-sectional view of a heart during diastole with the blocker device of FIG. 13A including a distal anchoring mechanism.

The blocker 600 can include one or more anchors for securing the blocker to an annulus of a mitral valve. In an embodiment, the mid portion of the blocker 600 can be secured to the annulus of the mitral valve such that the midportion remains stationery while the atrial and ventricular portions expand and contract passively between the atrium and ventricle due on pressure differentials during systole and diastole. FIGS. 9A-9B shows an embodiment of a blocker 600 that includes an anchor 602 on each end of the blocker 600. The anchor(s) 602 can be positioned near the mid portion or narrower portion of the blocker 600 and secure the blocker 600 to the annulus.

As mentioned above, the blocker 600 can be an expandable element that can be filled with a fluid, such as a liquid, gel, gas or other material. FIGS. 10A-10D illustrate methods of filling the blocker 600 upon implantation between the valve leaflets. The blocker 600 can include a neck region 601 near its proximal end having a valve 603 through which filling material can be infused. The valve mechanism or configuration can vary. In an embodiment shown in FIG. 10A-10B, the valve 603 can be a duckbill valve having one or more flexible "flaps" that close and seal against one another. The delivery catheter or a filing tube 604 can be inserted through the valve 603 such that an opening at the distal end of the filling tube 604 extends within a lumen 605 of the blocker 600. Upon filling of the blocker 600 with material, the filling tube 604 can be removed from the valve 603 by withdrawing it in a proximal direction. The flaps of the valve 603 can then close and prevent escape of the filling material delivered to the lumen 605 of the blocker 600. The filled lumen 605 of the blocker 600 can have a pressure that is higher than the pressure on the proximal side of the valve which can aid in urging the valve flaps towards one another and closing the valve such that filling material does not flow out of the blocker 600 as shown in FIG. 10B. FIGS. 10C-10D illustrate an alternative valve design which involves the use of a spring clip 606. In this embodiment, the blocker 600 has a neck region 601 that is clamped on an external surface by a clip 606 or other spring-loaded mechanism. The clip 606 can be initially held open, for example, by the catheter or filling tube 604 inserted through the neck of the blocker 600. After filling of the blocker 600 with material, the filling tube 604 can be removed and the clip 606 spring closed around the neck region 601 of the blocker 600. The clip 606 in its closed position can seal off the proximal end of the blocker 600 (see FIG. 10D).

FIGS. 11A-11C show another embodiment of a blocker 3800. The blocker 3800 can be oriented along the leaflet coaptation. The blocker 3800 can extend a portion of or the full-width of leaflet coaptation. The blocker 3800 can allow for both leaflets LF to coapt to and open away from the blocker 3800. The blocker 3800 can include a central bar 3805 that can optionally extend downward through the gap G between the leaflets LF. The blocker 3800 can include anchors 3820 that upon positioning within the valve are oriented near both leaflet commissures C and push outward against the atrial wall. The anchors 3820 can have one or more frictional elements to improve their interface with the surrounding anatomy. The blocker 3800 also can include an expandable anchor ring 3810 (either self-expanding or balloon-type expanding) coupled to the bar 3805 and/or the anchors 3820 that extends around the circumference of the annulus AN. The circumferential anchor ring 3810 can expand and push out against the atrial wall at the annulus level thereby retaining the bar 3805 in position between the leaflets LF. In an embodiment, the blocker 3800 and anchor ring 3810 can include a self-expanding mesh covered with a compliant material for improved sealing and leaflet coaptation. In another embodiment, the blocker 3800 and anchor ring 3810 are balloon-expanded or filled with a fluid material such as two-part epoxy, resin, polymer, hardening or hardenable material, Hydrogel material, saline or other material. In another embodiment, the blocker 3800 and anchor ring 3810 are made of a compressed, sponge-like material that expands. Various features of the blocker 3800 can be used in combination with any of the blocker embodiments described herein.

FIGS. 12A-12G show another embodiment of an expandable blocker. In this embodiment, the blocker 4000 can include a frame 4005 having an upper portion 4010 that is oriented within the left atrium above the level of the annulus, a lower portion 4020 that is oriented within the left ventricle below the level of the annulus and a middle portion 4025 that is oriented at the level of the annulus. The frame 4005 can be generally flexible and can be made from shape-memory metal (e.g. Nitinol) or an expandable wire mesh or the like. The frame 4005 can be covered by a membrane or coating 4030 that can be constructed of a flexible, compliant material such as silicone rubber or a saline-filled balloon structure. It should be appreciated that the frame 4005 need not be flexible. The blocker 4000 can be positioned over the gap G between the leaflets LF along the line of coaptation C. The upper portion 4010 of the frame 4005 can rest above the valve plane such that it contacts or rests upon the anterior and posterior annulus AN. The lower portion 4020 of the frame 4005 can extend under the valve leaflets such that it does not come in contact with the annulus AN as shown in FIG. 12A-12C.

The frame 4005 can be held in place during systole and diastole due to a spring force of the frame 4005. The blocker 4000 can plug the gap G between the anterior and posterior leaflets LF, but does not require sutures or anchors due to the configuration of the upper and lower frame portions 4010, 4020 relative to the anatomy. The upper portion 4010 of the frame 4005 can provide anchoring support through its interaction with the annulus wall and prevent the blocker 4000 from moving during heart function. The lower portion 4020 of the frame 4005 can capture the leaflets LF and close the gap G between the leaflets LF as well as keeping the blocker 4000 in position within the valve. It should be appreciated that the frame 4005 can also be held in place using one or more anchors.

In an embodiment, the lower portion 4020 of the blocker 4000 can move in response to the changes in pressure during the diastolic/systolic cycle such that the leaflets LF are captured between the lower portion 4020 and the upper portion 4010 of the frame 4005. The lower portion 4020 of the frame 4005 can include a pair of arms 4035, 4040 that move upward and downward. During systole the arms 4035, 4040 move upward flattening out against the valve leaflets LF trapping them between the arms 4035, 4040 and the upper portion 4010 of the frame 4005. During diastole, the blocker 4000 arms 4035, 4040 can spring back to a relaxed position. It should be appreciated that movement of the blocker arms 4035, 4040 is optional and that the arms 4035, 4040 can also be fixed in orientation and not move during the diastolic/systolic cycle.

FIGS. 12D-12G illustrate a method of delivery of the blocker 4000. During delivery, the blocker 4000 can be oriented within the catheter 4045 such that the upper portion 4010 and lower portion 4020 are each compressed into a low profile. The catheter 4045 can be fed through the valve such that upon withdrawal of the catheter 4045 the arms 4035, 4040 of the lower portion 4020 can relax into position below the leaflets LF. After the lower portion 4020 is deployed, the catheter 4045 can be further withdrawn such that the upper portion 4010 can be deployed and relaxes into position above the valve leaflets LF. The diameter of the upper portion 4010 prevents it from passing through the valve.

Other embodiments of blockers described herein also use dynamic methods of blocking regurgitation through the valve such as by passively changing their shape or changing their orientation during systole and diastole using the forces of the cardiac circulation to effect the shape or orientation change. FIGS. 13A-13F illustrate an embodiment of a blocker 4100 having a folded configuration and including flaps or arms that can "tent" or fill during systole. During systole, as blood flows against the closed mitral valve, the flaps of the blocker 4100 open up and tent as they fill with the flow blocking mitral regurgitation. During diastole, blood flows from the LA into the LV through the open mitral valve. The flaps move downward and the blocker 4100 folds to allow blood to flow past the blocker 4100 passively allowing diastolic flow. It should be appreciated that the blocker 4100 can also incorporate a hinge feature to aid in the folding of the flaps on either side of the central region. In such an embodiment, the flaps can passively articulate or rotate about the pivot axis of the hinge while the hinge remains fixed with the cardiac circulation.

The blocker 4100 can include a frame constructed of a flexible material, for example, the blocker 4100 can be constructed of a shape-memory metal (e.g. Nitinol) or a flexible semi-rigid polymer such as Nylon or PTFE. The blocker 4100 can be formed into a flexible sheet or other shape. The blocker frame can be covered by a compliant membrane or other material to improve sealing function. As mentioned above, the frame can include the pair of arms positioned at least in part below the level of the annulus. The frame can be moveable between a fluid flow-allowing position and a fluid flow-blocker position in response to changes in heart chamber pressure during the heart cycle. The pair of arms can tent upwards against the lower surface of a valve leaflet, for example during systole into the fluid flow-blocking position. The pair of arms can collapse downward away from the lower surface of the valve leaflet, for example during diastole into the fluid flow-allowing position.

The blocker 4100 can be tethered to one or more anchors 4105. The one or more anchors 4105 can include a tether connecting a portion of the frame of the blocker 4100 to an expandable portion of the anchor 4105 positioned, for example, within the coronary sinus (see FIGS. 13A-13B). The tether can also connect the blocker 4100 to an anchor that can be positioned distally, for example within the left ventricular wall (see FIGS. 13E-13F). The tether can connect to the frame, for example at a portion aligned near an outer edge E of the gap G. The frame can include a stationary portion coupled to a proximal portion of the pair of arms. The stationary portion can be positioned above the level of the annulus and have a long axis oriented orthogonal to the line of coaptation. The tether can connect to the frame at the stationary portion near a region aligned near an outer edge of the gap. The tether can connect to the frame at a lower surface of the stationary portion, for example, when interconnecting the blocker to a location distal to the valve such as the wall of the left ventricle.

In another embodiment, best seen in FIGS. 14A-14F, the blocker 4200 can act as a "baffle" and change orientation, such as by swiveling, rotating or pivoting, thereby opening and closing the valve. The change in orientation of the blocker 4200 can be passive in that the blocker opens and closes as a result of the change in pressure and flow reversal during the systolic/diastolic cycle. Alternatively, the orientation change of the blocker 4200 can be semi-active, for example, a spring-loaded mechanism that orients the blocker 4200 in a first direction and changes orientation, for example, due to blood flow in a second, opposite direction. In an embodiment, the blocker 4200 can operate as a butterfly valve.

Figure 14E:
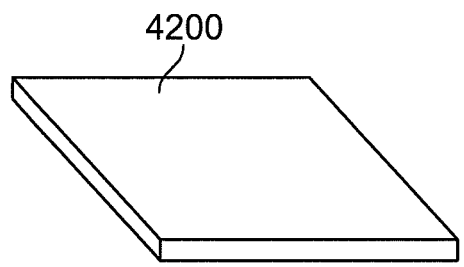
FIGS. 14E-14F show schematic perspective views of the blocker from FIG. 14A in open and closed orientations.
Figure 14F:
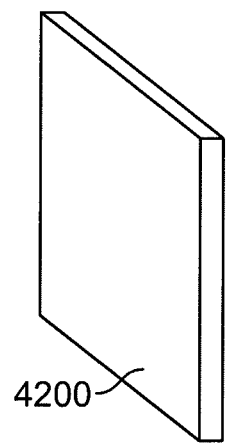

The blocker 4200 can be a planar structure having a rectangular shape such that it is longer than it is wide (see FIGS. 14E and 14F). During systole, the blocker 4200 can be aligned such that the long axis of the blocker 4200 spans between the leaflets LF and blocks the flow of blood through the gap G (see FIGS. 14A and 14C). During diastole, the blocker 4200 can swivel approximately 90 degrees such that the long axis of the blocker 4200 aligns with the gap G and flow is allowed through the valve (FIGS. 14B and 14D). The blocker 4200 swivels between a closed position during systole and an open position during diastole regulating flow through the valve as a result of blood flow during the cardiac cycle.

The blocker 4200 can be tethered to an anchor 4205 such as a stent or similar structure. The blocker 4200 can be constructed of a biocompatible material such as a metal or polymer, for example an implantable stainless steel, titanium, or Nitinol. The blocker 4200 can be generally rigid and the anchors 4205 can be flexible. Various features of the blockers 4100, 4200 can be used in combination with any of the blocker embodiments described herein.

As mentioned previously, the blockers described herein can include one or more anchoring mechanisms. The blocker devices described herein can include proximal or mid-portion anchor mechanisms that can be secured to the atrium or to the septum or to the leaflets or annulus. In other embodiments, the blocker can be secured distally such as to the ventricle or the chordae tendinae or the papillary muscle. It should be appreciated that a combination of anchoring mechanisms can be incorporated and that the anchors can secure the blocker to different portions of the heart. The blocker devices described herein can also be used without the aid of an anchor.

FIGS. 15A-15D illustrate blocker embodiments incorporating distal anchors. As noted previously, the distal anchors illustrated in FIGS. 15A-15D can be used with any of the blocker concepts described in this disclosure, and explicitly not limited to the blocker 4301 depicted in FIG. 15A.

FIG. 15A illustrates a blocker 4300 that includes a distal anchor 4305 that is a coiled screw type of anchor, which can embed into the heart wall. In another embodiment shown in FIG. 15B, the blocker 4300 includes multiple spring wire supports 4310 that prop up the expandable region 4301 from the coiled screw anchor 4305. The spring wire supports can provide additional axial stability. As shown in FIG. 15C, additional axial stability can also be provided to the blocker 4300 by additional "leg" supports 4315 as an alternative to spring wire supports 4310. Another embodiment of a blocker shown in FIG. 15D, can include an external anchor 4320 that can be used, for example, with a blocker delivered through the left ventricular wall near the apex of the heart to the exterior of the heart.

In an embodiment shown in FIGS. 15E, 15F and 15G, the blocker 4500 includes one or more support wires 4510 extending proximally from the expandable region 4501 in addition to the distal anchor 4505. The support wires 4510 can be sized to engage the muscular annulus around the mitral valve MV as well as tissue of the left atrium LA. The support wires 4510 can be sharp or include barbs 4515 to hold onto the tissue. During delivery, the support wires 4510 can be retracted within a sheath or catheter and then relax or spring outward upon retraction of the sheath to engage the annulus or left atrium. The support wires 4510 can be sized to engage the annulus and/or the left atrial tissue.

Figure 15H:
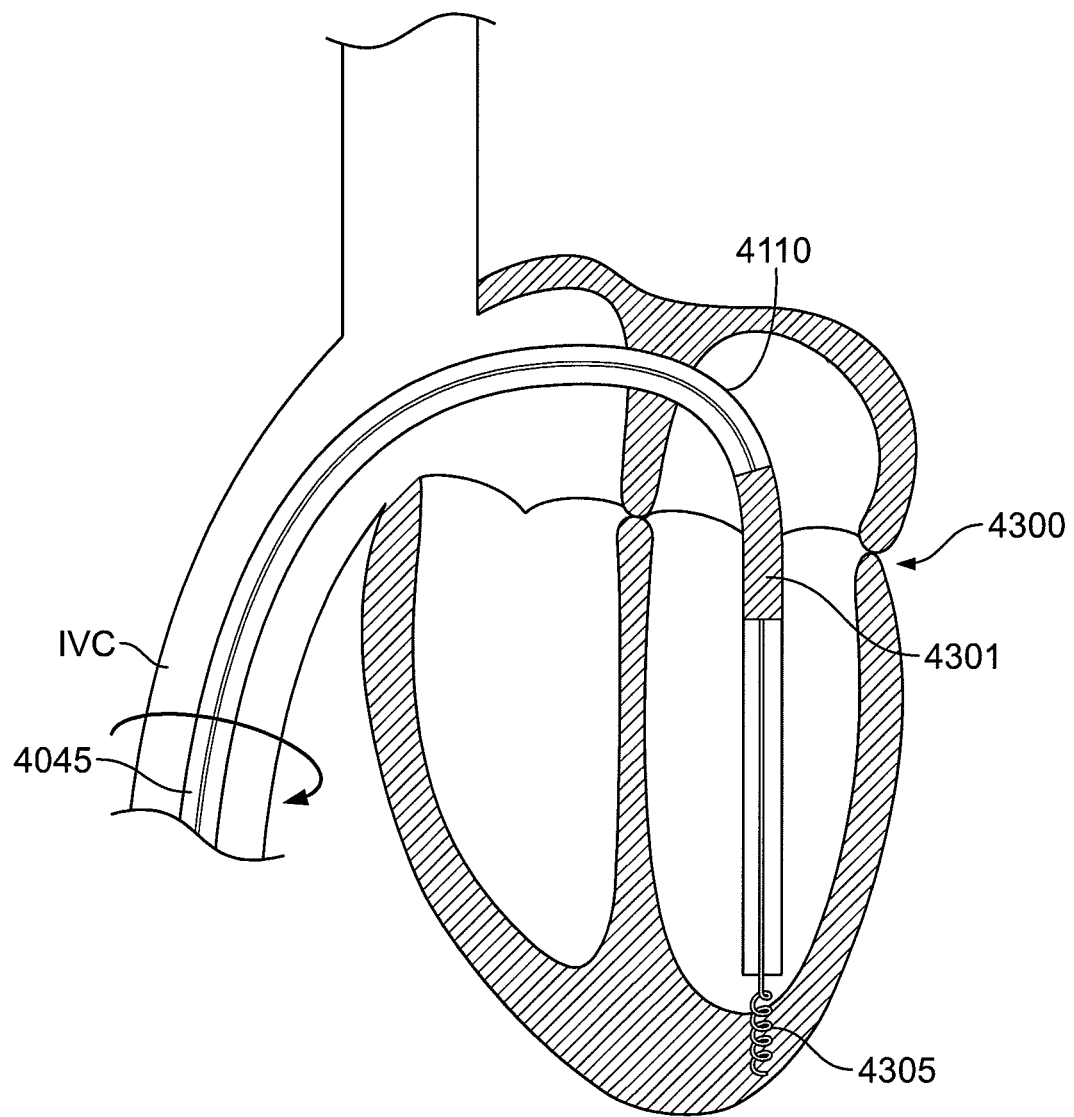
FIGS. 15H-15I show schematic, cross-sectional views of the heart illustrating a method of delivery of an anchored blocker.
Figure 15I:
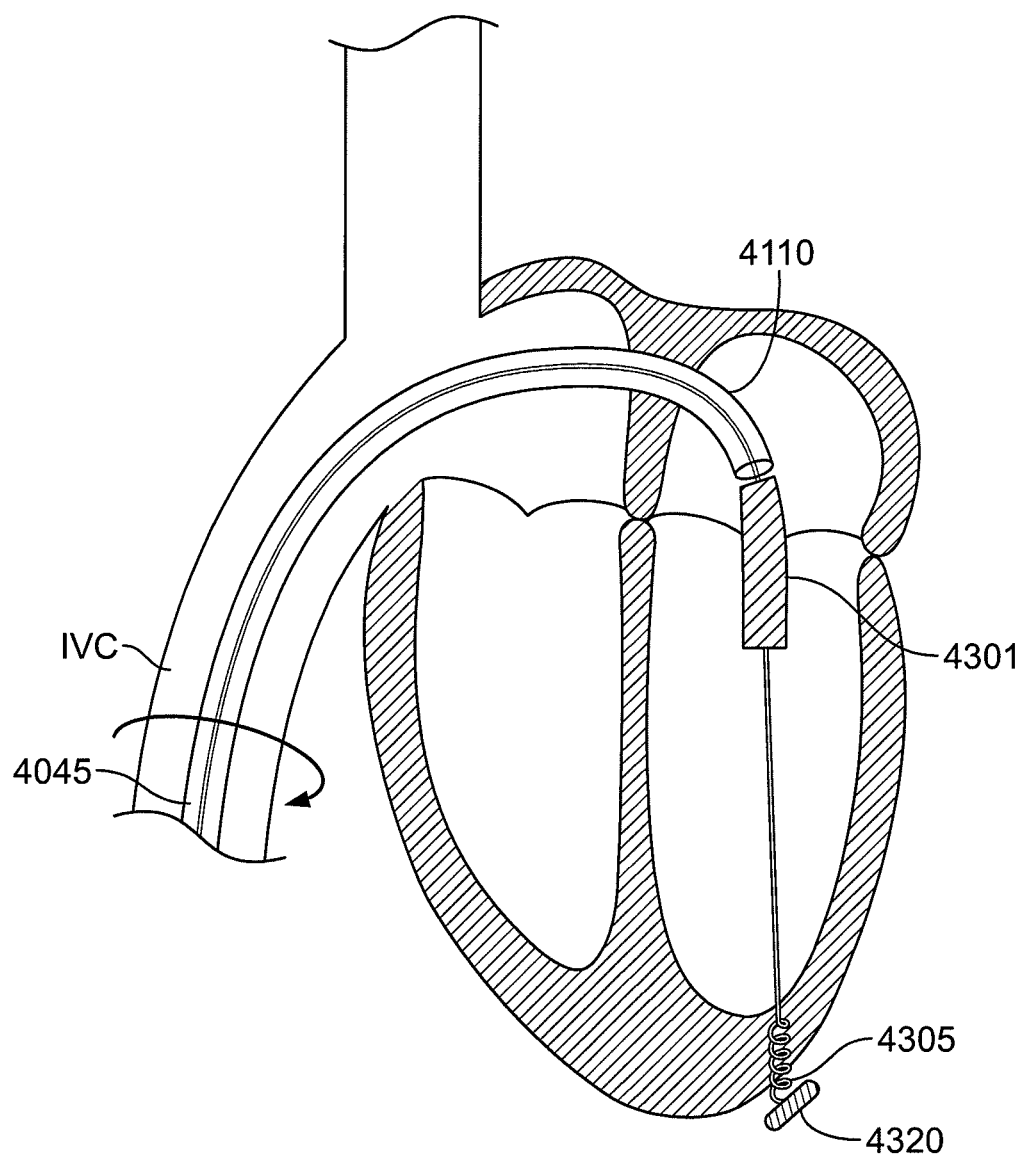

FIGS. 15H-15I show method of delivery of an anchored blocker, such as the blockers shown in FIGS. 15A-15G, using a catheter 4045 and a retractable sheath 4110 compressing the expandable region 4301 of the blocker 4300 to a delivery configuration inside an inner lumen of the sheath 4110. The catheter and sheath system having a compressed blocker therein can be advanced from a venous site, such as accessed from a femoral vein through the inferior vena cava IVC and across the interatrial septum to the mitral valve as is described herein. The catheter 4045 can be positioned using guidance methods such as echoguidance or other guidance method known in the art. The distal anchor of the blocker 4300 can extend out the distal end of the retractable sheath 4110 and come into contact with the ventricle wall upon advancement of the blocker 4300. The catheter 4045 can be rotated to advance the anchor 4305 into the left ventricle myocardium. The anchor 4305 can be embedded in the ventricle wall. An anchor 4320 can also be implanted that it is external to the heart (see FIG. 15I). An alternate delivery method can include through a small access port such as through the chest wall, such as through a mini-thoracotomy, and into the apex of the left ventricle. The device can be advanced from the left ventricle into the left atrium and then the sheath retracted to open the blocker. The surgeon can then implant an external anchor 4320 upon positioning the blocker between the valve leaflets and then close the access ports.

As shown in FIG. 15I, the blocker 4300 can self-expand upon retraction of the sheath 4110. The leaflets can then coapt against the blocker and prevent mitral regurgitation (MR). If the MR result is unsatisfactory in some way, the sheath 4110 can be re-advanced to compress the expandable portion 4301 of the blocker 4300. The catheter 4045 can then be rotated to either unscrew or screw the distal anchor 4305 and the distance between the blocker 4300 and the base of the ventricle wall modified. The blocker can be re-positioned, re-deployed and removed. If the MR result is satisfactory, the blocker can be detached from the catheter and the catheter and sheath retracted and withdrawn from the patient.

The expandable regions 4301, 4501 of the blockers 4300, 4500 described above can be inflatable bladders or made from a compliant material. It should be appreciated that other configurations of expandable regions are considered. It should also be appreciated that the anchors and supports described with respect to the blocker embodiments of FIGS. 15A-15I can be used with other embodiments of blockers described herein.

Figure 16A:
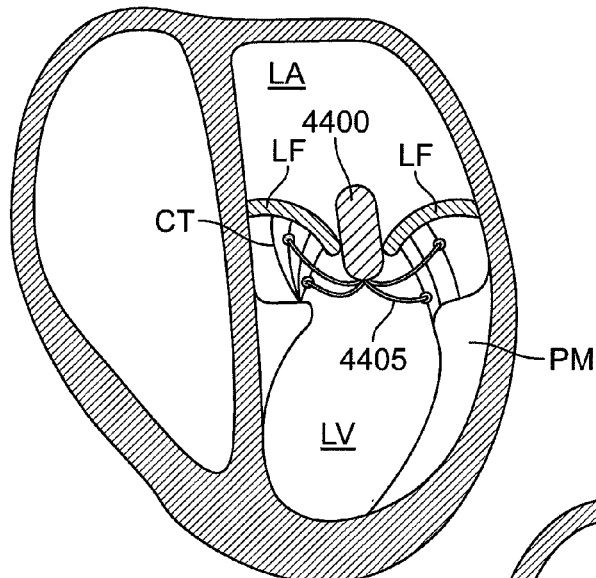
FIGS. 16A-16C show schematic cross-sectional views of the heart with other embodiments of a blocker in position wherein the blocker includes various anchoring mechanisms.
Figure 16B:
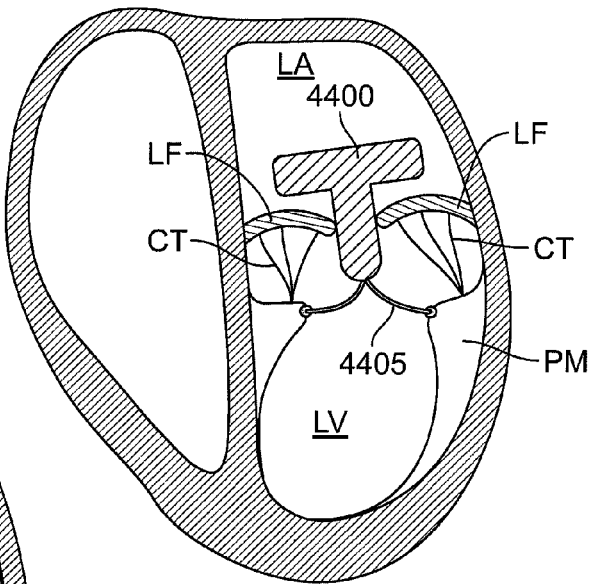
Figure 16C:
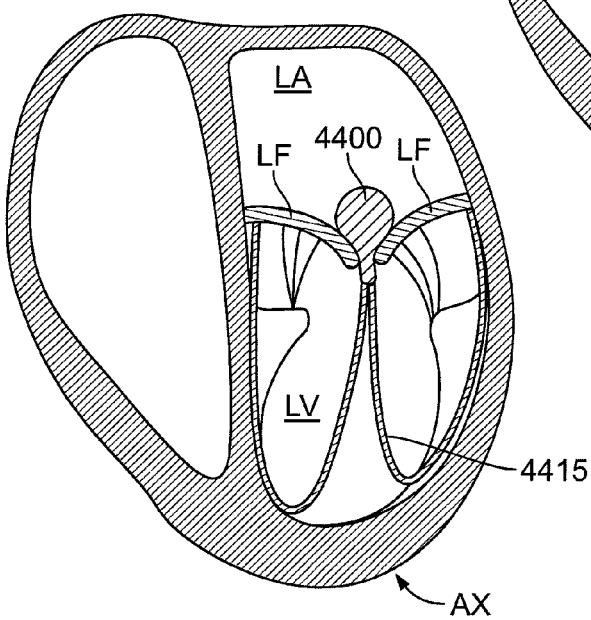

FIGS. 16A-16C show more embodiments of a blocker 4400 having a distal anchoring mechanism 4405. As shown in FIG. 16A, the blocker 4400 is held in place by distal anchors 4405 that attach to the chordae tendinae CT and/or papillary muscle PM. The anchors 4405 can include various attachments 4410 including loops that wrap around the CT or clips that attach to the PM. The embodiment of FIG. 16B shows a blocker 4400 where the geometry of the proximal region of the blocker 4400 further supports the blocker and prevents it from passing through the leaflets LF from the atrial side. This embodiment also shows an anchor 4405 (in this case a suture line attachment that attaches to the papillary muscle PM). The anchors 4405 and/or attachments 4410 can be shape-memory metal (e.g. Nitinol) with coil set shape that wrap around the chordae. Alternatively, the blocker 4400 can incorporate a rail system such that after the anchors 4005 are in place the blocker 4400 can be advanced over a guide wire or other rail system to slide the blocker 4400 into the desired location. The rail system can be used to lock on the anchors 4405 upon expansion. Various blocker anchoring mechanisms can be used and can be used in combination with any of the blocker embodiments described herein.

FIG. 16C shows an embodiment of a blocker 4400 incorporating another embodiment of a distal anchor system or support structure 4415. The support structure 4415 (e.g. wires, plastic elements or inflatable legs) can be advanced distally from the blocker 4400 such that it contacts the inner wall of the left ventricle LV near the apex AX. The support structure 4415 can curve back around up toward the valve structure, pressing against and pushing up from the apex AX and against the ventricle wall. The support structure 4415 can terminate under the leaflets LF against the ventricle wall. The blocker 4400 can lock the position of the support structure 4415 upon expansion.

The blockers of FIGS. 16A-16C can be contained within a catheter or sheath during delivery and advanced to the left atrium. The distal anchors 4405 can initially wrap around (or clip or pierce or insert, depending on the embodiment used) the chordae and/or papillary muscles PM before the blocker 4400 exits the catheter guide tube. The blocker 4400 can self-expand upon retraction of the catheter or sheath or be inflated prior to retraction of the catheter or sheath as described above. Expansion of the blocker 4400 can lock into position the chordae or PM attachment. Deflation or re-compression of blocker 4400 can allow movement and repositioning of the blocker. It should be appreciated that the catheter could also be advanced from a femoral site over the aorta through the aortic valve and retrograde to the mitral valve. The distal anchors 4405 can grasp and wrap around the chordae according to a variety of methods, for example such as described in U.S. Publication No. 2004-0030382, which is incorporated herein by reference in its entirety.

Blockers described throughout this disclosure can include a combination of anchor mechanisms. For example, the blockers can include either or both distal and proximal anchors. Such a combination of anchors provides additional axial stability, adjustability and positioning. The distal anchors as described above can attach, for example, to the ventricle wall or papillary muscle or chordae and the like. The proximal anchors of the blocker can attach to the annulus, the atrial wall, valve leaflets and/or the interatrial septum.

Figure 17B:
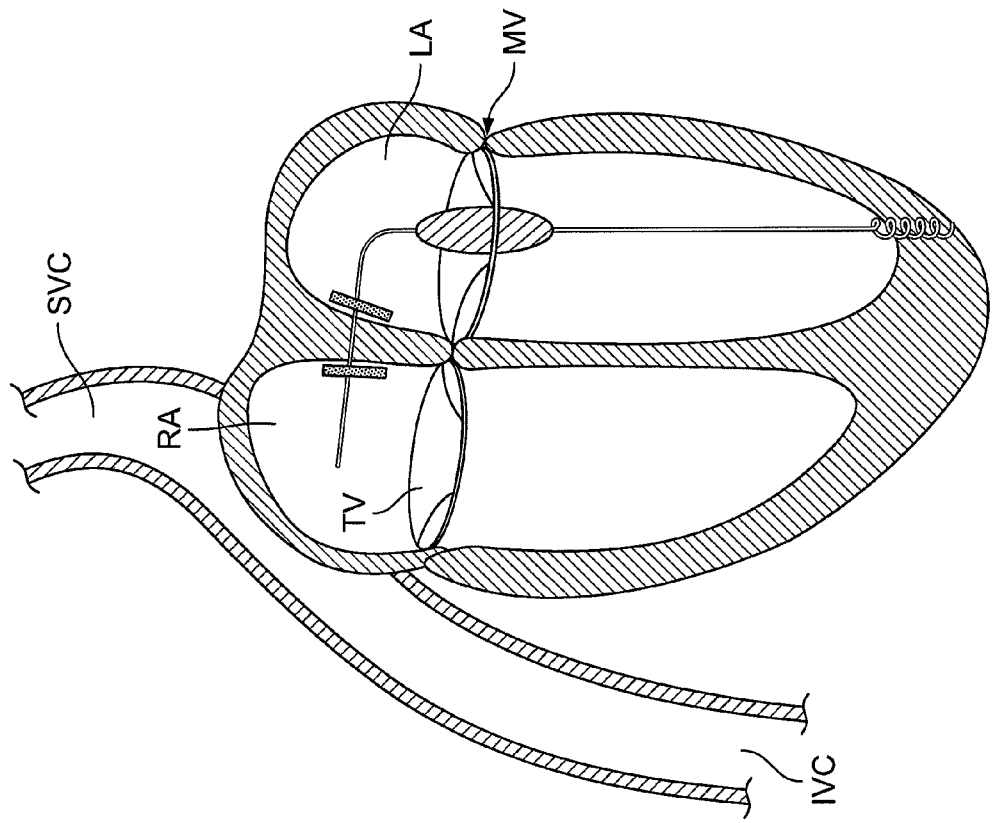
FIG. 17B shows a schematic cross-sectional view of a heart with the blocker device of FIG. 17A positioned within the mitral valve. The chordae tendinae and papillary muscles are not shown for clarity.
Figure 17A:
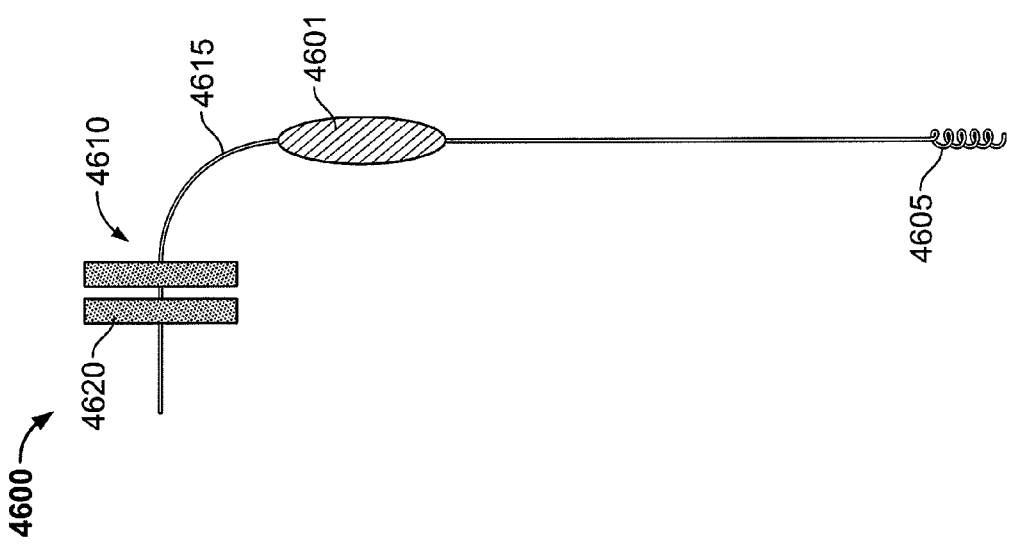
FIG. 17A shows a schematic side view of a blocker having another embodiment of a proximal anchoring mechanism.

In another blocker embodiment shown in FIG. 17A-17B, the blocker 4600 includes one or more of a proximal anchor mechanism 4610 and/or a distal anchor 4605. The proximal anchor can have a "clam-shell" or "double-umbrella" design configured to engage the septum between the left and right atria in the heart. The illustration provided in FIG. 17A includes both proximal and distal anchors; however, the use of only a proximal or only a distal anchor is contemplated. In an embodiment including a proximal anchor 4610, a wire 4615 extends from the expandable region 4601 to one or more septal anchors 4620. This mechanism provides adjustability of position to optimize the result. For example, the length of the wire 4615 can be adjusted by applying a proximally-applied force such that the wire 4615 slides in a proximal direction through the septum and the septal anchors 4620. A crimp or other clamping device can be advanced in a distal direction over the wire 4615 until it abuts a septal anchor 4620, for example the septal anchor 4620 in the right atrium. The crimp can be deployed such that it is affixed to a portion of the wire 4615 near the septal anchor 4620 and prevents the wire 4615 from sliding back through the septal anchors 4620. The wire 4615 can extend from a proximal portion of the expandable region 4601 of the blocker 4600. Alternatively, the wire 4615 can extend from the distal anchor 4605, through the expandable region 4601 and out the proximal end of the blocker 4600. In this embodiment, adjustment of the wire 4615 can also adjust the length of the wire 4615 between the anchor 4605 and the expandable region 4601 of the blocker 4600.

Figure 18C:
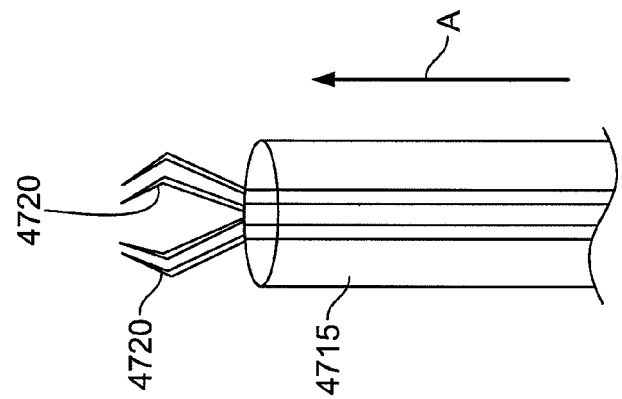
FIG. 18C shows the proximal anchoring mechanism of FIG. 18B in a clamped state.
Figure 18B:
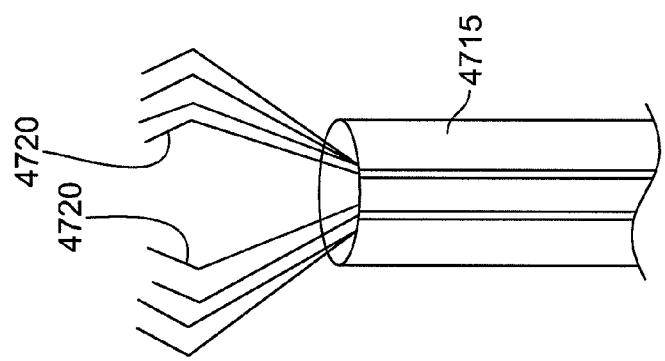
FIG. 18B shows the proximal anchoring mechanism of the blocker of FIG. 18A taken along circle B-B.
Figure 18A:
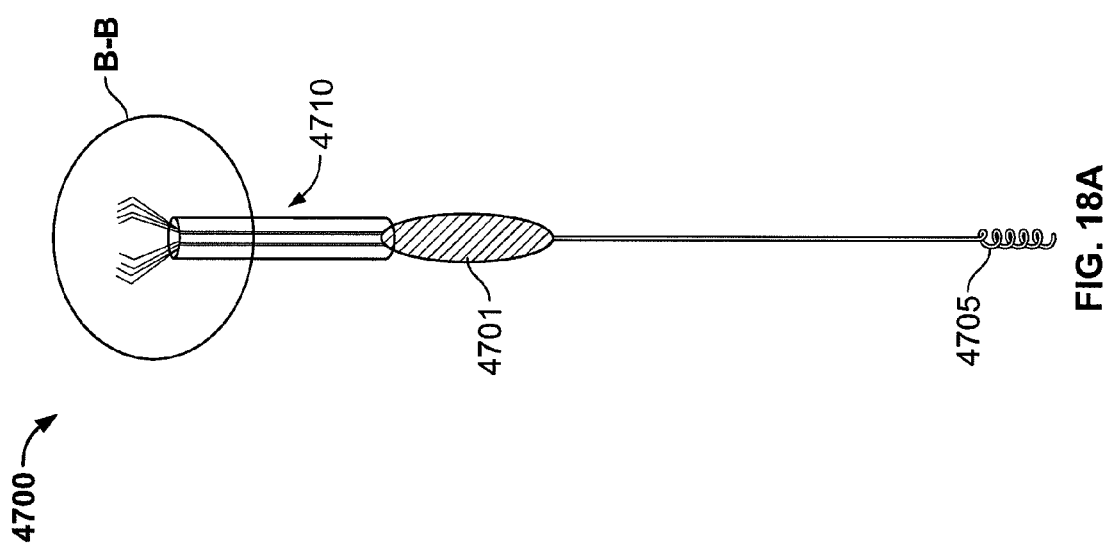
FIG. 18A shows a schematic side view of a blocker having another embodiment of a proximal anchoring mechanism.

An alternate proximal anchoring mechanism is shown in FIGS. 18A-18C). In an embodiment, an expandable blocker 4701 can include a proximal anchor mechanism 4710. As best shown in FIGS. 18B and 18C, the proximal anchor mechanism 4710 can include a sleeve 4715 that can be advanced and brings together one or more pairs of sharp angled wires 4720 that grab onto myocardium in either the ventricle or atrium or both. The blocker 4701 can be expanded such as by inflation such that it urges the sleeve 4715 in a proximal direction (arrow A). As the sleeve 4715 moves in the proximal direction, the inner walls of the sleeve 4715 presses against the pairs of angled wires 4720 moving them towards one another. As the angled wire pairs 4720 move together any tissue positioned therebetween will be captured and the device clamped in place. The diameter of the expanded blocker 4701 can be larger than the inner diameter of the sleeve 4715. This prevents the sleeve 4715 from being retracted in the distal direction back over the blocker 4701. Thus, the expanded blocker 4701 can simultaneously block regurgitation through the valve leaflets, deploy the proximal anchor and lock the proximal anchor in place.

To re-position the blocker system, the expandable blocker 4701 can be depleted of filling material such that the outer diameter of the expandable blocker 4701 is reduced and the sleeve 4715 can be withdrawn or retracted over the outer diameter of the blocker 4701. The embodiment of FIG. 18A is shown having a distal anchor 4705, but it should be appreciated that the embodiment need not include a distal anchor.

Figure 18D:
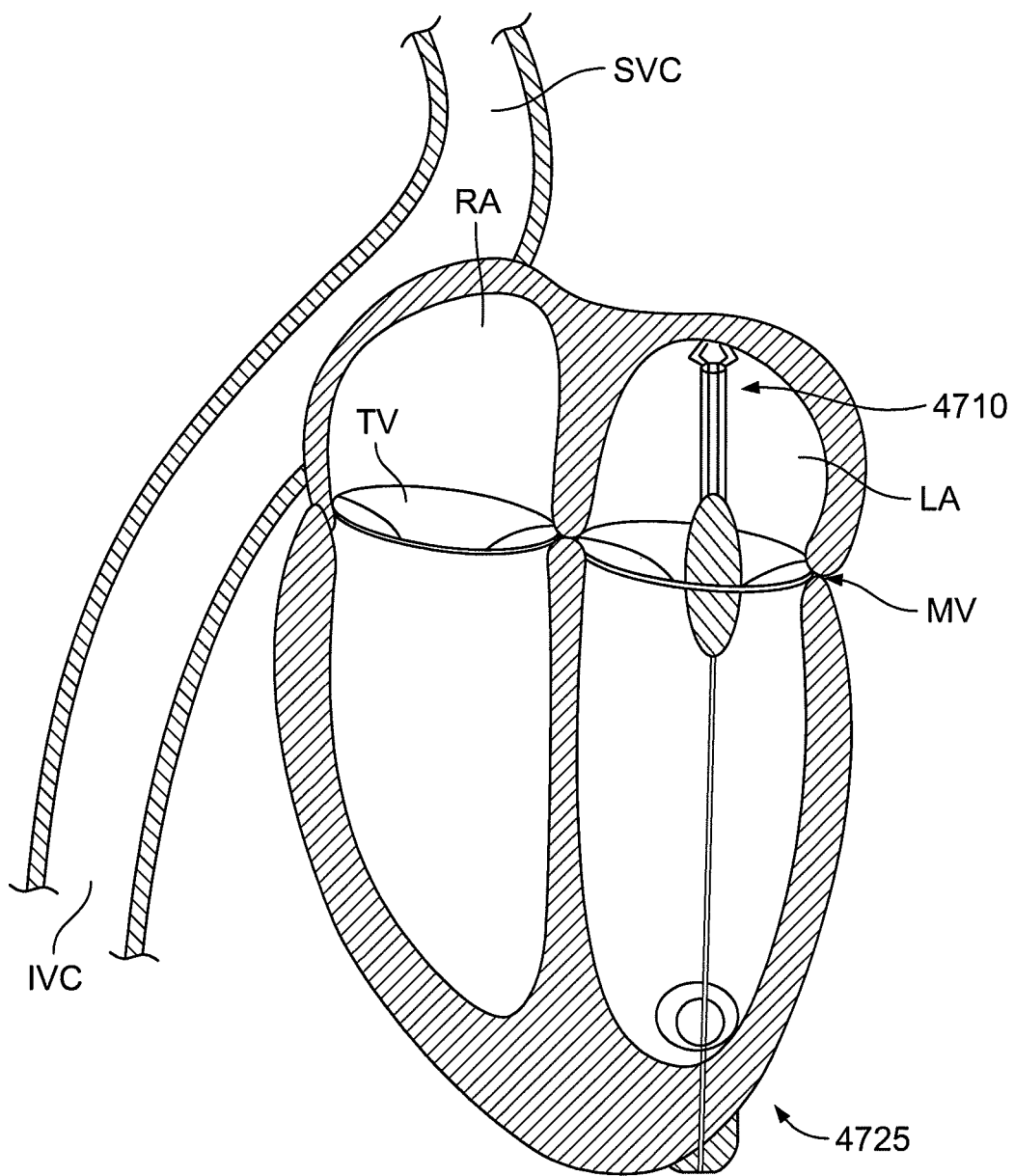
FIG. 18D shows a schematic cross-sectional view of a heart with the blocker device of FIG. 18A positioned within the mitral valve. The chordae tendinae and papillary muscles are not shown for clarity.

FIG. 18D shows another embodiment of a blocker 4700 incorporating both a proximal anchoring mechanism 4710 as well as a distal septal anchor 4725; however, it should be understood that the blocker may include only the distal anchor 4725, only the proximal anchor 4710, or both proximal and distal anchors.

Figure 19A:
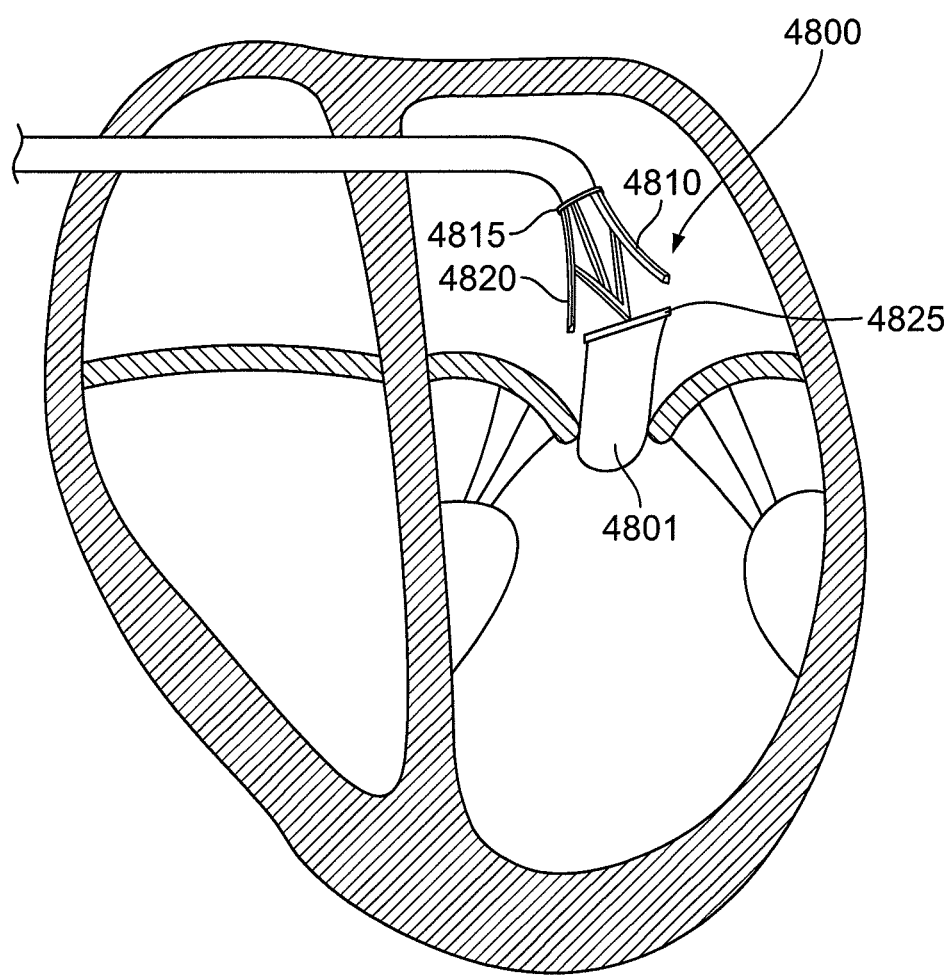

FIGS. 19A-19C show another embodiment of a proximally-anchored blocker system 4800. The blocker system 4800 includes a blocker 4801 which may be any of the blockers disclosed throughout this disclosure. Thus, the blocker 4801 may be formed of a resilient material and/or may be a liquid or gas-filled bladder. Upon positioning of the blocker 4801 between the leaflets such that the blocker 4801 provides a desired amount of coaptation between the leaflets, an anchor system 4810 can be actuated. The anchor system 4810 can include an anchor wire lock ring 4815, a plurality of support arms 4820 and a blocker lock ring 4825.

The anchor system 4810 deploys in a manner similar to an umbrella's arms. The anchor wire lock ring 4815 can be slid proximally and distally to spread or retract the support arms 4820. The support arms 4820 can be made of a shape memory material such as Nitinol or the like such that the support arms are biased to extend or spread. Alternatively, a biasing member (not illustrated) such as a spring or the like can be used to bias the support arms 4820 to extend. Further still, the anchor system 4810 can omit a biasing member such that support arms 4820 can be manually opened by extending the ring 4815.

The support arms 4820 can anchor to the atrial side of the valve such as by grasping or penetrating the annulus or other structures near the valve, such as with barbs 4818 or other features that improve the grip of the support arms 4820 to the adjacent anatomy. The support arms 4820 can also anchor due to a spring force or pushing out against the atrial wall. The support arms 4820 can also have a length that is adjustable, for example, the support arms 4820 can slide through the anchor lock ring 4815 such that arm length can be adjusted for proper contact with the adjacent structures. Such a configuration can be self-adjusting. The anchor lock ring 4815 can lock onto the blocker lock ring 4825 to fix the blocker 4800 in its deployed state, such as by a snap-lock type configuration.

Figure 20:
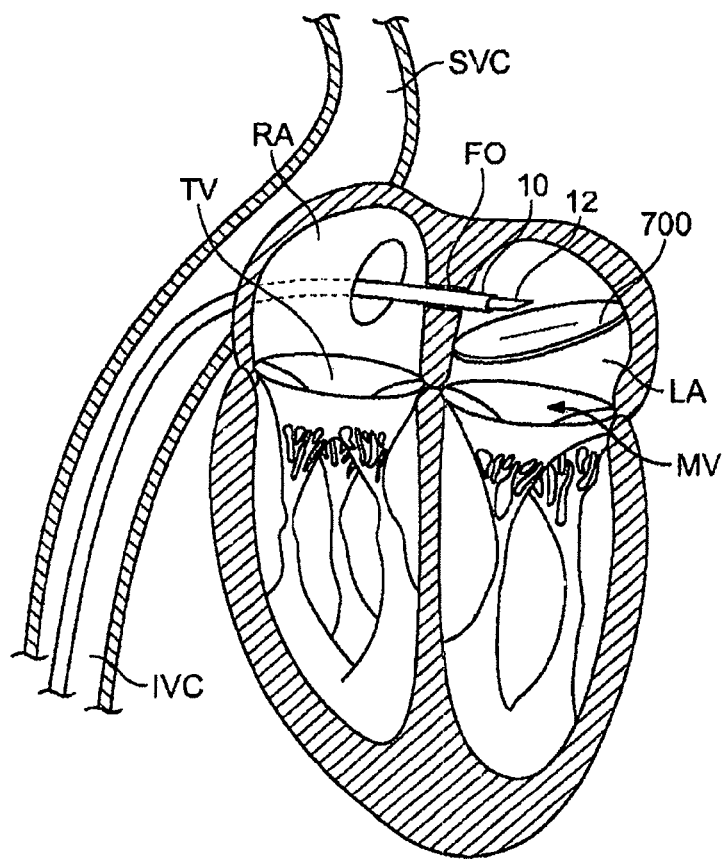
FIG. 20 shows a cross-sectional view of the heart wherein a one-way valve device is located in the left atrium.

FIG. 20 shows a cross-sectional view of the heart wherein a one-way valve device 700 is located in the left atrium. The valve device is represented schematically in FIGS. 21A-B. A corresponding method of treating heart disease includes introducing a one-way valve device 700 into the left atrium of an individual's heart proximal the mitral valve. The valve device 700 is configured to permit fluid flow in one direction while preventing fluid flow in an opposite direction. The valve device can have various structures. For example, the device can comprise a valve that is mounted on a stent that is sized to be positioned in the left atrium. Valves that may be used, for example may be stentless valves such as the TORONTO SPV® (Stentless Porcine Valve) valve, mechanical or tissue heart valves or percutaneous heart valves as are known in the art. The outer wall of the one-way valve device is sealed to the inner wall of the atrium so that a fluid-tight seal is formed between the outer wall of the one-way valve device and the inner wall of the left atrium. In this regard, the valve device can include a seal member that is configured to seal to the inner wall of the atrium.

Figure 21A:
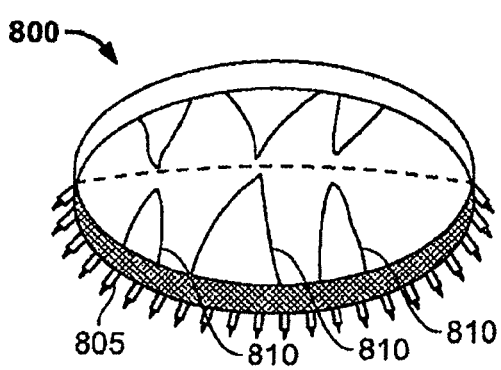
FIG. 21A shows a prosthetic ring that is sized to fit within a mitral valve.
Figure 21B:
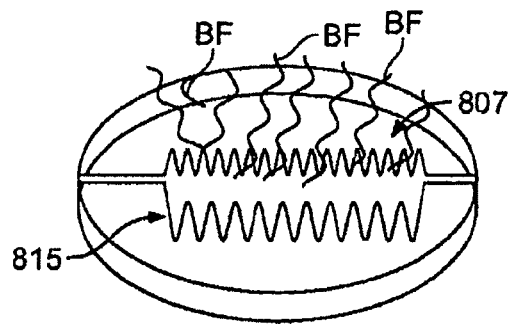
FIG. 21B shows another embodiment of a prosthetic ring wherein a one-way valve is positioned inside the ring.

Another embodiment involves a prosthetic for treating heart disease in general and defective or diseased mitral valves in particular. FIG. 21A shows a prosthetic ring 800 that is sized to fit within a mitral valve annulus The ring 800 includes one or more anchors 805 that extend around the periphery of the ring 800. In addition, one or more struts 810 struts extend across the diameter of the ring, and can be made of a material that includes shape-memory metal (e.g. Nitinol) or magnetic wires for selectively adjusting the shape of the ring. The struts can also be instrumental in baffling mitral valve leaflet "flail". FIG. 21B shows another embodiment of a prosthetic ring 807 wherein a one-way valve 815 is positioned inside the ring such that blood flow BF can flow through the valve in only one direction. The valve can be manufactured of various materials, such as silicone.

Figure 22:
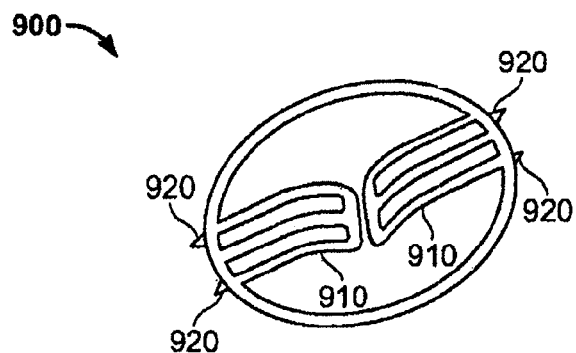
FIG. 22 shows a prosthetic with one or more tongues or flaps that are configured to be positioned adjacent the flaps of the mitral valve.

FIG. 22 shows a prosthetic with one or more tongues or flaps 910 that are configured to be positioned adjacent the flaps of the mitral valve. The prosthetic includes a ring 900 sized to fit within a mitral valve annulus. At least two tongues 910 project from the ring 900 in a caudal direction when the ring is implanted into a heart of an individual. The ring 900 is flexible between an expanded configuration and a contracted configuration and is biased toward the contracted configuration. One or more anchors 920 protrude from the flexible ring 900 for coupling the ring coaxially to the annulus such that the contracted configuration of the ring exerts an inward force to the annulus. Alternatively, or in addition, the two tongues 910 can each have a length sufficient to prevent prolapse of a mitral valve when the ring is placed atop the leaflets of the mitral valve. In a further embodiment the tongue elements may be attached at a central point.

Figure 24:
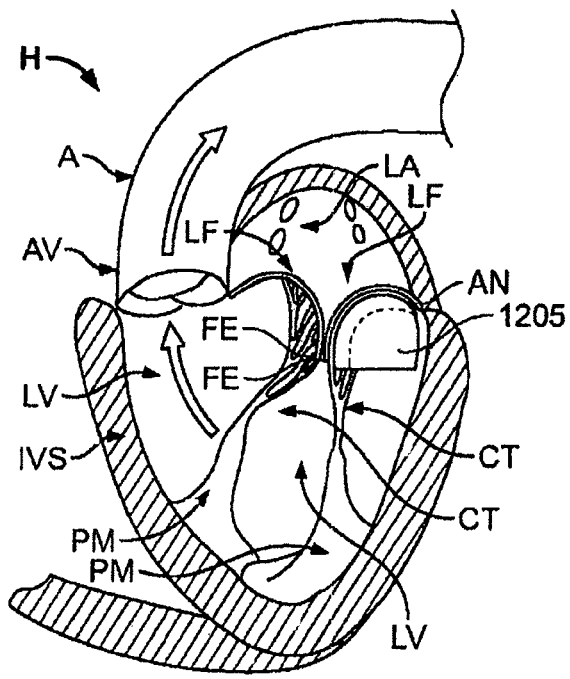
FIG. 24 shows a schematic, cross-sectional view of the heart with a wedge positioned below at least one of the leaflets of the mitral valve.

In yet another embodiment, a prosthetic for treating heart disease in general and a defective or diseased mitral valve in particular includes a wedge 1205 used to support the leaflet and/or prevent prolapse or flail of the leaflet. The wedge 1205 may be implanted on either the ventricular side of the leaflet. FIG. 24 depicts the wedge 1205 on the ventricular side of the leaflet. According to one embodiment, the wedge 1205 has a length that is up to a length of the line of coaptation of a mitral valve. In an embodiment, the wedge 1205 has a length that is as long as the leaflet segment needing support.

The wedge can have a depth sufficient to prevent prolapse of a mitral valve when the wedge is placed atop an annulus of the mitral valve along the line of coaptation, and may provide a point of coaptation for each leaflet. One or more anchors can protrude from the wedge for coupling the wedge to the annulus of the mitral valve. Methods of treatment using the wedge are also disclosed. The methods include inserting the wedge into an individual's heart, placing the wedge lengthwise along the line of coaptation of the mitral valve. The wedge is then secured to an annulus of the mitral valve along the LV wall. The wedge may be positioned also just under one segment of the leaflet (likely P2 or P3 in the case of functional MR).

Figure 23A:
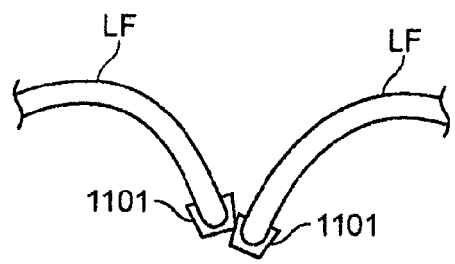
FIG. 23A shows an exemplary embodiment of one or more clips that are positioned on free edges of the leaflets.

In yet another embodiment, a device for treating heart disease includes a clip for attachment to a free end of a heart valve leaflet. FIG. 23A shows an exemplary embodiment of one or more clips 1101 that are positioned on free edges of the leaflets LF. Each of the clips 1101 has a shape that prevents flail of the leaflet by catching against an underside of an opposing leaflet. Methods of treatment using the clip are also disclosed. The methods include introducing the clip into an individual's heart and attaching the clip to a free end of a heart valve leaflet opposite the free end of an opposing leaflet of the heart valve so that the clip catches to the underside of the opposing leaflet during systole. In a further embodiment, a clip may be placed on both leaflets such that the clips meet or catch when the leaflets are in proximity. The clips may attach momentarily during systole, and then detach during diastole, or may clip permanently resulting in a double orifice mitral valve anatomy. The clips of this embodiment may include a magnetic element, or one may be magnetic and the other of a metal material attracted to said magnetic field of the magnetic clip.

Figure 23B:
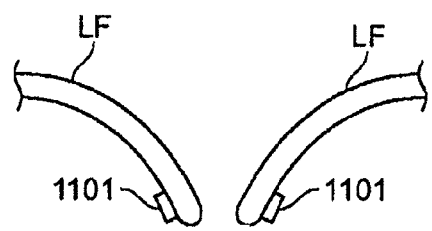
FIG. 23B shows pair of leaflets with a magnetic clip attached to the underside of each leaflet.
Figure 23C:
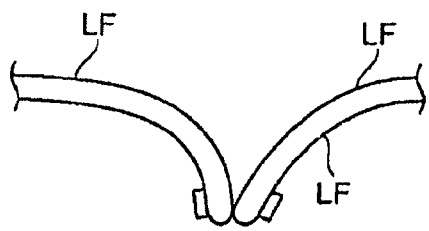
FIG. 23C shows the leaflets coapted as a result of the magnetic attraction between the magnetic clips.

In the case of magnetic clips, the clip elements may be placed on the underside of the leaflets (e.g. not necessarily on the free edge of the leaflet), provided that the magnetic field of the clip is sufficient to attract the opposing magnetic or metal clip element. This is further described with reference to FIG. 23B, which shows pair of leaflets LF with a clip 1101 attached to the underside of each leaflet. At least one of the clips is magnetic, while the other clip is of an opposite magnetic polarity than the first clip or of a metal attracted to the magnetic field of the first clip. The magnetic field is sufficiently strong such that the clips 1101 can attach to one another either momentarily or permanently to coapt the leaflets, as shown in FIG. 23C.

Figure 23D:
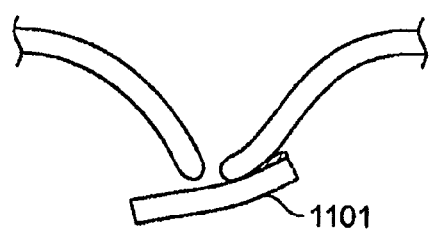
FIG. 23D shows a pair of leaflets with a single clip attached to one of the leaflets.

In another embodiment, shown in FIG. 23D, a single clip 1101 is attached to one of the leaflets. The clip 1101 is sufficiently long to increase the likelihood that the clip 1101 will coapt with the opposite leaflet.

In yet another embodiment, a device for treating heart disease includes a wedge for placement under a heart valve leaflet. FIG. 24 shows a schematic, cross-sectional view of the heart with a wedge 1205 positioned below at least one of the leaflets of the mitral valve. The wedge 1205 can be positioned below one or both of the leaflets. The wedge 1205 is sized to fit under the valve leaflet and caudal the annulus of the heart valve. The wedge 1205 can have a shape that is contoured so as to provide support to a lower surface of the leaflet. (In FIG. 24, the left atrium is labeled LA and the left ventricle is labeled LV.) An anchor is attached to the wedge for coupling the wedge to a wall of the heart chamber adjacent the heart valve. The wedge forms a fixed backstop against the bottom side of the heart valve leaflet, thereby providing a location for the leaflet to coapt against, and/or providing support or "pushing up" a restricted leaflet.

Other embodiments are directed to altering the size, shape, chemistry, stiffness, or other physical attributes of heart valve leaflets. In one embodiment in particular, a method of treating heart disease includes obtaining access to a heart valve leaflet and injecting a stiffening agent into the leaflet to stiffen the leaflet and minimize flail.

Other embodiments are directed to the chordae that connect heart valve leaflets to the inner walls of the heart. In one embodiment in particular, a method of treating heart disease includes obtaining access to a heart valve chord and cutting it mechanically or with energy such as a laser, or by heating the chordae to elongate them, thereby allowing the previously restricted leaflet to be less restricted so that it can coapt with the opposing leaflet.

In another embodiment directed to the chordae that connect heart valve leaflets to the inner walls of the heart, a cam-shaped ring is disclosed. The cam-shaped ring is sized to fit within a left ventricle of a heart. The ring forms a hole that is sized to receive two or more chordae tendineae. The ring is formed by connecting two detachable ends of the ring.

Methods of treatment using the cam-shaped ring are also disclosed. One method in particular includes introducing the ring into a left ventricle of a heart. One or more chordae tendineae are then surrounded by the ring, and the two ends of the ring are then attached to form a closed ring around the chordae tendineae. The ring is then rotated such that one or more of the chordae tendineae are shifted away from their initial orientation by the rotation of the cam-shaped ring. The ring may then be fixed in the rotated or tightened position.

Figure 25A:
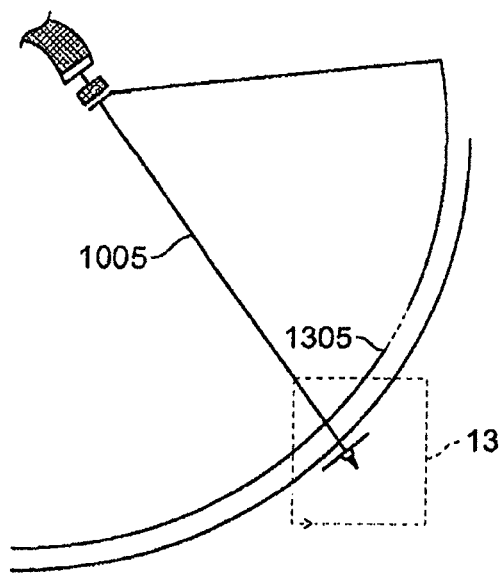
FIG. 25A shows an artificial chordae tendon.

An embodiment directed at the chordae of heart valve leaflets is now described. FIG. 25A shows a device that can be used to alter a chordae. A method includes obtaining access to a chordae tendinea (chord) within an individual's heart chamber. The chordae is then cut at a point along its length so that a length of the chorda tendinea is freed from the heart chamber leaving behind a length of chorda tendinea having a free end and an end attached to an edge of a heart valve.

With reference to FIG. 25A, a synthetic chord 1005 of greater length than the free length of chordae is introduced into the heart chamber. One end of the synthetic chordae 1005 is connected to a wall 1305 of the heart chamber or to a muscle attached to the wall of the heart chamber. Another end of the synthetic chord is attached to the free end of the chorda tendinea or to the leaflet.

Figure 25B:
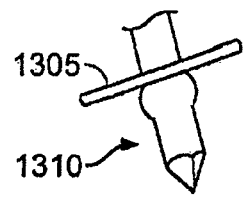
FIGS. 25B and 25C show attachment devices for attaching the artificial chordae tendon to a heart wall.
Figure 25C:
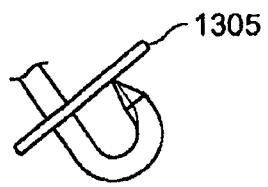

In this regard, the end of the chord 1005 that is attached the wall 1305 can have any of a variety of devices that facilitate such attachment. FIGS. 25B and 25C show enlarged views of attachment devices contained within box 13 of FIG. 25A. The attachment devices can be used to attach the chord 1005 to the wall 1305. In FIG. 25B, the attachment device 1310 is an enlarged ball having a distal trocar for penetrating the wall 1305. In FIG. 25C, the attachment device 1310 is a hook that is configured to penetrate through the wall 1305. It should be appreciated that the attachment device 1310 can have other structures and it not limited to the structures shown in FIGS. 25B and 13C. In variations of these embodiments, it may be advantageous to adjust the length of the chordae (synthetic, or modified), determine the therapeutic effect of the shortening or lengthening, and then fix the chordae at the most efficacious location.

Figure 26:
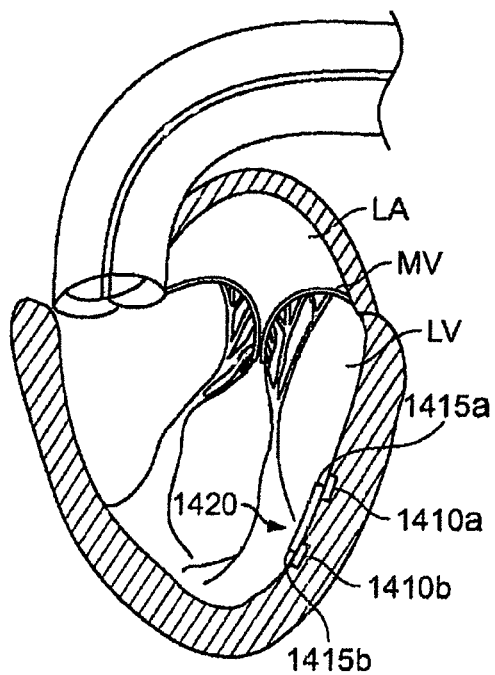
FIG. 26 shows a cross-sectional view of the heart with a first and second anchor attached to a wall of the heart.

Other embodiments are directed to atrial or ventricular remodeling to alter the shape of an atrium or ventricle. FIG. 26 shows a cross-sectional view of the heart with a first and second anchor attached to a wall of the heart. The system includes a first anchor 1410a having a screw portion 1415 for screwing into a wall of the heart and a connector portion. The connector portion is rotatable around an axis of rotation. The first anchor includes a power source to power rotation of the connector portion and a receiver for receiving telemetric signals from an external controller for controlling the rotation of the connector portion. The system includes a second anchor 1410b having a screw portion 1415b for screwing into a wall of the heart and a connector portion. Also included is a tether 1420 having two free ends. One of the free ends is coupled to the connector portion of the first anchor, and the other free end is coupled to the connector portion of the second anchor. An external controller is also included. The external controller has a telemetric transmitter for communicating with the receiver and controls the rotation of the connector portion. Alternatively, the anchors may be placed with a torqueable catheter.

In another embodiment, a method of altering a geometry of a heart includes introducing a first coupler into a heart chamber. The first coupler has an anchor portion and a connector portion. The connector portion is rotatable around an axis of rotation and is connected to a power source to power rotation of the connector portion. The power source is in communication with a telemetric signal receiver. The first coupler is secured to the wall of the heart chamber by anchoring the anchor portion to the wall. A second coupler is introduced into the heart chamber. The second coupler includes an anchor portion and a connector portion. The second coupler is secured to the wall of the heart chamber by anchoring the anchor portion to the wall at a distance from the first coupler.

A tensile member is introduced into the heart chamber. One end of the tensile member is connected to the connector portion of the first coupler, and another end of the tensile member is connected to the connector portion of the second coupler. The distance between the first and second couplers is adjusted by transmitting a telemetric signal to the receiver, thus causing the connector portion to rotate around the axis of rotation and threading the tensile member around the connector portion to reduce the distance between the first and second couplers.

In another embodiment, a system for altering the geometry of a heart chamber includes a planar tensile member having substantially inelastic material. At least two anchors are included for anchoring the planar tensile member to an inner wall of a heart chamber. The planar tensile member is substantially shorter in length than a left ventricle of a heart so that when the planar tensile member is anchored in a caudal direction along a length of the left ventricle a tensile force exerted by the planar tensile member between the two anchors prevents the left ventricle from dilating caudally.

In another embodiment, a method for altering the geometry of a heart includes providing a tensile member having a substantially inelastic material. The tensile member is substantially shorter in length than a left ventricle of a heart. The tensile member is inserted into the left ventricle of the heart and a proximal end of the tensile member is anchored to the left ventricle adjacent the mitral valve. A distal end of the tensile member is anchored to the left ventricle caudal the proximal end so that a tensile force exerted by the tensile member between the two anchors prevents the left ventricle from dilating caudally.

Figure 27:
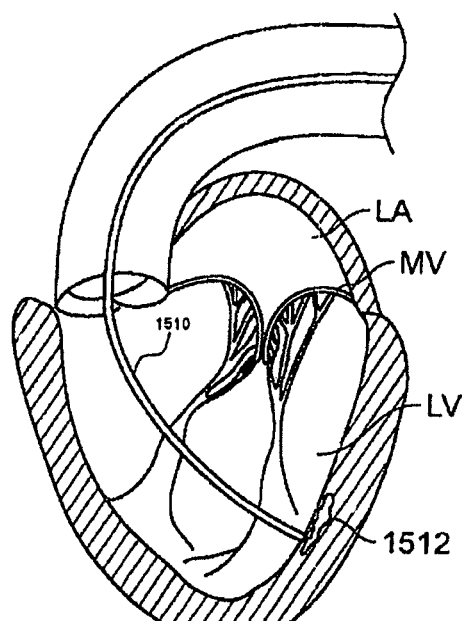
FIG. 27 shows a catheter that has been introduced into the heart.

Other embodiments are directed to strengthening or reshaping the left ventricle of the heart. In one embodiment in particular, a method of reinforcing the left ventricle includes injecting a strengthening agent into a wall of the left ventricle in an enlarged region of the ventricle, as shown in FIG. 27. FIG. 27 shows a catheter 1510 that has been introduced into the heart. The catheter 1510 has an internal lumen through which the strengthening agent 1512 can be injected. A proximal end of the catheter is connected to a source of the strengthening agent and a distal end of the catheter is configured to release the strengthening agent. As shown in FIG. 27, the distal end of the catheter is positioned at or near a wall of the heart and the strengthening agent 1512 is injected into the wall of the heart.

In another embodiment, a method is directed to altering the geometry of a heart. The method includes injecting a polymerizing agent into a pericardial space adjacent a left ventricle, thereby exerting a medial (inward) force against the left ventricle.

In yet another embodiment, a method of altering the geometry of a heart includes inserting a balloon into a pericardial space adjacent to a left ventricle of the heart, or extend into the pericardium of the heart. The balloon is inflated by injecting it with a fluid, and it exerts a medial force against the left ventricle upon inflation. In certain embodiments, the balloon can be inflated at the time of implantation, or at a later time. If inflated at a later time, the balloon would be self-sealing, and may be inflated by accessing the balloon with a needle placed through the chest wall.

Figure 28:
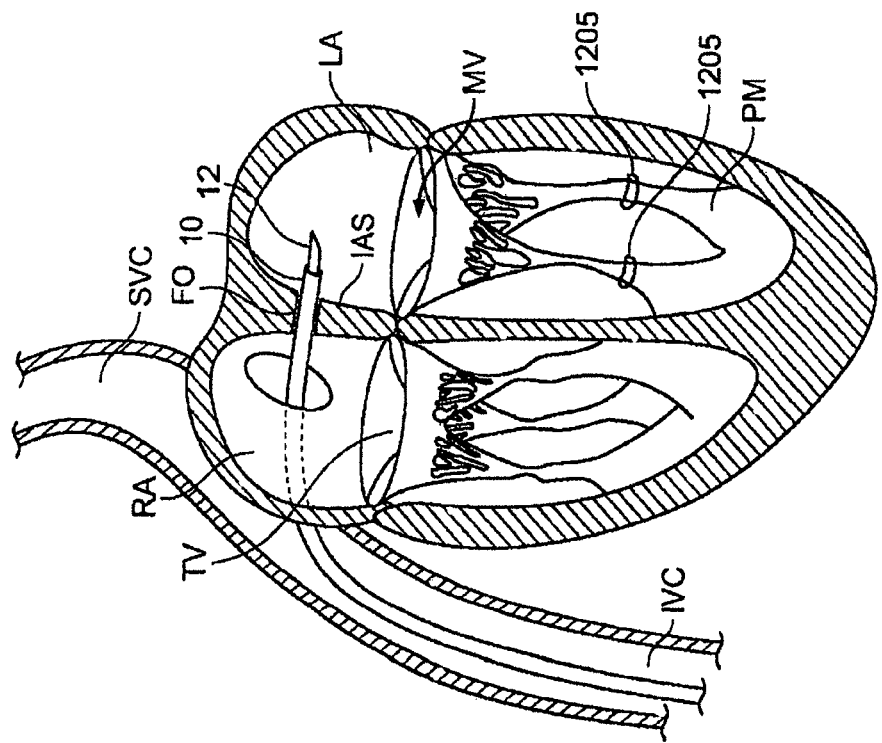
FIG. 28 shows a schematic view of a papillary muscle with a ring positioned over the muscle.

Other embodiments are directed to adjusting the length or orientation of papillary muscles. FIG. 28 shows a schematic view of the heart showing the papillary muscles PM. With reference to FIG. 28, a method of treating heart disease includes inserting an anchor, cuff or sleeve 1205 into the left ventricle of an individual's heart, and sliding a cuff or sleeve around a papillary muscle PM. The size of the cuff or sleeve is reduced so that the cuff or sleeve squeezes the papillary muscle. As the size of the cuff or sleeve is reduced, the papillary muscle stretches and increased in length.

In yet another embodiment, a method of treating heart disease includes obtaining access to a papillary muscle in a left ventricle of the heart. The papillary muscle is cut and reattached at a new location on an inner wall of the ventricle closer to the mitral valve.

Figure 29:
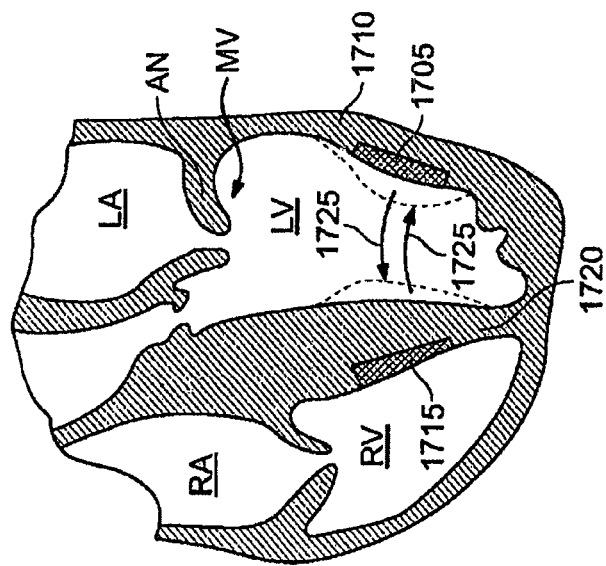
FIG. 29 shows a cross-sectional view of the heart with one or more magnets attached to a wall of the left ventricle.

Additional embodiments that employ magnets in the heart are now described with reference to FIGS. 29-31, which show cross-sectional views of the heart. With reference to FIG. 29, in one embodiment one or more magnets 1705 are implanted or otherwise attached to a wall 1710 of the left ventricle LV. One or more other magnets 1715 are implanted or otherwise attached to a wall 1720 of the right ventricle. The magnets 1705 and 1715 are attached to the walls 1710 and 1720 such that they assert an attractive magnetic force (as represented by the arrows 1725 in FIG. 29) toward each other. The magnetic force 1725 assists in remodeling of the left ventricle during pumping of the heart. That is, the magnets 1705 and 1715 are urged toward one another (thereby also urging the walls 1710 and 1720 toward one another) to re-shape either the annulus AN or the left ventricle LV. The annulus or the left ventricle LV are re-shaped in a manner that reduces or eliminates backflow through the mitral valve MV. It should be appreciated that a similar procedure can be performed on the right ventricle RV and associated valves.

Figure 30A:
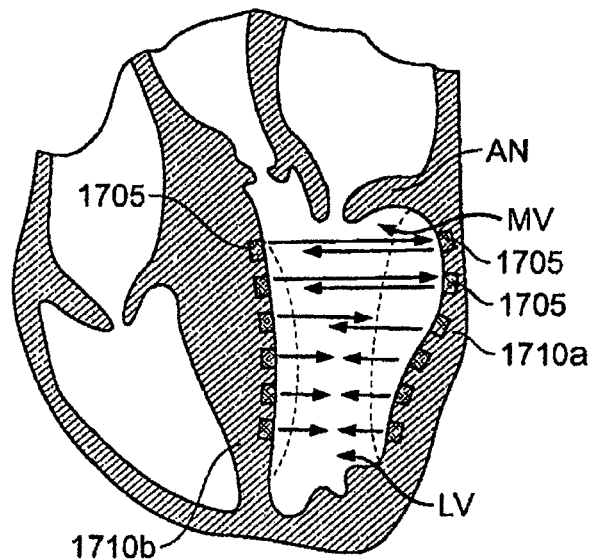
FIG. 30A shows another embodiment of a procedure wherein magnets are implanted in the heart to geometrically reshape the annulus or the left ventricle.

FIG. 30A shows another embodiment of a procedure wherein magnets are implanted in the heart to geometrically reshape the annulus or the left ventricle. One or more magnets 1705 are implanted or otherwise attached to a first wall 1710*a* of the left ventricle LV. One or more magnets 1705 are also implanted or otherwise attached to a second, opposed wall 1710*b* of the left ventricle. The magnets on the opposed walls 1710*a*, 1710*b* exert an attractive magnetic force toward one another to draw the walls 1710*a*, 1710*b* toward one another and re-shape the left ventricle LV or the annulus AN.

Another embodiment of a procedure uses magnets to anchor tethers within the heart at various locations to optimize the shape of cardiac structures to improve cardiac function. The tethers are placed to either reshape the cardiac structure or to prevent dilatation of the structure over time. The tethers must be securely anchored to the heart structures. A method of anchoring which enables tethering in various positions and directions within the cardiac structures is important for the clinician to optimize cardiac reshaping based on each individual patient anatomy and disease state. A method of anchoring which is atraumatic is also desirable.

Figure 30B:
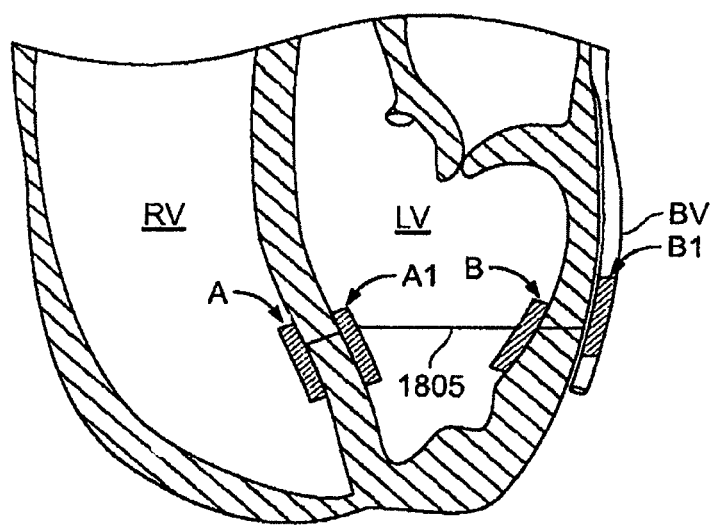
FIG. 30B shows the heart wherein tethered magnets are implanted in various locations to geometrically reshape the annulus or the left ventricle.

FIG. 30B shows a side view of the heart with sets of magnets A, A1, B, and B1 positioned to various locations of the heart or to anatomical structures adjacent the heart. In one embodiment, at least one magnet A is placed on the interventricular septum within the right ventricle RV. At least one magnet A1 is placed within the left ventricle LV opposite magnet A. The magnetic force between A and A1 maintains the position of the magnets. The magnets may be enclosed in materials that will promote tissue in-growth and healing to the interventricular septum to ensure stability of location and to eliminate the need for long term anti-coagulation. Additionally, the enclosure material which is flexible and can be delivered in a low profile can be significantly larger in size than the magnets to increase the surface area of contact with the heart wall which will increase the tension that can ultimately be placed on the anchor over time.

A second set of magnets B and B1 are then delivered to another location selected within or adjacent to the heart. The set of magnets A/A1 are attached to the set of magnets B/B1 using at least one tether 1805, as shown in FIG. 30B. The tether 1805 can be attached to either or both of the magnets A/A1 at one end and to either of both of the magnets B/B1 at an opposite end. When the set of magnets B/B1 are tethered under tension to the set of magnets A/A1, a change in the shape of the cardiac structure results to improve cardiac function. FIG. 30B shows magnet B positioned in the LV and B1 positioned in a blood vessel BV adjacent to the heart. The magnetic force between B and B1 maintains the location of B and B1. Magnets B and B1 are delivered on or within materials and structures which promote healing and increase the amount of tension that can be placed on the anchor overtime. For example, magnet B1 can be delivered on a stent which is of a length, diameter and material which will heal within the BV to provide sufficient resistance to forces placed on it by the tethers.

The tethers may be pre-attached to the magnets A and B1 or they may be attached after A and B1 have been positioned. The tether length may be shortened and/or adjusted after placement of the anchors. Alternatively the final tether length may be pre-selected based on the patient's cardiac structure geometry and the effect the clinician desires. Placing sets of magnets in this method, enables anchoring of tethers within the heart in various positions and angles which provides increased flexibility and variation for clinicians to select optimal re-shaping of the cardiac structures based on specific patient characteristics.

Examples which demonstrate the flexibility of this approach include placing anchors at the annulus and at the apex of the heart and tethered to shorten the length of the LV; anchors can be placed in the around the annulus and tethered to change the shape of the annulus. More specifically, one or more sets of magnets can be placed in the RA and LA at the level of the mitral valve annulus (on the anterior side of the annulus) and one or more sets of magnets can be placed in the LA and LV on opposite sides of the annulus on the posterior portion of the annulus. The posterior sets of magnets can then be tethered to the anterior sets of magnets to change the shape of the annulus. Alternatively, the magnet anchors can be placed at the level of the annulus in the LA and in a BV adjacent to the heart at the level of the annulus and these then tethered to the anterior annulus magnet anchor described above.

The magnets A and A1 can also be a single magnet that extends through the interventricular septum. Moreover, only one of the magnets A or A1 need be implanted. One or more magnets B and/or B2 are located opposite the location of the magnet(s) A and/or A1. The magnet(s) B is located within the left ventricle opposite the magnets A/A1, such as on the left ventricular wall. The magnet B1 is located on an anatomical structure adjacent the heart, such as on a blood vessel BV.

Figure 30C:
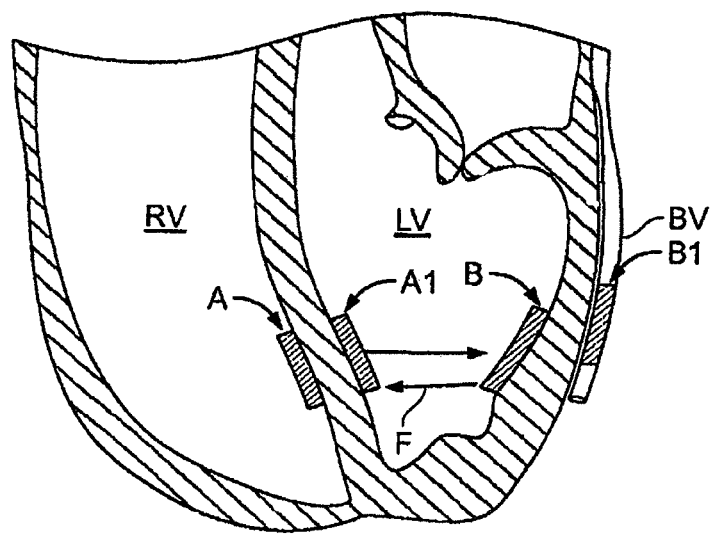
FIG. 30C shows the heart wherein magnets are implanted in various locations to geometrically reshape the annulus or the left ventricle.

In another embodiment shown in FIG. 30C, the magnets A, A1, B, and B1, or combinations thereof, are implanted in the heart without tethers. The magnets A, A1, B, and B1 can be positioned in various combinations so as to exert magnetic attractions to one another to re-shape the left ventricle or the mitral valve annulus. For example, the magnets A and B can be implanted such that they exert an attractive magnetic force relative to one another. The magnets A and B2 can alternately be implanted. Other possible combinations are the magnets A1 and B or the magnets A1 and B2. The magnets can be implanted without tethers such that an attractive magnetic force F causes the magnets and the attached region of the heart to move toward one another to re-shape the heart. Alternately, the magnets can be attached to one another with tethers.

Figure 31:
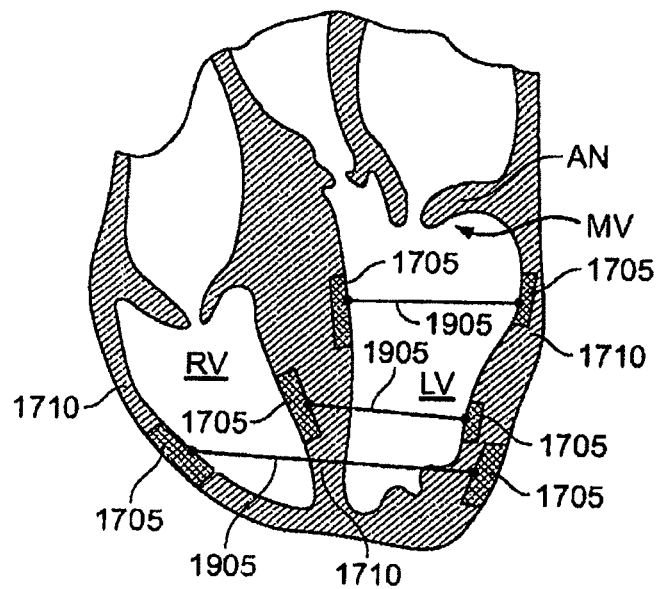
FIG. 31 shows another embodiment of a procedure wherein magnets are implanted in the heart to geometrically reshape the annulus or the left ventricle.

In yet another embodiment, one or more magnets 1705 are implanted in the walls 1710 of the left ventricle LV and/or the right ventricle RV, as shown in FIG. 31. The magnets 1705 are positioned in opposed locations on the walls 1710 and one or more tethers 1905 attach opposed pairs of magnets 1705 to one another. One or more of the tethers 1905 extend through the interventricular septum to connect a first magnet disposed in the left ventricle and a second magnet disposed in the right ventricle. In certain embodiments, magnet elements do not include tethers, but rely on the magnetic attraction to each other to remodel the tissue between them. For example, a magnetic element may be placed on either side of the interventricular septum, or one element within the septum. Another magnetic element may be placed on or within the opposite left ventricular wall, or in an adjacent vessel on the left ventricular wall. The electromagnetic field of such elements can then interact to cause a remodeling of the left ventricle to assist with ventricular function.

The tethers 1905 can be elastic so to exert an attractive force between the attached magnets 1705 and re-shape the left ventricle LV or annulus AN. Alternately, or in combination with elastic tethers, the tethers 1905 can be shortened in length after placement to thereby pull the walls of the left ventricle LV toward one another and re-shape the left ventricle LV or the annulus AN. In combination with the force provided by the tethers 1905, the magnets 1705 exert an attractive magnetic force toward one another to assist in pulling the heart walls toward each other.

It should be appreciated that one or more magnets can be positioned in other locations of the heart or adjacent anatomical structures for re-shaping of the heart. For example, one or more magnets can be positioned around the annulus AN or can be positioned in the coronary sinus in such a manner that the magnets exert attractive forces toward one another to cause re-shaping of a desired portion of the heart.

Figure 32:
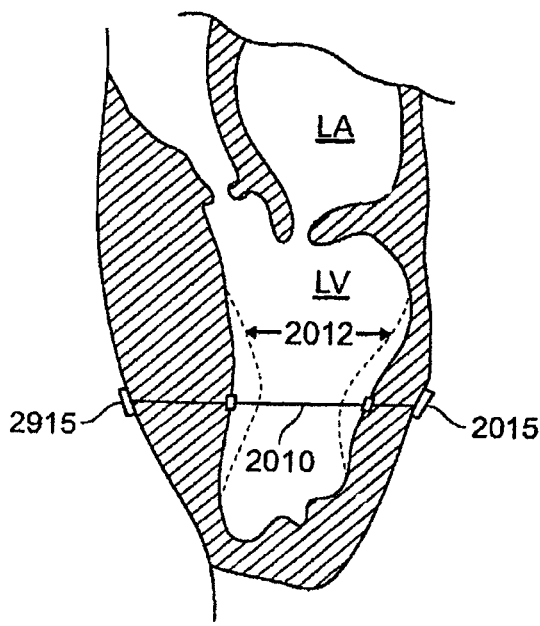
FIG. 32 shows a cross-sectional view of the left ventricle with a tether positioned therein.

In another embodiment, cardiac re-shaping is achieved through percutaneous placement of one or more tethers that are cinched or anchored in the walls of the left ventricle LV. The tethers provide tension between the walls of the left ventricle to reshape the left ventricle LV in a desired manner. FIG. 32 shows a cross-sectional view of the left ventricle LV with a tether 2010 positioned therein. The tether 2010 has a first end anchored to a first wall of the left ventricle LV and a second end anchored to an opposed wall of the left ventricle LV. The tether 2010 is tensioned to pull the walls toward one another (as represented by the phantom lines 2012 in FIG. 32) and re-shape the left ventricle LV. It should be appreciated that the phantom lines 2012 in FIG. 32 are merely representative of the geometric re-shaping. The left ventricle LV can be re-shaped in various manners and the amount of re-shaping can vary depending on the tension applied to the tether 2010 and the location of attachment to the walls of the left ventricle LV. The tether may be inelastic or somewhat elastic.

The tether 2010 can be anchored or otherwise attached to the walls in various manners. In an exemplary embodiment, a patch 2015 (shown in FIG. 32) of material is positioned on an exterior surface of the ventricular wall and is attached to one end of the tether 2010. A similar patch can also be positioned on the opposed wall and attached to the opposite end of the tether.

Figure 33:
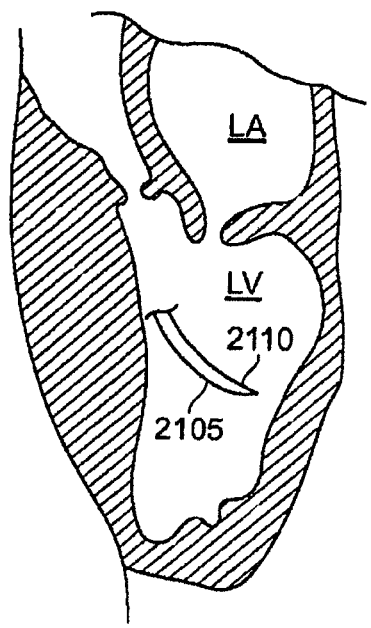
FIG. 33 shows a cross-sectional view of the left ventricle with a delivery catheter positioned therein.
Figure 34:
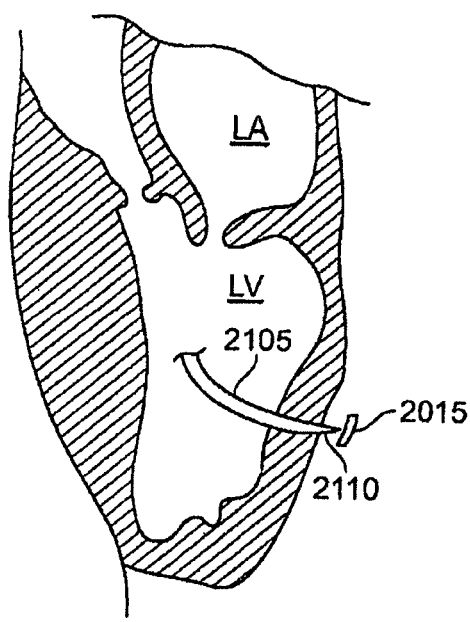
FIG. 34 shows a cross-sectional view of the left ventricle with the delivery catheter penetrating a wall of the left ventricle.

With reference to FIG. 33, the patch is delivered to a desired location using a catheter 2105 having a sharpened distal end 2110 that is positioned within the left ventricle LV. The catheter 2105 can be delivered to the left ventricle LV in various manners, including trans-aortically (via the aorta), trans-septally (by piercing the interventricular septum), and trans-atrially (via the left atrium LA) pursuant to well-known methods. As shown in FIG. 34, the sharpened distal end 2110 pierces the ventricular wall such that the distal end 2110 is positioned exterior to the ventricular wall. The catheter 2105 has an internal delivery lumen having an opening at the distal end 2110. The patch 2015 is configured to be transported in a contracted state through the delivery lumen and delivered out of the opening at the distal end 2110, where the patch 2015 expands into an expanded state at the exterior of the ventricular wall to seal against the exterior of the left ventricular wall.

When positioned at the exterior of the ventricular wall, the patch 2015 is configured to act as a reservoir that receives a fluid material that can be delivered to the patch via the delivery lumen of the catheter 2105. The fluid material has a first viscous state of sufficient fluidity such that the material can flow through the delivery lumen of the catheter 2105 and out of the distal end 2110 to the location of the patch 2015. The fluid material changes to a second viscous state when positioned exterior to the ventricular wall at the patch 2015. The second viscous state is of greater viscosity (i.e., more resistant to flow) than the first viscous state such that the fluid material provides support and a level of rigidity to the patch 2015 and to the left ventricular wall. The fluid material can change to the second viscous state after a predetermined time period, after contact with the patch, or when the patch is completely filled. A catalyst can be injected into the fluid material to cause it to change to the second viscous state.

Figure 35:
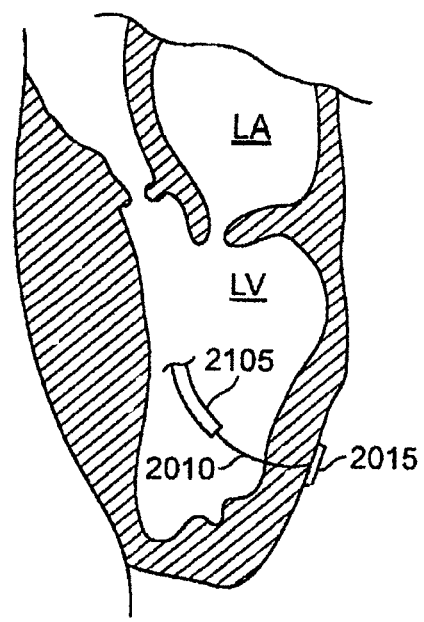
FIG. 35 shows a cross-sectional view of the left ventricle with the delivery catheter delivering a patch to the wall of the left ventricle.

As shown in FIG. 35, the catheter 2105 can then be disengaged from the patch 2015 such that the patch 2015 is disposed exterior to the ventricular wall. The patch 2015 can be firmly attached to the ventricular wall (such as using an adhesive) to minimize wear or friction between the patch and the ventricular wall. Next, an end of the tether 2010 is attached to the patch 2015. The catheter 2105 can be used to deliver the tether 2010 to the patch 2015 or, alternately, a second catheter can be used. In one embodiment, the tether 2010 is already positioned in a delivery lumen of the catheter 2105 while the patch 2015 is being delivered. The catheter 2105 is then pulled back while the end of the tether 2010 remains attached to the patch 2015 to thereby let the tether 2010 out from the catheter 2105, as shown in FIG. 35.

Figures 36, 37:
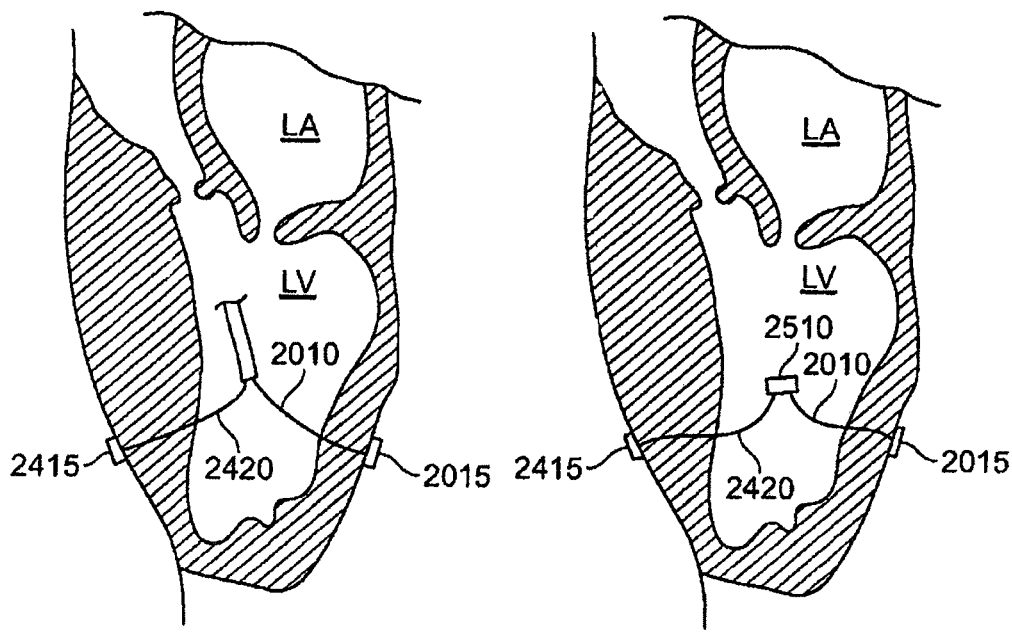
FIG. 36 shows a cross-sectional view of the left ventricle with the delivery penetrating delivering a second patch.
FIG. 37 shows a cross-sectional view of the left ventricle with two tethers attached together at opposite ends from the patches mounted in the heart.

With reference now to FIG. 36, a second patch 2415 is deployed in or exterior to an opposed ventricular wall in a manner similar to that described above. The opposite end of the tether 2010 is then attached to the second patch 2415 such that the tether 2010 extends between the two patches, as shown in FIG. 32. Alternately, as shown in FIG. 36, a second tether 2420 is attached at a first end to the second patch 2415. As shown in FIG. 37, the two tethers 2010 and 2420 can then be attached together at opposite ends from the patches, such as by using a clip 2510, to form a single attachment tether between the patches 2015 and 2415. The tethers 2010 and 2420 can be twisted or adjusted within the clip 2510 to tension the resulting attachment tether between the patches 2415 and 2015 and pull the ventricular walls toward one another via the tether. Once properly tensioned, the tether can be clipped or clamped to maintain its position.

Figures 38, 39:
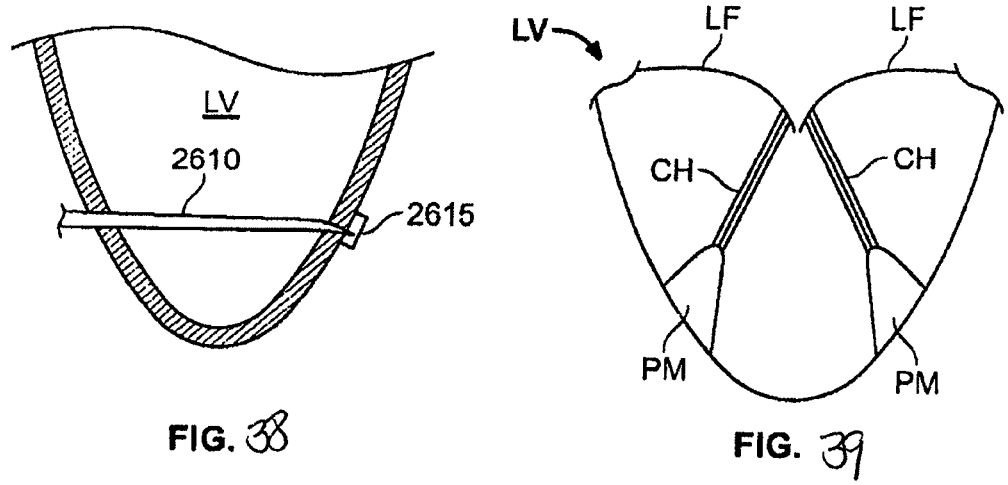
FIG. 38 shows a cross-sectional view of the left ventricle with a needle or delivery catheter passed transthoracically into the left ventricle LV to deliver a patch to the exterior of the ventricular wall.
FIG. 39 shows a schematic, cross-sectional view of the left ventricle in a healthy state with the mitral valve closed.

In another embodiment, shown in FIG. 38, a needle 2610 or delivery catheter is passed trans-thoracically into the left ventricle LV to deliver a patch 2615 to the exterior of the ventricular wall, as described above. A sealing means, such as a sealing balloon, can be used to seal one or more puncture holes in the wall of the left ventricle caused by the needle 2610 during delivery of the patch 2615. Visualization means, such as fluoroscopy, can be used to visualize proper placement of the needle 2610. A second patch is attached to an opposed wall to form a tether attachment between the walls, as shown in FIG. 32. The tether is then tensioned to pull the walls together and re-shape the left ventricle or annulus of the mitral valve in a desired manner.

In other embodiments, described with reference to FIGS. 39-43, cardiac re-shaping is achieved by manipulation of the papillary muscles. FIG. 39 shows a schematic, cross-sectional view of the left ventricle LV in a healthy state with the mitral valve closed. The valve chordae CH connect the leaflets LF of the mitral valve to the papillary muscles PM. The papillary muscles PM and the and chordae CH are positioned such that at least a portion of the leaflets LF contact one another when the mitral valve is in the closed state, resulting in functional coaptation of the leaflets.

Figures 40, 41:
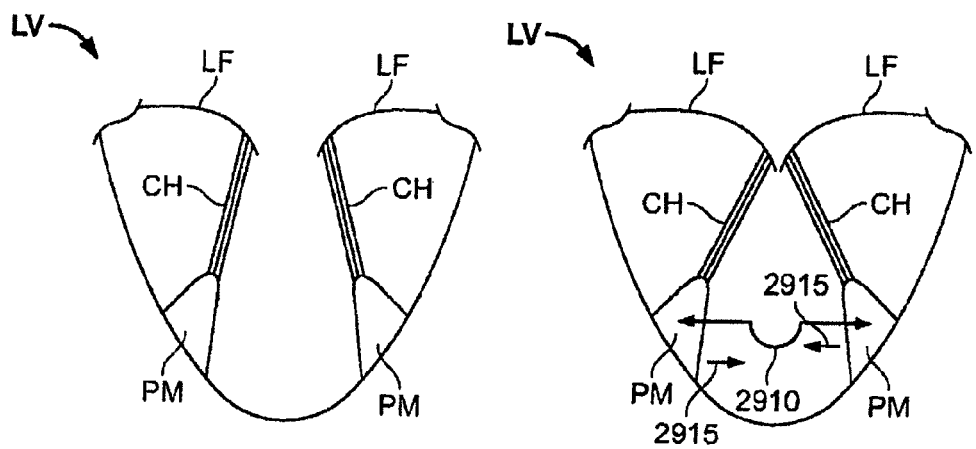
FIG. 40 shows the left ventricle in a dysfunctional state.
FIG. 41 shows the left ventricle with a biasing member mounted between the papillary muscles.

FIG. 40 shows the left ventricle LV in a dysfunctional state. The valve chordae CH or the papillary muscles PM are damaged or otherwise dysfunctional such that the leaflets LF do not properly coapt (contact one another). The dysfunction can be manifested by excess tension in the chordae CH such that a gap is located between the leaflets LF, or in some cases one leaflet may function at a different level from the other (e.g. lower (prolapse) or higher (flail)) thereby limiting the ability of the mitral valve to close resulting in mitral regurgitation. The dysfunctional left ventricle LV and in some cases leaflet prolapse or flail, can be treated by manipulating papillary muscles PM to adjust the position of the leaflets LF. In one embodiment, the papillary muscles PM are repositioned toward one another to reduce the distance between the papillary muscles PM.

In an embodiment described with reference to FIG. 41, a biasing member, such as a rod of adjustable length, or a spring 2910, is mounted between the papillary muscles PM with a first end of the spring 2910 attached to a first papillary muscle and a second end of the spring 2910 attached to a second papillary muscle. The spring 2910 has a pre-load such that the spring 2910 provides a biasing force (represented by the arrows 2915 in FIG. 41) that pulls the papillary muscles PM toward one another. Such a spring may be covered with polyester fabric or other coating to promote ingrowth into the muscle tissue and minimize the potential for clot formation. The repositioning of the papillary muscles PM re-shapes the left ventricle and/or changes the distance that the leaflets need to move on the chordae CH such that the leaflets LF contact one another to close the mitral valve. The tension provided by the spring 2910 can be varied or different springs can be used to achieve a proper repositioning of the papillary muscles PM. The tension may be modified at the time of the procedure or during a subsequent procedure if it is determined that additional coaptation is required.

In another embodiment, described with reference to FIG. 42, a suture 3010 is mounted between the papillary muscles PM with a first end of the suture 3010 attached to a first papillary muscle and a second end of the suture 3010 attached to a second papillary muscle. The suture 3010 can be attached to the papillary muscles in various manners. For example, an attachment device 3015, such as an anchor, cuff or sleeve, can be positioned around or partially around each of the papillary muscles. The ends of the suture 3010 are attached to the attachment devices 3015 to secure the suture 3010 to the suture to the papillary muscles.

The suture 3010 is tensioned such that it provides a force that pulls the papillary muscles PM toward one another. The suture 3010 can be tensioned, for example, by twisting the suture 3010 to reduce its the overall length and thereby reduce the distance between the papillary muscles PM, and fixing the suture with a crimping element or other stay element. The amount of twisting or shortening can be varied to vary the tension provided by the suture 3010. In addition, a crimping member may be used to fix the sutures once a desired tension between the muscles is reached. Exemplary crimping members are described in International Patent Application Number PCT/US03/06149, which is incorporated herein by reference in its entirety. As in the previous embodiment, the repositioning of the papillary muscles PM re-shapes the left ventricle and/or changes the tension on the chordae CH such that the leaflets LF contact one another to close the mitral valve. Cuffs or sleeves may be placed around the papillary muscles PM to such as those previously described, to affect the repositioning.

Figures 42, 43:
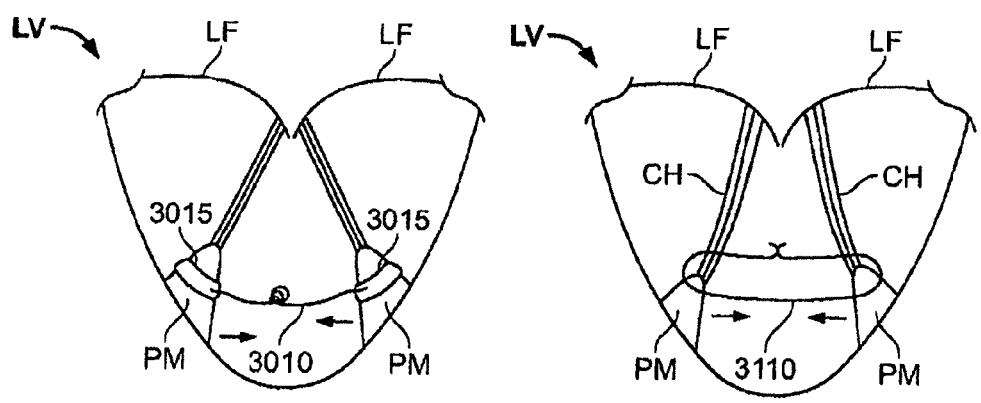
FIG. 42 shows the left ventricle with a suture mounted between the papillary muscles.
FIG. 43 shows the left ventricle with a snare positioned around the chordae at or near the location where the chordae attach with the papillary muscles.

With reference now to FIG. 43, the papillary muscles PM can also be repositioned by snaring the papillary muscles. A snare 3110 comprised of a looped strand of material is positioned around the chordae CH at or near the location where the chordae attach with the papillary muscles PM. The snare 3110 is tightened to draw the papillary muscles PM toward one another and re-shape the left ventricle and/or changes the distance that the leaflets need to travel during systole such that the leaflets LF contact one another to close the mitral valve.

In yet another embodiment, shown in FIG. 48, one or more clips 3610 are clipped to each of the papillary muscles PM. The structure of the clips 3610 can vary. A tether 3615 attaches the clips 3610 to one another. The tether 3615 is cinched to shorten the length of the tether 3615 and pull the papillary muscles PM toward one another and re-shape the left ventricle and/or changes the distance that the leaflets need to travel during systole such that the leaflets LF contact one another to close the mitral valve.

In yet another embodiment, shown in FIG. 49, one or more clips 3610 are clipped to opposed walls of the left ventricle LV. The clips 3610 can be delivered to the left ventricle using a delivery catheter 2105. A tether attaches the clips to one another. The tether is cinched to shorten the length of the tether and pull the ventricular walls toward one another and re-shape the left ventricle and/or changes the distance that the leaflets need to travel during systole such that the leaflets LF contact one another to close the mitral valve.

In all embodiments, once the papillary muscles are fixed or repositioned, it may be advantageous to further treat the area by selectively elongating or shortening the chordae tendinae to achieve further optimal valve function. In addition, a mitral valve clip may be deployed to augment the desired valve function, either before papillary or chordal manipulation, or after, if the desired leaflet coaptation is not achieved with one particular approach.

As discussed above with reference to FIG. 40, a dysfunctional left ventricle can be manifested by excess tension in the chordae CH such that a gap is positioned between the valve leaflets LF. It can be desirable to eliminate or relieve the excess tension by cutting the chordae CH, and/or cutting the chordae and replacing them with artificial chordae. Prior to cutting the chordae, it can be desirable to evaluate the placement of the artificial chordae to confirm that implantation of the chordae will indeed provide the desired clinical result. This process is now described with reference to FIGS. 44-47.

Figure 44:
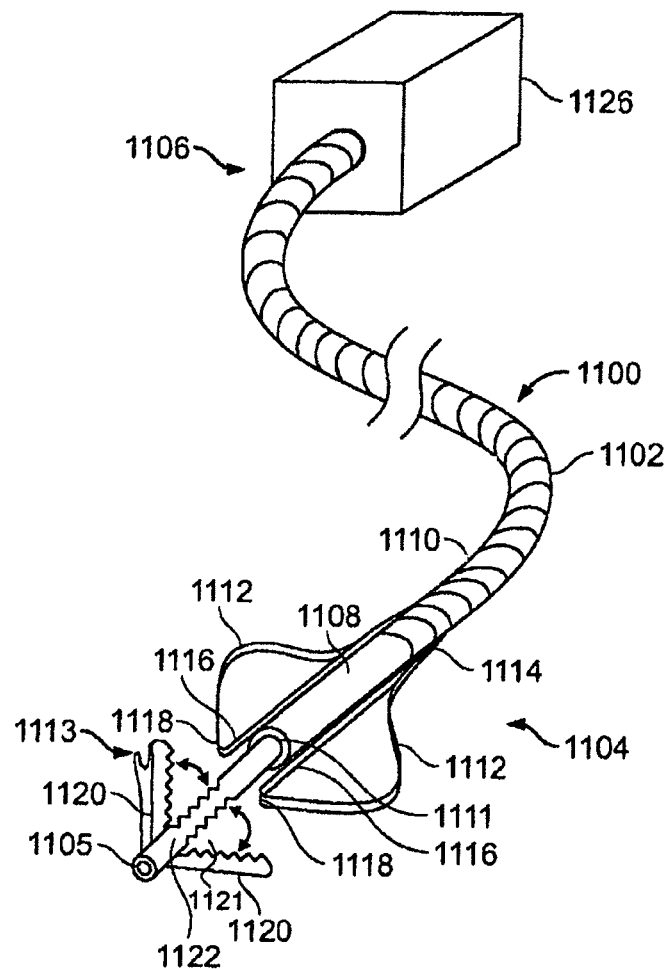
FIG. 44 shows a leaflet grasping device that is configured to grasp and secure the leaflets of the mitral valve.

FIG. 44 shows a leaflet grasping device 1100 that is configured to grasp and secure the leaflets of the mitral valve. The device 1100 and corresponding methods of use are described in more detail in U.S. Patent Application Publication No. 2004-0030382, entitled "Methods and Apparatus For Cardiac Valve Repair", which is incorporated herein by reference in its entirety. Additional leaflet grasping devices are described in U.S. Patent Application Publication No. 2004-0092962, filed May 19, 2003, U.S. Pat. No. 6,269,819, issued Aug. 7, 2001, and U.S. Pat. No. 6,461,366, issued Oct. 8, 2002, all of which are expressly incorporated by reference herein.

Referring to FIG. 44, the device 1100 is comprised of a catheter shaft 1102 having a distal end 1104 and a proximal end 1106. The catheter shaft 1102 is comprised of, among others, a conduit 1108, a coaxial outer sheath 1110, a central lumen 1111 through which a double-jaw grasper 1113 may be inserted, and a central guidewire lumen 1105. The catheter shaft 1102 can have additional lumens for the passage of one or more needles, as described more fully below.

Toward the distal end 1104, an optional pair of stabilizers 1112 are fixedly mounted on the outer sheath 1110 at their proximal end 1114 and fixedly attached to extenders 1116 at their distal end 1118. The stabilizers 1112 are shown in an outwardly bowed position, however they may be inwardly collapsed by either extending the extenders 1116 or retracting the outer sheath 1110. Bowing may be achieved by the reverse process.

The double-jaw grasper 1113 is comprised of two articulating jaw arms 1120 which may be opened and closed against the central shaft 1122 (movement depicted by arrows) either independently or in tandem. The grasper 1113 is shown in the open position in FIG. 44. The surfaces of the jaw arms 1120 and central shaft 1122 may be toothed, as shown, or may have differing surface textures for varying degrees of friction. The jaw arms 1120 each include a needle passageway 1121 comprised of a cutout or a slot that extends at least partially along the length of each jaw arm 1120. As described in more detail below, the needle passageway provides a location where a needle can pass through the jaw arm 1120 during manipulation of the papillary muscle.

The above described components may be manipulated and controlled by a handle 1126 connected to the proximal end 1106 of the catheter shaft 1102, as shown in FIG. 44. The handle 1026 permits independent control of the components described above.

Figure 45A:
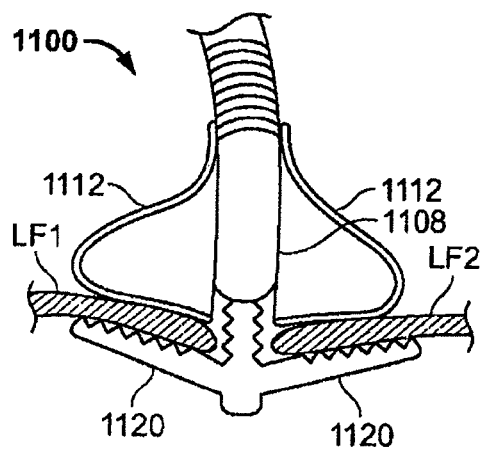
FIGS. 45A-45C show the leaflet grasping device grasping leaflets of the mitral valve.
Figure 45B:
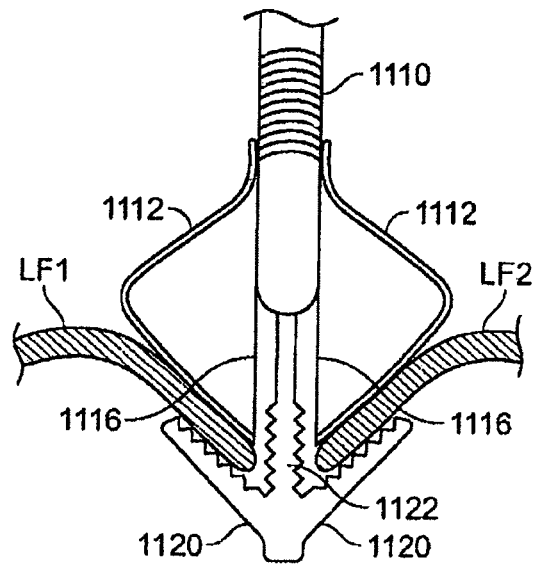
Figure 45C:
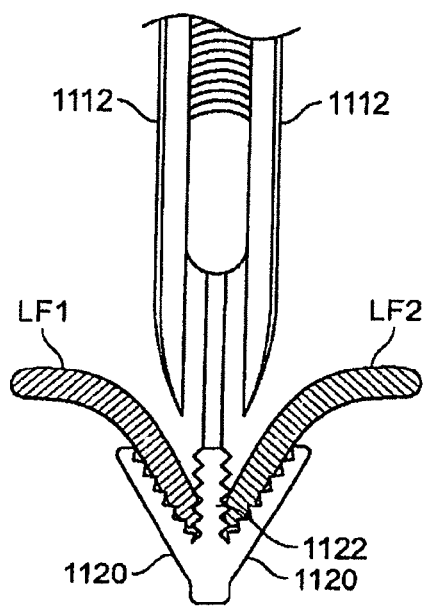

Referring to FIGS. 45A-C, the device 1100 may be used at least temporarily grasp and restrain the valve leaflets LF of the mitral valve MV. The double-jaw grasper 1113 extends through the valve such that the leaflets LF1, LF2 are grasped from below. Thus, the device 1100 is termed "atrial-ventricular."

Referring to FIG. 45A, the atrial device 1100 may be stabilized against the mitral valve MV. The stabilizers 1112 may be positioned on the superior surface of the valve leaflets LF1, LF2 at a 90 degree angle to the line of coaptation. The grasper 1113 may be advanced in its closed position from the conduit 1108 between the leaflets LF1, LF2 until the jaw arms 1120 are fully below the leaflets in the ventricle. At this point, the grasper 1113 may be opened and retracted so that the jaw arms 1120 engage the inferior surface of the leaflets LF1, LF2. In this manner, the leaflets are secured between the stabilizers 1112 and the jaw arms 1120.

Referring to FIG. 45B, the grasper 1113 will gradually close, drawing the leaflets LF1, LF2 together while maintaining a secure hold on the leaflets between the jaw arms 1120 and the stabilizers 1112. This may be accomplished by number of methods. For example, the stabilizers 1112 may be gradually collapsed by either extending the extenders 1116 or retracting the outer sheath 1110. As the stabilizers 1112 collapse, the jaw arms 1120 may collapse due to spring loading to gradually close the grasper 1113. Alternatively, the jaw arms 1120 may be actuated to close against the central shaft 1122 applying force to the stabilizers 1112 causing them to collapse. In either case, such action allows the stabilizers 1112 to simultaneously vertically retract and withdraw from the leaflets as the leaflets are clamped between the jaw arms 1120 and the central shaft 1122. In this manner, the leaflets are effectively "transferred" to the grasper 1113. Referring to FIG. 45C, once the collapsed stabilizers 1112 are completely withdrawn, the leaflets LF1, LF2 are held in vertical opposition by the grasper 1113 in a more natural coaptation geometry.

With reference now to FIG. 46, a needle 3410 is advanced from the left atrium into the left ventricle. The needle 3410 can be passed through a lumen in the device 1100 or it can be passed external to the device 1100. In any event, the needle 3410 passes through a leaflet LF and into a papillary muscle PM. As mentioned, the jaw arms 1120 have needle passageways 1121 (shown in FIG. 44) that permit passage of the needle through the jaw arms 1120.

The needle 3410 is attached to a suture 3415 that extends distally through the device 1100. The suture 3415 is then anchored to the papillary muscle PM such that the suture 3415 provides an attachment for holding, pulling, or otherwise manipulating the papillary muscle PM. The tension in the suture 3415 can be adjusted to re-position the papillary muscle PM such that the leaflets LF contact one another to close the mitral valve. The same process can be performed with the other papillary muscle.

With the sutures 3415 holding the papillary muscles PM in a desired position, as shown in FIG. 47, the chordae CH may be cut. The sutures 3415 function as artificial chordae that retain the leaflets LF and papillary muscles PM in a desired orientation.

A fixation device such as a clip can then be attached to the leaflets using methods and device described in U.S. Patent Application Publication No. 20040030382, filed Aug. 5, 2003, U.S. Patent Application Publication No. 20040092962, filed May 19, 2003, U.S. Pat. No. 6,269,819, issued Aug. 7, 2001, and U.S. Pat. No. 6,461,366, issued Oct. 8, 2002, all of which are expressly incorporated by reference herein. The sutures 3415 can be attached to the clip 3510 or directly to the leaflets LF. It should be appreciated that any quantity of sutures 3415 can be used as artificial chordae between the leaflets and the papillary muscles. It should be appreciated that the leaflet clips can also be used in conjunction with cutting, elongating, or shortening of the chordae pursuant to the methods described above.

Prior to permanently placing the chordae or clips, the result can be previewed on ultrasound (TEE, ICE, echocardiography), to determine if the appropriate valve coaptation is restored. In addition, it is within the scope of the present invention to implant a mitral valve clip in addition to performed papillary muscle approximation or chordal implantation.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A device for treating regurgitation through a gap in a valve in a heart, the heart having an atrium fluidically coupled to a ventricle by the valve, the valve including at least two leaflets which coapt along a line of coaptation, the device comprising:
   a frame sized to fit within a heart chamber;
   a pair of arms moveably coupled to the frame, the arms are structurally configured to move from a fluid flow-blocking position during a systole to a fluid flow-allowing position during a diastole in response to pressure changes occurring between the systole and the dystole;
   an anchoring mechanism having a tether and an anchor positioned in a wall of the ventricle, wherein the tether interconnects the frame to the anchor; and
   a compliant membrane covering the frame and at least a portion of the pair of arms,
   wherein the frame further comprises a stationary portion coupled to a proximal portion of the pair of arms, wherein the stationary portion is positioned above the level of the annulus and wherein the stationary portion has a long axis oriented orthogonal to the line of coaptation.

2. The device of claim 1, wherein the pair of arms are coupled to the frame by a hinge.

3. The device of claim 1, wherein the tether connects to the frame at a lower surface of the stationary portion.

4. The device of claim 1, wherein the long axis of the stationary portion has a length sufficient to contact an anterior and posterior annulus.

5. The device of claim 1, wherein the device can be repositioned in the heart, redeployed in the heart and removed from the heart.

* * * * *